United States Patent
Herr et al.

(10) Patent No.: US 10,267,795 B2
(45) Date of Patent: Apr. 23, 2019

(54) ELECTROPHORETIC SEPARATION DEVICES AND METHODS FOR USING THE SAME

(71) Applicant: The Regents of the University of California, Oakland, CA (US)

(72) Inventors: Amy E. Herr, Oakland, CA (US); Alex James Hughes, Berkeley, CA (US); Elly Sinkala, Oakland, CA (US); Todd A. Duncombe, Berkeley, CA (US); Kevin A. Yamauchi, Berkeley, CA (US); Julea Vlassakis, Berkeley, CA (US); Chi-Chih Kang, Berkeley, CA (US); Zhuchen Xu, Berkeley, CA (US); Robert Lin, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 139 days.

(21) Appl. No.: 14/650,520

(22) PCT Filed: Mar. 6, 2014

(86) PCT No.: PCT/US2014/021399
§ 371 (c)(1),
(2) Date: Jun. 8, 2015

(87) PCT Pub. No.: WO2014/138475
PCT Pub. Date: Sep. 12, 2014

(65) Prior Publication Data
US 2015/0316547 A1    Nov. 5, 2015

Related U.S. Application Data

(60) Provisional application No. 61/866,396, filed on Aug. 15, 2013, provisional application No. 61/805,414, (Continued)

(51) Int. Cl.
G01N 27/447    (2006.01)
G01N 27/453    (2006.01)
G01N 33/561    (2006.01)

(52) U.S. Cl.
CPC ..... G01N 33/561 (2013.01); G01N 27/44726 (2013.01); G01N 27/44747 (2013.01); G01N 27/44791 (2013.01)

(58) Field of Classification Search
CPC .......... G01N 27/447; G01N 27/44721; G01N 27/44743; G01N 27/44756; G01N 27/453;
(Continued)

(56) References Cited

U.S. PATENT DOCUMENTS 3,674,678 A * 7/1972 Post, Jr. ........... G01N 27/44756
                                                            204/616
5,006,473 A * 4/1991 Bouma ................ G01N 33/561
                                                            204/462
(Continued)

FOREIGN PATENT DOCUMENTS

CN    102037351    4/2011
CN    102308213    1/2012
(Continued)

OTHER PUBLICATIONS

Hughes et al., "Photo-Clickable Separation Gels Enable Targeted Proteomics of Cancer Biomarker Isoforms: A 'Single Channel, Multi-Stage' Strategy", 15th International Conference on Miniaturized Systems for Chemistry and Life Sciences Oct. 2-6, 2011, Seattle, Washington, USA.*
(Continued)

*Primary Examiner* — Alexander S Noguerola
(74) *Attorney, Agent, or Firm* — Rudy J. Ng; Bret E. Field; Bozicevic, Field & Francis LLP

(57) ABSTRACT

Electrophoretic separation devices and methods for using the same are provided. Aspects of the devices include a
(Continued)

polymeric separation medium that includes a plurality of microwells. Also provided are methods, systems and kits in which the subject devices find use. The devices and methods find use in a variety of different electrophoretic separation applications.

24 Claims, 40 Drawing Sheets

Related U.S. Application Data filed on Mar. 26, 2013, provisional application No. 61/774,519, filed on Mar. 7, 2013.

(58) Field of Classification Search
CPC .. G01N 27/44791; G01N /; C07K 1/26–1/285
See application file for complete search history.

(56) References Cited

U.S. PATENT DOCUMENTS

| | | | | |
|---|---|---|---|---|
| 5,061,336 A * | 10/1991 | Soane | ............... | B29C 35/0888 156/245 |
| 5,785,835 A * | 7/1998 | Saito | ............... | G01N 27/44782 204/456 |
| 6,024,854 A * | 2/2000 | Gilchrist | ............ | G01N 27/44743 204/466 |
| 6,071,396 A * | 6/2000 | Day | ................ | G01N 27/44782 204/616 |
| 6,136,172 A * | 10/2000 | Renfrew | .......... | G01N 27/44704 204/456 |
| 6,562,213 B1 * | 5/2003 | Cabilly | ............ | G01N 27/44713 204/456 |
| 6,632,619 B1 * | 10/2003 | Harrison | ............. | B01J 19/0093 422/504 |
| 6,664,047 B1 * | 12/2003 | Haugland | ............... | C09B 23/02 435/29 |
| 6,818,112 B2 | 11/2004 | Schneider et al. | | |
| 7,285,412 B2 * | 10/2007 | Casagrande | .......... | B01L 3/5085 435/177 |
| 7,846,676 B2 | 12/2010 | Yang et al. | | |
| 7,935,308 B2 | 5/2011 | O'Neill et al. | | |
| 7,935,479 B2 | 5/2011 | O'Neill et al. | | |
| 7,935,489 B2 | 5/2011 | O'Neill et al. | | |
| 8,628,651 B2 * | 1/2014 | Dhawan | ........... | G01N 27/44704 204/466 |
| 9,108,195 B2 | 8/2015 | Herr et al. | | |
| 2002/0155591 A1 | 10/2002 | Farina et al. | | |
| 2003/0134428 A1 * | 7/2003 | Shanler | ................ | B01L 3/0244 436/180 |
| 2004/0262160 A1 | 12/2004 | Schneider et al. | | |
| 2005/0003521 A1 | 1/2005 | O'Connor et al. | | |
| 2005/0170362 A1 | 8/2005 | Wada et al. | | |
| 2006/0029978 A1 | 2/2006 | O'Neill et al. | | |
| 2006/0240453 A1 | 10/2006 | Jacobs et al. | | |
| 2007/0052781 A1 | 3/2007 | Fraden et al. | | |
| 2007/0264623 A1 | 11/2007 | Wang et al. | | |
| 2008/0009078 A1 | 1/2008 | O'Neil et al. | | |
| 2008/0017512 A1 | 1/2008 | Bordunov et al. | | |
| 2008/0057557 A1 * | 3/2008 | Margalit | ............ | G01N 27/4473 435/173.9 |
| 2008/0139689 A1 | 6/2008 | Huang et al. | | |
| 2008/0254552 A1 | 10/2008 | O'Neill et al. | | |
| 2009/0042742 A1 | 2/2009 | Ofstead et al. | | |
| 2009/0060797 A1 | 3/2009 | Mathies et al. | | |
| 2010/0216228 A1 | 8/2010 | Love et al. | | |
| 2011/0177618 A1 | 7/2011 | Herr et al. | | |
| 2012/0015824 A1 | 1/2012 | Love et al. | | |
| 2012/0045368 A1 | 2/2012 | Hinz et al. | | |
| 2012/0142904 A1 | 6/2012 | He et al. | | |
| 2012/0178172 A1 * | 7/2012 | Buvat | ..................... | C09B 57/02 436/104 |
| 2012/0277118 A1 * | 11/2012 | Bhatia | ............... | B01L 3/502715 506/10 |
| 2012/0329040 A1 | 12/2012 | Herr et al. | | |
| 2013/0052649 A1 | 2/2013 | Lee et al. | | |
| 2016/0011190 A1 | 1/2016 | Herr et al. | | |

FOREIGN PATENT DOCUMENTS

| | | | | |
|---|---|---|---|---|
| EP | 0425485 | 10/2000 | | |
| EP | 1813938 A1 * | 1/2006 | ........... | G01N 27/447 |
| JP | 2006071368 | 3/2006 | | |
| WO | 1999022228 | 5/1999 | | |
| WO | 0281084 | 10/2002 | | |
| WO | 2009073632 | 6/2009 | | |
| WO | WO 2010135364 | 11/2010 | | |

OTHER PUBLICATIONS

"Size Comparisons of Bacteria, Amoeba, Animal & Plant Cells," Education—Seattle PI downloaed on Aug. 14, 2017 from http://education.seattlepi.com/size-comparisons-bacteria-amoeba-animal-plant-cells-4966.html.*
Mottaghinejad et al., Synthesis of Fluorescent Polyacrylamide Based on Dansyl Chloride [5-Dimethylaminonaphthalene-1-Sulfonyl Chloride], Macromolecules—An Indian Journal (MMAIJ), 3(2), 2007 [60-63] (Year: 2007).*
Liu et al., "Fluorescent-tagged acrylinc acid-allylpolyethoxy carboxylate copolymer as a green inhibitor for calcium phosphate in industrial cooling systems," Designed Monomers and Polymers vol. 16, No. 1, Jan. 2013, 89-98 (Year: 2013).*
Hughes et al., "Microfluidic western blotting," PNAS (2012) 109(52): 21450-21455.
Yin and Marshall "Microfluidics for single cell analysis," Current Opinion in Biotechnology, (2012) 23: 110-119.
Ciaccio et al., "Systems analysis of EGF receptor signaling dynamics with microwestem arrays" HHS Public Access Author Manuscript (2010) 7(2): 148-155. (XP055297551).
Hughes et al., "Single-cell western blotting" HHS Public Access Author Manuscript, (2014) 11(7): 749-755. (XP55297548).
Kang et al., "Single-Cell Western Blotting after Whole-Cell Imaging to Assess Cancer Chemotherapeutic Response," Analytical Chemistry (2014) 86(20): 10429-10436. (XP55297542).
Kang et al., "Single cell-resolution western blotting," Nature Protocols, (2016) 11(8): 1508-1530. (XP55297539).
Hughes et al., (2012) "Microfluidic Western blotting" Proceedings of the National Academy of Sciences; 109 (52):21450-21455.
Papautsky et al. (2001) "High lane density slab-gel electrophoresis using micromachined instrumentation," Electrophoresis; 22:3908-3915.
Sims et al., (2007) "Analysis of single mammalian cells on-chip," Lab on a Chip; 7:423-440.
Cao et al., "Photoimmobilization of biomolecules within a 3-dimensional hydrogel matrix", J. Biomater. Sci. Polymer Edn, (2002) 13(6):623-636.
Extended European Search Report dated Dec. 8, 2014 from corresponding EP Application No. 12802542.6, 7 pages.
Fan et al., "Nanofluidic proteomic assay for serial analysis of oncoprotein activation in clinical specimens" Nature Medicine, (2009) 15(5):566-571.
He et al., "Automated microfluidic protein immunoblotting", Nature Protocols, (2010) 5(11) 1844-1856 (2010).
Herr et al., "Photopolymerized Cross-Linked Polyacrylamide Gels for on-Chip Protein Sizing" Anal. Chem. (2004) 76:4727-4733.
Hughes et al., "Microfluidic integration for automated targeted proteomic assays.", Proc. Natl. Acad. Sci. USA, (2012) 109(16) : 5972-5977.
Hughes et al., "Photo-Clickable Separation Gels Enable Targeted Proteomics of Cancer Biomarker Isoforms: A Single Channel, Multi-Stage' Strategy", 15th International Conference on Miniaturized Systems for Chemistry and Life Sciences, (2011): 2074-2076.
Lo et al., "Photopolymerized diffusion-defined polyacrylamide gradient gels for on-chip protein sizing" Lab on a Chip, (2008) 8(8):1273-1279.
O'Neill et al., "Isoelectric focusing technology quantifies protein signaling in 25 cells", PNAS, (2006) 103(44): 16153-16158.

(56) References Cited

OTHER PUBLICATIONS

Rustandi; et al. "Qualitative and quantitative evaluation of SimonTM, a new CE-based automated Western blot system as applied to vaccine development", Electrophoresis (2012) 33: 2790-2797.
Sanford et al., "Photoactivatable Cross-Linked Polyacrylamide for the Site-Selective Immobilization of Antigens and Antibodies", Chem. Mater.,(1998) 10(6): 1510-1520.
Shainoff, "Zonal Immobilization of Proteins", Biochemical and Biophysical Research Communications, (1980) 95(2): 690-695.

* cited by examiner

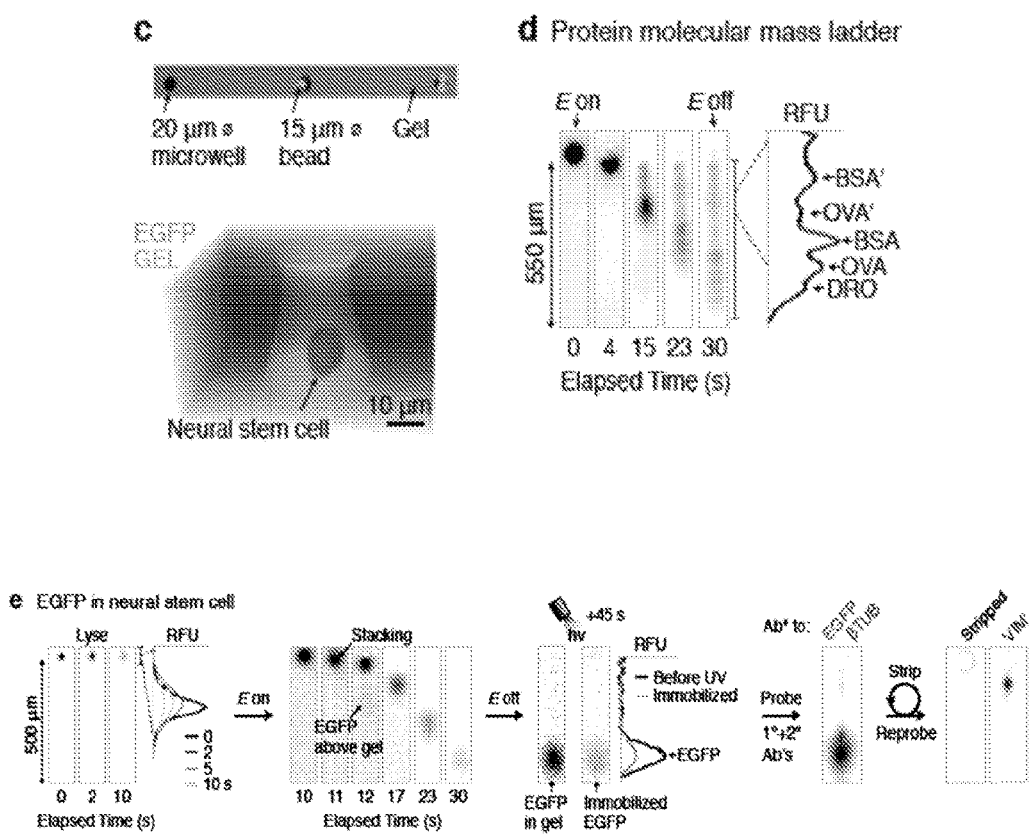
FIG. 1, continued

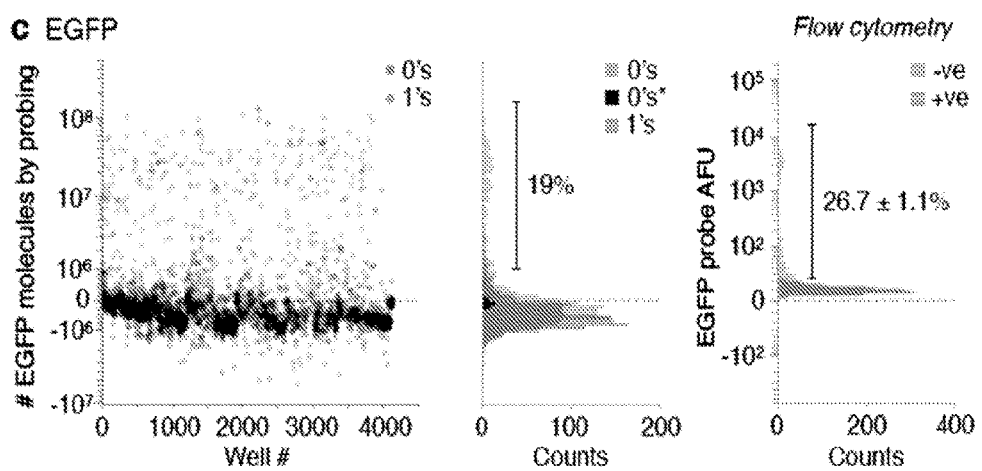
FIG. 2, continued

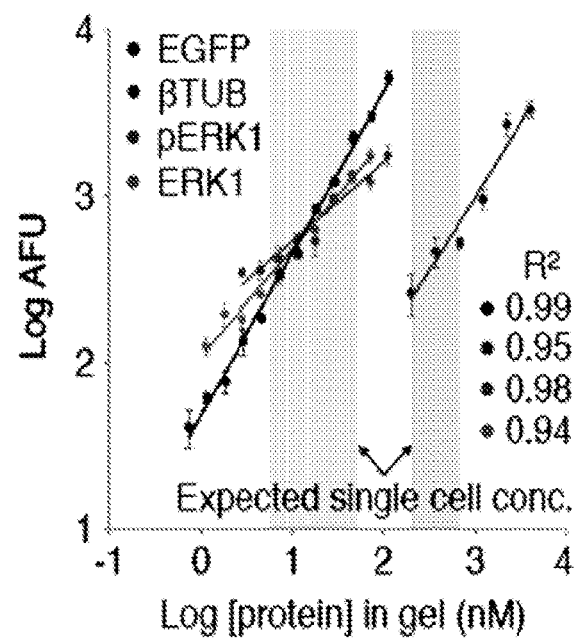
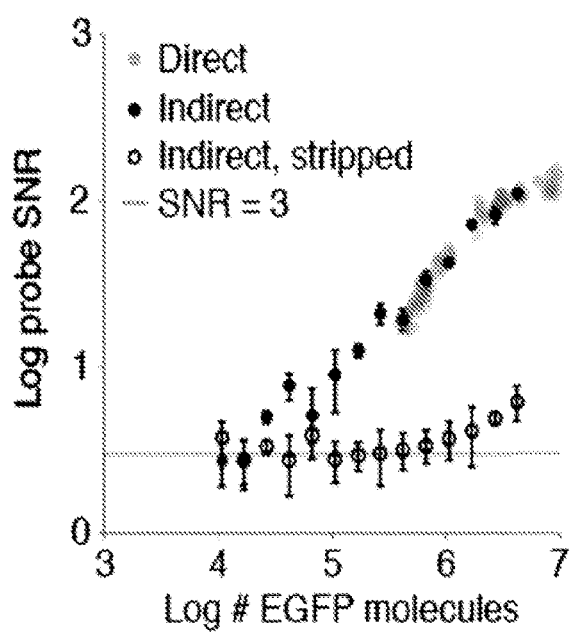
FIG. 2, continued c *Conventional western blot (WB)*
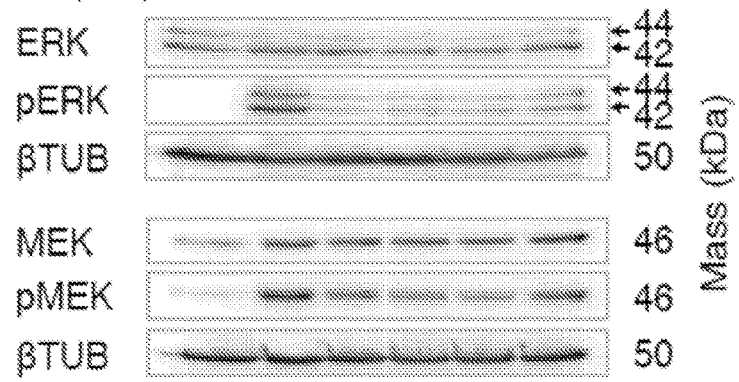
d *scWestern blot (scWB)*
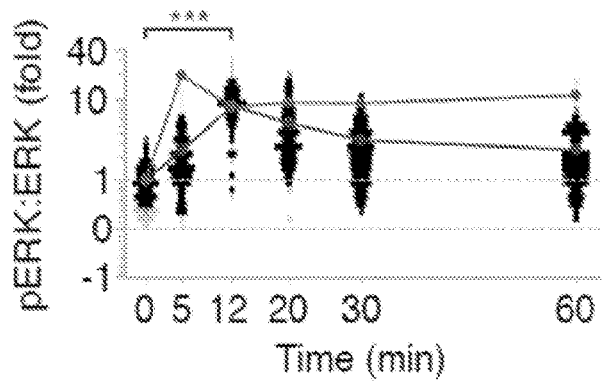
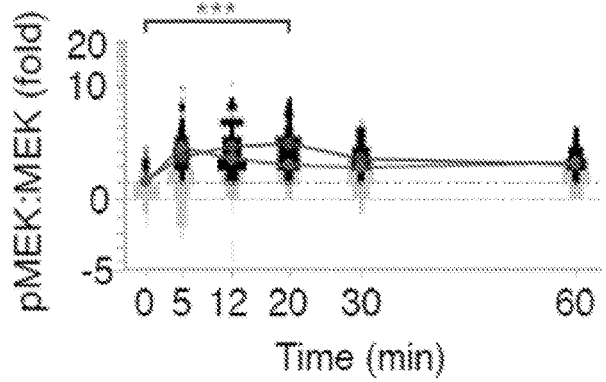
FIG. 3, continued

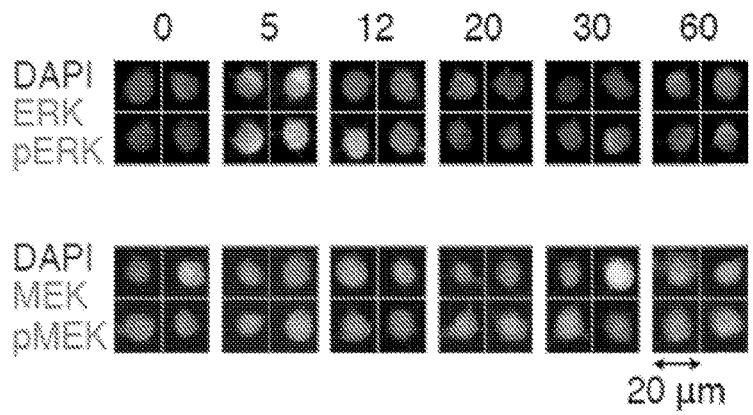
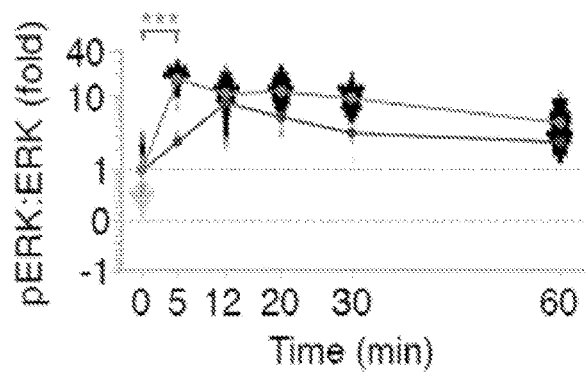
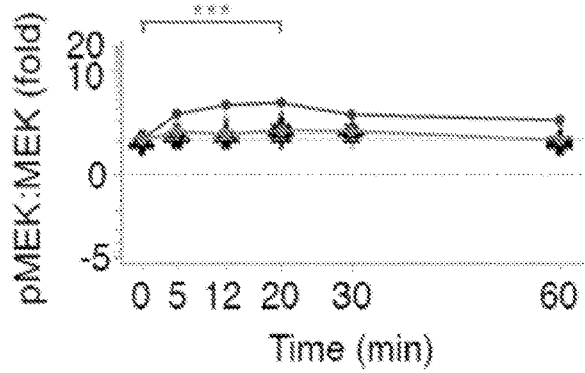
FIG. 3, continued

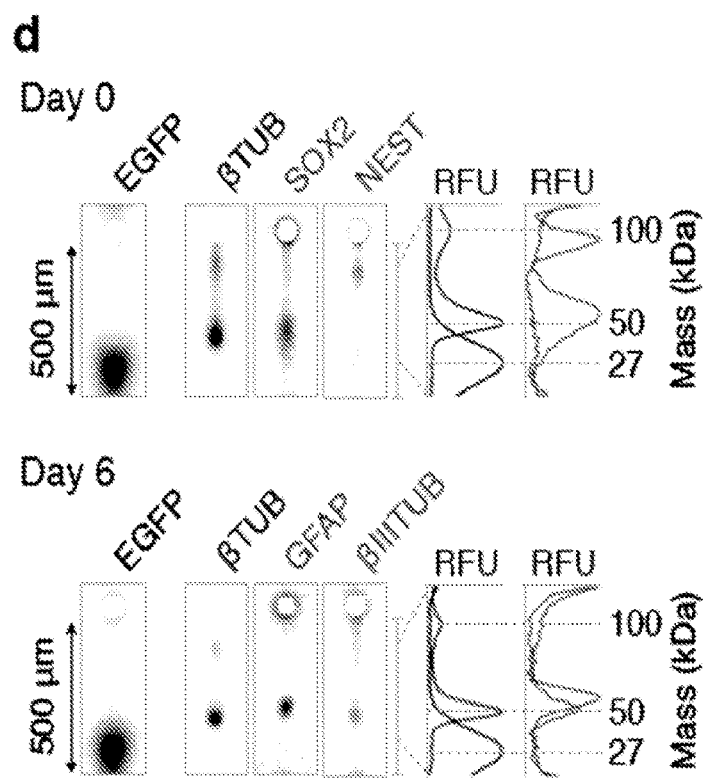
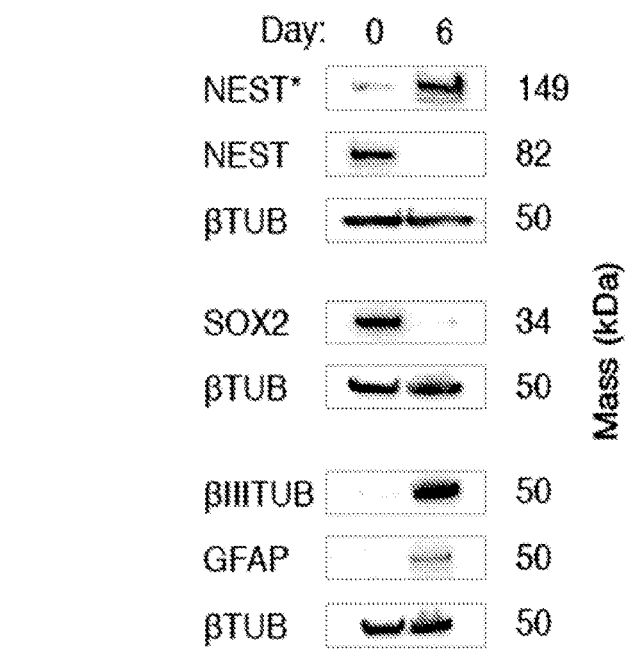
FIG. 4, continued

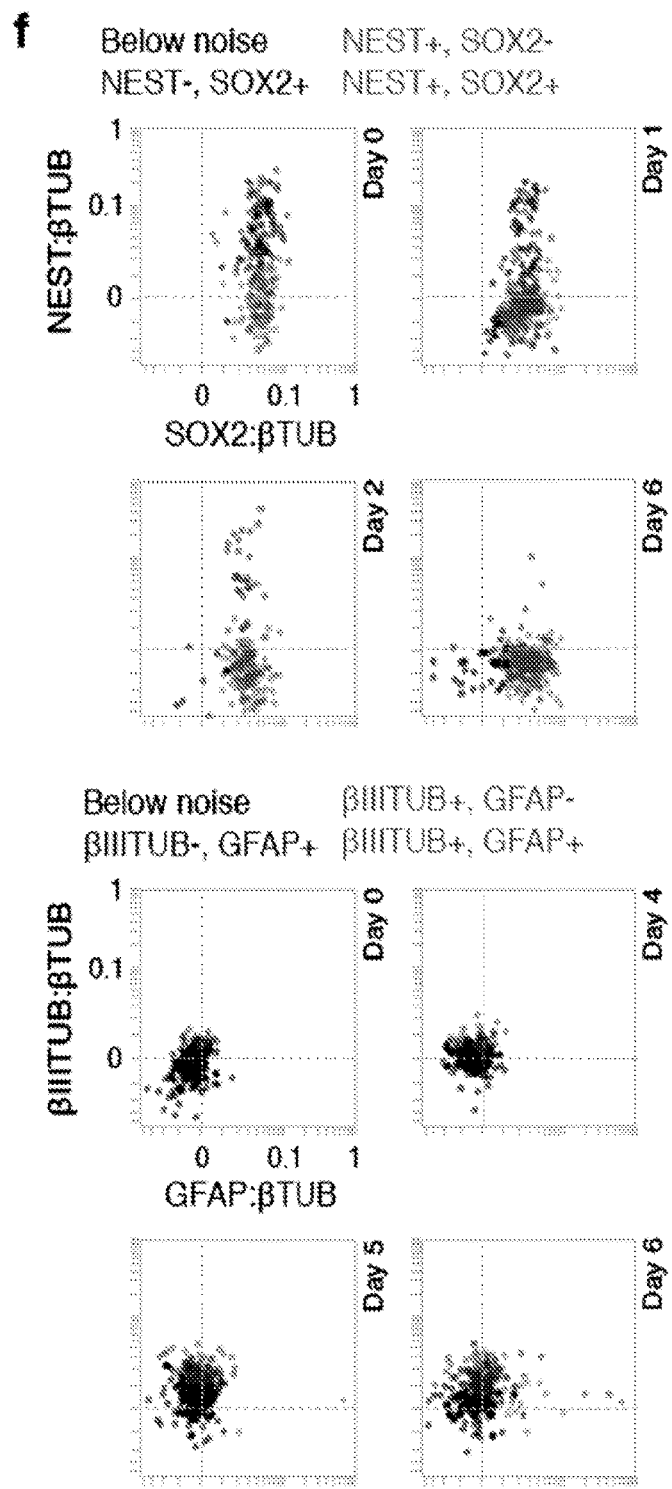
FIG. 4, continued

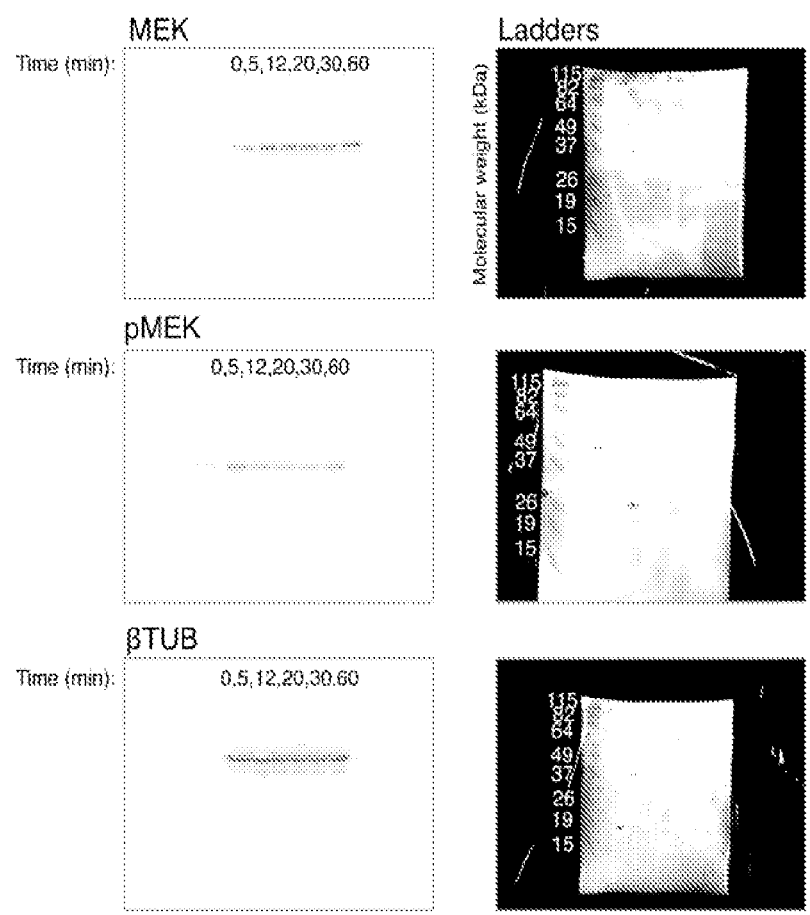
FIG. 22, continued

ELECTROPHORETIC SEPARATION DEVICES AND METHODS FOR USING THE SAME

CROSS-REFERENCE TO RELATED APPLICATIONS

Pursuant to 35 U.S.C. § 119(e), this application claims priority to the filing dates of U.S. Provisional Application No. 61/774,519, filed Mar. 7, 2013, U.S. Provisional Application No. 61/805,414, filed Mar. 26, 2013, and U.S. Provisional Application No. 61/866,396, filed Aug. 15, 2013, the disclosures of each of which are incorporated herein by reference.

REFERENCE TO GOVERNMENT SUPPORT

This invention was made with government support under grant number OD007294 awarded by the National Institutes of Health, and grant number 1056035 awarded by the National Science Foundation. The government has certain rights in the invention.

INTRODUCTION

A variety of analytical techniques may be used to separate and detect specific analytes in a given sample. A range of related immunoblotting methods have enabled the identification and semi-quantitative characterization of e.g., DNA (Southern blot), RNA (northern blot), proteins (Western blot), and protein-protein interactions (far-western blot); by coupling biomolecule separations and assays. For example, Western blotting can be used to detect proteins in a sample by using gel electrophoresis to separate the proteins in the sample followed by probing with antibodies specific for the target protein. In a typical Western blot, gel electrophoresis is used to separate native proteins by 3-D structure or denatured proteins by the length of the polypeptide. The proteins are then transferred to a membrane (typically nitrocellulose or PVDF), where they are probed (detected) using antibodies specific to the target protein.

Proteomic analysis of rare cell populations may be challenging due to very low cell concentrations in an analysis sample. For example, circulating tumor cells may be present at 1-10 cells per mL of blood, and may not be suitable for conventional assays (e.g., western blots and flow cytometry), which require ~$10^6$ cells for accurate results. Additionally, the analysis of a large cell population can obscure sub-populations that behave differently than the average. Cell-to-cell variability can lead to different outcomes, and thus the study of individual cell behavior may be performed by single-cell analysis.

SUMMARY

Electrophoretic separation devices and methods for using the same are provided. Aspects of embodiments of the present disclosure include a device that includes a polymeric separation medium having a plurality of microwells. The polymeric separation medium includes functional groups that covalently bond to one or more sample components of interest in the separation medium upon application of an applied stimulus.

In some embodiments, the device includes a solid support contacting a surface of the polymeric separation medium, where the device includes at least one channel through a portion of one or more of the polymeric separation medium and the solid support.

In some embodiments, the microwells are arranged as an array of microwells in the polymeric separation medium. In some embodiments, the microwells include an open end on the surface of the polymeric separation medium and an opposing closed end in the polymeric separation medium.

In some embodiments, the polymeric separation medium includes a central well having a plurality of microwells positioned on the periphery and in fluid communication with the central well. In some embodiments, each microwell includes an open end in fluid communication with the central well and an opposing closed end in the polymeric separation medium. In some embodiments, the microwells are arranged around substantially the entire periphery of the central well. In some embodiments, the device includes a solid support carrying the polymeric separation medium, where the device includes at least one channel through a portion of one or more of the polymeric separation medium and the solid support.

In some embodiments, the polymeric separation medium includes 100 or more microwells.

In some embodiments, the microwells are dimensioned to accommodate single cells.

In some embodiments, the open end of the microwell has a width greater than the closed end of the microwell.

In some embodiments, the applied stimulus is light.

Aspects of the present disclosure further include a method that includes contacting a sample with a polymeric separation medium having a plurality of microwells, and applying an electric field to the polymeric separation medium in a manner sufficient to move at least some components of the sample from the microwell into the polymeric separation medium to produce separated sample components in the polymeric separation medium. In some embodiments, the polymeric separation medium includes functional groups that covalently bond to one or more sample components of interest in the separation medium upon application of an applied stimulus.

In some embodiments, the sample includes cells and/or cellular components. In some embodiments, the method includes lysing the cells to produce the cellular components in the sample. In some embodiments, the method includes incubating the cells to produce the cellular components in the sample.

In some embodiments, the method includes immobilizing the separated sample components in the polymeric separation medium.

In some embodiments, the method includes detecting the separated sample components. In some embodiments, the detecting includes contacting the separated sample components with an analyte detection reagent. In some embodiments, the method includes contacting the separated sample components with a second analyte detection reagent.

In some embodiments, the method includes imaging the polymeric separation medium to produce an image of the separated cellular components.

Aspects of the present disclosure also include a kit. In some embodiments, the method includes a device as disclosed herein, and a packaging containing the device.

BRIEF DESCRIPTION OF THE FIGURES

FIG. 2b (bottom left) shows a graph of total fluorescence under the profile plots for βTUB in arbitrary fluorescence units (AFU) along with the running average of the number of cells-per-well (FIG. 2b (top left); tracking spatial variation in microwell occupancy and fluorescence readouts across the scWestern array. The running average window size was 30 blots. Well # was ordered by microwell block, moving from the left- to the right-hand side of the array. FIG. 2b (bottom right) shows histograms grouped by cells-per-well and fitted to a gamma distribution accounting for the kinetics of mRNA and protein production in the presence of cell division (a1's=14.8, a2's=23.0, a3's=28.6, b1's=1.6×105, b2's=b3's=1.8×105).

FIG. 2d (bottom) shows a graph where the limit of detection of 27,000 molecules was indicated by signal-to-noise ratio (SNR) analysis for EGFP calibration curves derived using direct and indirect methods (n=3 regions of interest per dot blot). Effective stripping performance was indicated for the indirect calibration slide after stripping and re-imaging for residual fluorescence signal.

FIG. 3a (top) shows fluorescence micrographs and line profiles for scWestern blots of single rat NSCs probed for ERK1/2 (ERK) and phospho-ERK1/2 (Thr202/Tyr204, pERK), against a βTUB and EGFP ladder (RFU: relative fluorescence units). FIG. 3a (bottom) shows similar micrographs for MEK1/2 and phospho-MEK1/2 (Ser217/Ser221). Primary antibody blots were probed using an Alexa Fluor 555-labeled secondary antibody (except EGFP; Alexa Fluor 488-) in the following order: pERK, ERK/EGFP co-probe, βTUB, pMEK, MEK; with stripping between each probing.

FIG. 4a (top) shows wide field fluorescence micrographs of cell types present in mixed differentiation cultures of rat neural stem cells at days 0 and 6 probed by conventional immunocytochemistry for stem cell markers (nestin, NEST; SOX2), and differentiation markers (βIII-tubulin, βIIITUB; glial fibrillary acidic protein, GFAP).

FIG. 5 (bottom) shows a molecular model of a reaction scheme of a light-activated covalent bonding reaction between the carbonyl functional groups of a benzophenone methacrylamide (BPMA) monomer and target polypeptide, according to embodiments of the present disclosure.

FIGS. 8a and 8b show a sketch of two calibration methods used to determine dynamic range and limit of detection in the single-cell immunoblotting assay. In FIG. 8a, direct calibration was performed by counting EGFP molecules in microwells prior to separation and capture. In FIG. 8b, indirect calibration was performed by inferring the number of EGFP molecules from a partitioning curve (see FIGS. 9a-c) constructed in a separate experiment in which the microwell and gel EGFP concentrations are inferred from fluorescence values taken at equilibrium.

FIG. 10a (top left) shows a log-transformed montage of a subset of microwells from blocks incubated with a range in purified EGFP concentrations, enclosed with a cover glass, and imaged for intrinsic EGFP fluorescence using wide field fluorescence microscopy. FIG. 10a (top right) shows a log-transformed probe fluorescence after separation, capture, and probing the same slide for EGFP (Alexa Fluor 555-labeled secondary antibody). FIG. 10a (bottom right) shows a calibration curve for EGFP in a separate microfluidic channel used to determine molecule numbers of EGFP in microwells (AFU: arbitrary fluorescence units; ROI: region of interest). FIG. 10a (bottom left) shows example microwells and immunoblots over the EGFP concentration range. FIG. 10b shows a scWestern slide incubated with purified EGFP concentrations achieving the indicated in-gel concentrations after adjustment for partitioning (FIG. 9b), spot exposure to UV, and probing for EGFP (Alexa Fluor 555-labeled secondary antibody). The slide was subsequently stripped and re-imaged under identical scanner settings.

FIG. 14a shows a log-linear plot of species molecular weight against migration distance in an 8% T scWestern gel for the fluorescently labeled species in FIG. 1d (x-axis error bars within point size (±SD, n=3 separations); Dronpa, 27 kDa; OVA, 45 kDa; BSA, 66 kDa; OVA', 90 kDa; BSA', 132 kDa). FIG. 14b shows a graph assuming consistent protein band widths (SD $\sigma_i$), plots of separation resolution $R_s=|x_1-x_2|/(2\sigma_1+2\sigma_2)$, where $x_i$ are migration distances, between band pairs were expected to be linear in the log ratio of their molecular weights. A linear fit of these data is shown, yielding a separable molecular weight difference of 51±1.6% (±SD, n=3 separations) for purified proteins separated from scWestern microwells upon substitution of $R_s=1$.

FIG. 17 shows single cell western blots of rat NSCs at anti-β-tubulin primary and Alexa Fluor 555-labeled secondary antibody dilutions of between 60× and 10×. Gains in absolute fluorescence signal above zero cell per well controls were observed for one and two cell-per-well blots across the dilution range.

FIG. 23a shows graphs of the relationship between skew and mean for pERK:ERK and pMEK:MEK distributions over the stimulation time course. Note CV and skewness are in percentage and dimensionless units, respectively, plotted on the same scale as fold fluorescence ratio data for convenience. FIG. 23b shows graphs of the fold-change in arbitrary fluorescence (linear units) for β-tubulin, ERK, and MEK show little variation across the cell populations at each stimulation time.

FIG. 34, Panel A, shows that the cells are injected into the central chamber. FIG. 34, Panel B, shows that the device is spun on an upright spinner to position the cells into the traps. FIG. 34, Panel C, shows that a combination lysis-electrophoresis buffer is injected into the chamber. Electrosmotic flow during electrophoresis moves the buffer to cells for lysis. FIG. 34, Panel D, shows that proteins are separated and immobilized with UV exposure, and labeled antibodies are used to determine proteins of interest.

FIG. 36A shows an image of green fluorescent protein (GFP) initially accumulated in the wells when exposed to a low electric field (50 V). FIG. 36B shows an image of GFP, which has moved through the PAG at higher voltages (200 V) to facilitate protein separations.

DETAILED DESCRIPTION

Figure 1:
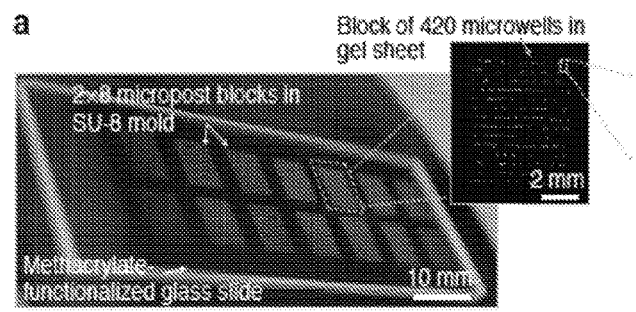
FIG. 1a shows an image and drawings of a single-cell Western (scWestern) blotting assay according to embodiments of the present disclosure.
FIG. 1b shows a process flow schematic where an open-gel scWestern blotting was performed as a 4 hr multi-stage assay that included: cell settling, chemical lysis with a modified RIPA buffer, PAGE (E: electric field), UV protein immobilization (hv: photon energy) onto a photoactive capture gel with tunable porosity (PACTgel), and diffusion driven antibody probing (e.g., primary and fluorescently labeled secondary antibody probes, 1° Ab and 2° Ab*), according to embodiments of the present disclosure.
FIG. 1c shows a wide-field micrograph of 15 μm fluorescent beads and confocal micrograph of a live EGFP-expressing rat neural stem cell (NSC) settled in rhodamine-PA gels (GEL), according to embodiments of the present disclosure.
FIG. 1d shows an image of PAGE-resolved 5 fluorescently labeled proteins in a 550 μm separation distance (DRO, dronpa 27 kDa; OVA, ovalbumin 45 kDa; BSA, bovine serum albumin 66 kDa; OVA', OVA dimer 90 kDa; BSA', BSA dimer 132 kDa), according to embodiments of the present disclosure.
FIG. 1e shows a scWestern analysis of EGFP and β-tubulin (βTUB) from a single rat NSC (RFU: relative fluorescence units), according to embodiments of the present disclosure.
Figure 1:
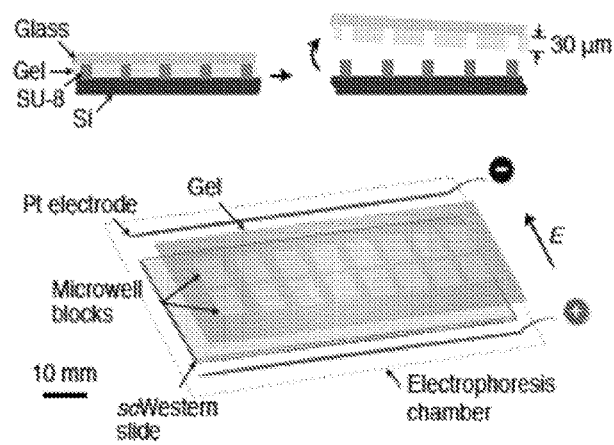
Figure 1:
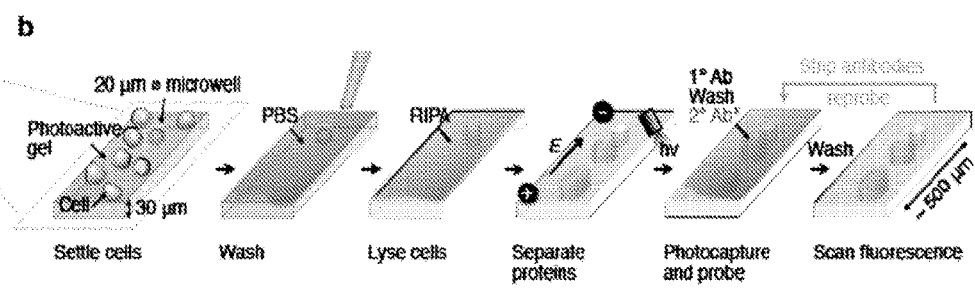

Electrophoretic separation devices and methods for using the same are provided. Aspects of embodiments of the present disclosure include a device that includes a polymeric separation medium having a plurality of microwells. The polymeric separation medium includes functional groups that covalently bond to one or more sample components of interest in the separation medium upon application of an applied stimulus.

Below, the subject electrophoretic separation devices are described first in greater detail. Methods of detecting one or more analytes in a sample are also disclosed in which the subject devices find use. In addition, systems and kits that include the subject devices are also described.

Devices

Embodiments of the present disclosure include separation devices. In certain embodiments, the separation devices are configured to separate analytes in a sample. For example, the separation devices may be configured to separate analytes in a sample based on one or more physical and/or chemical properties of the analytes. In some instances, the analytes may include detectable differences in their molecular weight, size, charge (e.g., mass to charge ratio), isoelectric point, affinity interactions, and the like. Separation devices of the present disclosure may be configured to distinguish different analytes from each other based on one or more of their molecular weight, size, charge (e.g., mass to charge ratio), isoelectric point, affinity interactions, and the like.

In certain embodiments, the separation devices are microfluidic separation devices. A "microfluidic device" is device that is configured to control and manipulate fluids geometrically constrained to a small scale (e.g., sub-millimeter). Embodiments of the microfluidic devices include a polymeric medium, e.g., a polymeric separation medium as described in more detail herein. The polymeric medium may include a covalently bound capture member that specifically binds to an analyte of interest in a sample.

In certain embodiments, the separation device includes a solid support. The solid support may be configured to support a polymeric medium (e.g., the polymeric separation medium). For example, the polymeric separation medium may be provided on the solid support, such that at least a portion of the polymeric separation medium is in contact with a surface of the solid support (e.g., the device includes a solid support carrying the polymeric medium). In some cases, the solid support is composed of a material that is inert (e.g., does not degrade or react) with respect to the samples, buffers, reagents, etc. used in the subject devices and methods. For instance, the solid support may be made of a material, such as, but not limited to, glass, quartz, polymers, elastomers, paper, combinations thereof, and the like. In certain embodiments, the solid support is substantially transparent. By "transparent" is meant that a substance allows visible light to pass through the substance. In some embodiments, a transparent solid support facilitates detection of analytes bound to the polymeric medium, for example analytes that include, produce, or are labeled with a detectable label, such as a fluorescent label. In some cases, the solid support is substantially opaque. By "opaque" is meant that a substance substantially blocks visible light from passing through the substance. In certain instances, an opaque solid support may facilitate the analysis of analytes that are sensitive to light, such as analytes that react or degrade in the presence of light.

In certain embodiments, the solid support is sized to accommodate the polymeric separation medium. For example the solid support may have dimensions (e.g., length and width) such that the entire polymeric separation medium is supported by the solid support. In some cases, the solid support may have dimensions (e.g., length and width) larger than the polymeric separation medium. In some instances, the solid support has dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less. In some cases, the solid support has a thickness ranging from 0.5 mm to 5 mm, or 1 mm to 4 mm, of 1 mm to 3 mm, or 1 mm to 2 mm. In certain instances, the solid support has a thickness of 1 mm.

As described above, the solid support may be configured to support a polymeric separation medium. Aspects of the polymeric separation medium are described in more detail below.

Polymeric Separation Medium

The polymeric separation medium may be configured to separate constituents of a sample from each other. In some cases, the separation medium is configured to separate constituents in a sample based on the physical properties of the constituents. For example, the separation medium may be configured to separate the constituents in the sample based on the molecular mass, size, charge (e.g., charge to mass ratio), isoelectric point, affinity interactions, etc. of the constituents.

In certain instances, the separation medium is configured to separate the constituents in the sample based on the size and charge of the constituents. The separation medium may be configured to separate the constituents in the sample into distinct detectable bands of constituents. By "band" is meant a distinct detectable region where the concentration of a constituent is significantly higher than the surrounding regions. Each band of constituent may include a single constituent or several constituents, where each constituent in a single band of constituents has substantially similar physical properties, as described above.

In certain embodiments, the separation medium is configured to separate the constituents in a sample as the sample traverses the separation medium. In some cases, the separation medium is configured to separate the constituents in the sample as the sample flows through the separation medium. Aspects of the separation medium include that the separation medium has a directional separation axis, or in other cases a plurality of directional separation axes, as described in more detail below. In some instances, the directional separation axis is oriented in the direction the sample travels as the sample traverses the separation medium.

Polymeric Separation Medium with a Planar Array of Microwells

In certain embodiments, the polymeric separation medium includes a planar array of microwells. In these embodiments, the directional separation axis is aligned with the length (or the width) of the separation medium. For instance, the directional separation axis may be substantially parallel to the length (or the width) of the separation medium. In some embodiments, the separation medium is square or rectangular in shape and the directional axis of the separation medium may be aligned with the length (or width) of the separation medium. In these embodiments, the sample traverses the separation medium along its length (or width). In some cases, where the sample traverses the length of the separation medium, the length of the separation medium is greater than the width of the separation medium, such as 2 times, 3 times, 4 times, 5 times, 10 times, 25 times, 50 times, 75 times, 100 times, 125 times, 150 times, 175 times, or 200 times or more the width of the separation medium. In some instances, a longer separation axis may facilitate an increase in resolution between bands of different analytes in the sample.

In certain embodiments, the separation medium includes a plurality of microwells in the separation medium. In some instances, the separation medium includes a substantially planar array of microwells in the separation medium. An "array of microwells" includes any two-dimensional or substantially two-dimensional arrangement of microwells. For example, a planar array of microwells may be arranged into rows and columns of microwells. The microwells in the planar array of microwells may be individually addressable. A microwell is "addressable" when the array includes multiple microwells positioned at particular predetermined locations (e.g., "addresses") in the array. Microwells may be separated by intervening spaces. A planar array of microwells may include one or more, including two or more, four or more, eight or more, 10 or more, 25 or more, 50 or more, 100 or more, 200 or more, 300 or more, 400 or more, 500 or more, 750 or more, 1000 or more, 1500 or more, 2000 or more, 2500 or more, 3000 or more, 3500 or more, 4000 or more, 4500 or more, 5000 or more, 5500 or more, 6000 or more, 6500 or more, 7000 or more, 7500 or more, 8000 or more, 8500 or more, 9000 or more, 9500 or more, 10,000 or more, or 25,000 or more, or 50,000 or more, or 75,000 or more, or 100,000 or more microwells in a polymeric separation medium. In some cases, a planar array of microwells may include 5000 or more microwells. Each polymeric separation medium may include one or more arrays of microwells, for example, 1 or more, 2 or more, 3 or more, 4 or more, 5 or more, 6 or more, 7 or more, 8 or more, 9 or more, 10 or more, 12 or more, 14 or more, 16 or more, 18 or more, 20 or more, 25 or more, 30 or more, 35 or more, 40 or more, 45 or more, 50 or more, 75 or more, or 100 or more arrays or microwells. In some cases, the polymeric separation medium includes 10 or more arrays of microwells. Depending upon the use, any or all of the microwells may be the same or different from one another and each may be configured to contain distinct samples or sample constituents. Aspects of individual microwells are described in more detail below, but may be applied to any or all of the microwells in the array of microwells.

In certain embodiments, the polymeric separation medium includes a planar array of microwells as described above. The planar array of microwells may be arranged such that each microwell has an open end provided on a surface of the separation medium (e.g., on a top surface of the separation medium). In these embodiments, the interior volume of each microwell may extend from the open end of the microwell on the surface of the polymeric separation medium into the polymeric separation medium. In certain embodiments, the open end of the microwell (and thus the interior volume of the microwell) is in fluid communication with a fluid provided on the surface of the separation medium (e.g., buffer, sample, etc.). In some instances, the bottom (i.e., closed end) of the microwell is formed by the solid support supporting the polymeric separation medium, e.g., in embodiments where the interior volume of the microwell extends all the way through the separation medium, such as where the depth of the microwell equals the thickness of the polymeric separation medium. In other instances, the bottom (i.e., closed end) of the microwell is formed by the polymeric separation medium, e.g., in embodiments where the interior volume of the microwell does not extend all the way through the separation medium, such as where the depth of the microwell is less than the thickness of the polymeric separation medium.

In certain embodiments, the microwell is configured such that an axis of the microwell from the closed end to the open end of the microwell is substantially perpendicular to the surface of the separation medium (e.g., the surface of the separation medium having the open ends of the microwells). In certain embodiments, the walls (e.g., the side walls) of the microwell are formed by the polymeric separation medium, such as where the interior volume of the microwell extends into the polymeric separation medium and is surrounded by the polymeric separation medium.

An example of a planar array of microwells in a polymeric separation medium is shown in FIG. 1a, which is an image of a solid support carrying a polymeric separation medium that includes 16 arrays of 420 microwells in each array, for a total of 6,720 microwells. The polymeric separation medium shown in FIG. 1a was formed using a mold that included micropost blocks. As described in more detail in Example 1 below, removal of the micropost mold from the polymeric separation medium resulted in a polymeric separation medium with an array of microwells as shown.

Polymeric Separation Medium with a Circular Arrangement of Microwells

In other embodiments, rather than being arranged as a planar array of microwells, the separation medium includes a circular arrangement of microwells. For example, the separation medium may include a circular arrangement of microwells that have a plurality of radially oriented separation axes. Each microwell in the circular arrangement of microwells may be associated with its own radially oriented separation axis. In these embodiments, the radial separation axes may be arranged such that a sample traverses the separation medium from a central well in the separation medium towards the periphery of the separation medium in directions extending radially away from the central well through the separation medium.

For example, in certain embodiments, the device includes a polymeric separation medium having a central well. In some instances, the central well is positioned in the polymeric separation medium, such that the central well forms a void in the polymeric separation medium. In certain embodiments, the peripheral walls of the central well are formed by the polymeric separation medium. For example, the polymeric separation medium may include a void where the polymeric separation medium surrounding the void forms the peripheral walls of the central well. In some cases, the central well is substantially circular in shape. In some instances, the separation medium is configured such that a sample is placed in the central well of the separation medium.

In certain embodiments, the central well of the polymeric separation medium includes a plurality of microwells positioned on the periphery and in fluid communication with the central well. Microwells in fluid communication with the central well may have an open end that faces the interior volume of the central well, such that a fluid and constituents thereof may flow from the interior volume of the central well to the interior volume of the microwells and vice versa. In some embodiments, each microwell has a closed end opposite from the open end of the microwell. In certain cases, the closed ends of the microwells are formed by the surrounding polymeric separation medium. In certain instances, the microwells are coplanar with the central well. For example, the microwells may be configured such that an axis of the microwell from the closed end to the open end of the microwell is coplanar with a transverse (i.e., horizontal) radius of the central well (e.g., similar to spokes in a wheel). As such, the microwells may have an axis of the microwell from the closed end to the open end of the microwell that is coplanar with the polymeric separation medium.

In certain embodiments, the microwells are arranged around the periphery of the central well as described above. In some cases, the microwells are arranged around substantially the entire periphery of the central well. In certain embodiments, the microwells are arranged around a portion of the periphery of the central well, such as 90% of the periphery of the central well, or 80%, or 70%, or 60%, or 50%, or 40%, or 30%, or 20%, or 10% of the periphery of the central well. In some instances, the peripheral surface of the central well that includes the microwells includes multiple microwells, e.g., 25 or more, 50 or more, 75 or more, 100 or more, 150 or more, 200 or more, 300 or more, 400 or more, 500 or more, 600 or more, 700 or more, 800 or more, 900 or more, 1000 or more, 1250 or more, 1500 or more 1750 or more, 2000 or more, 2500 or more, 3000 or more, 3500 or more, 4000 or more, 4500 or more, or 5000 or more microwells.

In some embodiments, a microwell is separated a certain distance from an adjacent microwell. For example, a microwell may be separated from an adjacent microwell by a distance of 500 µm or less, such as 450 µm or less, or 400 µm or less, or 350 µm or less, or 300 µm or less, or 250 µm or less, or 200 µm or less, or 150 µm or less, or 100 µm or less, such as 90 µm or less, or 80 µm or less, or 70 µm or less, or 60 µm or less, or 50 µm or less, or 40 µm or less, or 30 µm or less, or 20 µm or less, or 10 µm or less. In some cases, a microwell may be separated from an adjacent microwell by a distance of 10 µm to 100 µm, such as 10 µm to 90 µm, or 10 µm to 80 µm, or 10 µm to 70 µm, or 10 µm to 60 µm, or 20 µm to 60 µm, or 30 µm to 60 µm, or 40 µm to 60 µm.

In certain embodiments, the device includes a cover. In some cases, the cover may be disposed on the polymeric separation medium, such that the polymeric separation medium is positioned between the support and the cover. In certain embodiments, the cover includes a reservoir well configured to be in fluid communication with the central well. For example, the reservoir well may have an interior volume in fluid communication with the interior volume of the central well. In some instances, the reservoir well is formed in a polymeric medium on a surface of the cover (e.g., a bottom surface of the cover). In some instances, the reservoir well is positioned in a polymeric medium, such that the reservoir well forms a void in the polymeric medium. In certain embodiments, the peripheral walls of the reservoir well are formed by the polymeric medium. For example, the polymeric medium may include a void where the polymeric medium surrounding the void forms the peripheral walls of the reservoir well. In some cases, the reservoir well is substantially circular in shape.

In certain embodiments, the polymeric medium that forms the reservoir well is disposed on the cover. As such, the top of the reservoir well may be formed by a surface of the cover (e.g., the bottom surface of the cover). In some instances, the peripheral walls of the reservoir well extend substantially vertically down from the bottom surface of the cover. Embodiments of the cover may be made of any suitable material that is compatible with the subject devices and compatible with the samples, buffers, reagents, etc. used in the subject devices. In some cases, the cover is made of a material that is inert (e.g., does not degrade or react) with respect to the samples, buffers, reagents, etc. used in the subject devices and methods. For instance, the cover may be made of materials, such as, but not limited to, glass, quartz, polymers, elastomers, paper, combinations thereof, and the like. In certain embodiments, the reservoir well does not include microwells on the periphery of the reservoir well.

In certain embodiments, the diameter of the reservoir well is less than the diameter of the central well. In some cases, the diameter of the central well is 50 mm or less, such as 40 mm or less, or 30 mm or less, or 20 mm or less, or 15 mm or less, or 10 mm or less. In certain instances, the diameter of the central well is 12 mm. In some cases, the diameter of the reservoir well is 40 mm or less, such as 30 mm or less, or 20 mm or less, or 15 mm or less, or 10 mm or less, or 5 mm or less. In certain instances, the diameter of the reservoir well is 8 mm.

In certain embodiments, the device includes a solid support with a polymeric separation medium having a central well and a cover having a polymeric medium with a reservoir well as described above. The device may be configured such that the cover is applied to the solid support such that the polymeric separation medium of the solid support and the polymeric medium of the cover at in contact with each other. In these instances, the central well and the reservoir well may be in fluid communication with each other such that they form an enclosed space that includes the interior volumes of both the central well and the reservoir well. In some instances, the cover may include a fluid inlet that is in fluid communication with the reservoir well (and thus in fluid communication with the central well).

Figure 32:
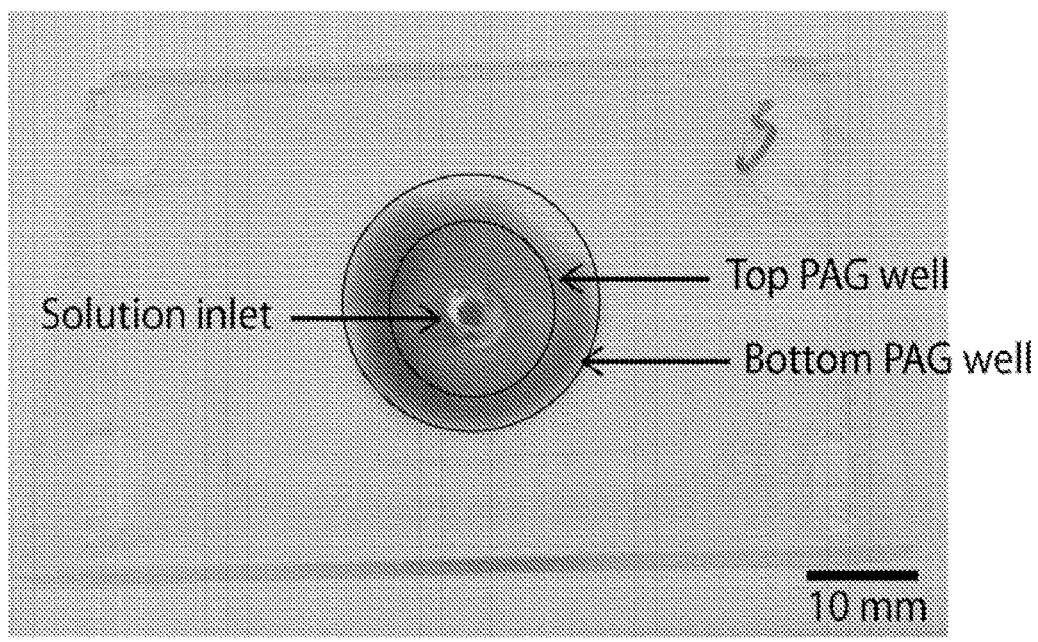
FIG. 32 shows a separation device according to embodiments of the present disclosure.
Figure 33:
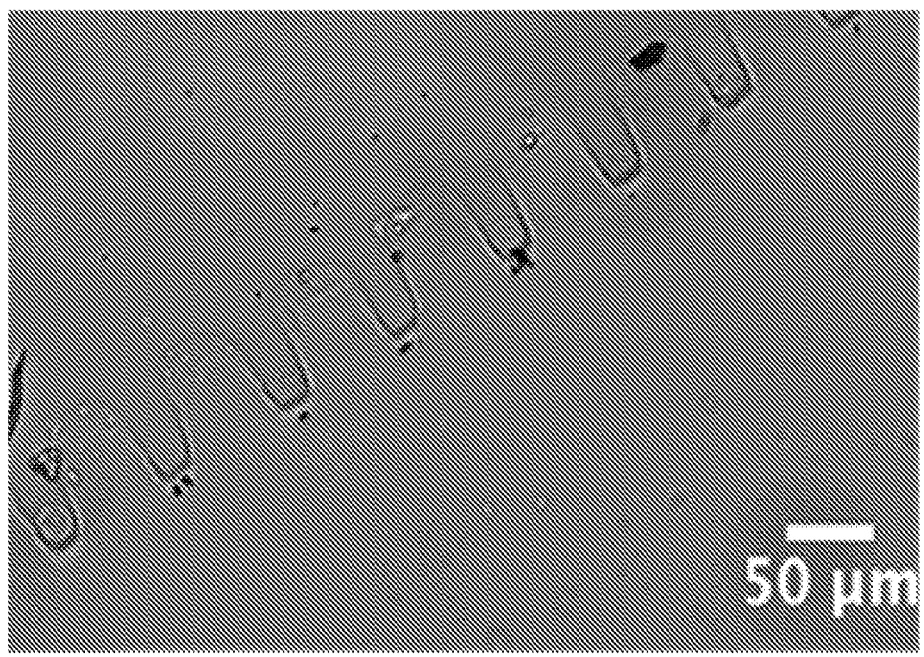
FIG. 33 shows an image of cells trapped in microwells of a device according to embodiments of the present disclosure.

An example of a polymeric separation medium that includes a circular arrangement of microwells is shown in FIG. 32, which is an image of a device that includes a solid support carrying a polymeric separation medium (e.g., polyacrylamide gel, PAG) with a central (bottom) well and a cover that includes a polymeric medium (e.g., polyacrylamide gel, PAG) with a reservoir (top) well. The reservoir well includes a solution inlet in fluid communication with the reservoir well (and thus also in fluid communication with the central well). The central well includes microwells arranged around the periphery of the central well (FIG. 33).

Additional Aspects of Microwells

In certain embodiments, the microwell has an interior volume with a defined shape. For example, the interior volume of the microwell may have a shape of a cylinder, a cube, a rectangular cuboid, a frustum (e.g., a square frustum, a rectangular frustum, a conical frustum, etc.), and the like.

In certain embodiments, the open end of the microwell has dimensions greater than the closed end of the microwell. For instance, the open end of the microwell may have dimensions (e.g., width and/or length, or diameter, depending on the shape of the microwell) that are 1.1 times greater than the dimensions of the closed end of the microwell, such as 1.2 times, or 1.3 times, or 1.4 times, or 1.5 times, or 1.6 times, or 1.7 times, or 1.8 times, or 1.9 times, or 2 times the dimensions of the closed end of the microwell.

A "microwell" is a well that has dimensions in the micrometer scale. While the dimensions may vary, in some instances, the open end of the microwell has a width of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less. For example, the open end of the microwell may have a width ranging from 10 µm to 100 µm, such as 10 µm to 90 µm, or 10 µm to 80 µm, or 10 µm to 70 µm, or 10 µm to 60 µm, or 10 µm to 50 µm, or 10 µm to 40 µm, or 10 µm to 30 µm. In certain embodiments, the microwell may have an open end dimensioned to accommodate a single cell in the microwell.

In some cases, the closed end of the microwell has a width of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less. For example, the closed end of the microwell may have a width ranging from 10 µm to 100 µm, such as 10 µm to 90 µm, or 10 µm to 80 µm, or 10 µm to 70 µm, or 10 µm to 60 µm, or 10 µm to 50 µm, or 10 µm to 40 µm, or 10 µm to 30 µm, or 10 µm to 20 µm. In certain embodiments, the microwell may have a closed end dimensioned to accommodate a single cell in the microwell.

In certain embodiments, the microwell has a depth (e.g., the distance from the open end to the closed end of the microwell) of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less. For example, the microwell may have a depth ranging from 10 µm to 100 µm, such as 10 µm to 90 µm, or 10 µm to 80 µm, or 10 µm to 70 µm, or 10 µm to 60 µm, or 20 µm to 60 µm, or 30 µm to 60 µm, or 40 µm to 60 µm. In certain embodiments, the microwell may have a depth dimensioned to accommodate a single cell in the microwell.

The microwells in the polymeric separation medium may be substantially uniform. For example, the shape and size of the microwells in the separation medium may be substantially uniform. In other embodiments, the microwells may be different, such as having a different shape, a different size, combinations thereof, and the like. A separation medium that includes different microwells may facilitate the analysis of different sample constituents at the same time. For instance, microwells that have different shapes and/or sizes may preferentially capture different shaped or sized sample components (e.g., different shaped or sized cells in the sample).

Additional Aspects of the Separation Medium

In certain embodiments, the separation medium includes a polymer, such as a polymeric gel. The polymeric gel may be a gel suitable for gel electrophoresis. The polymeric gel may include, but is not limited to, a polyacrylamide gel (e.g., methacrylamide gel), an agarose gel, and the like. The resolution of the separation medium may depend on various factors, such as, but not limited to, pore size, total polymer content (e.g., total acrylamide content), concentration of cross-linker, applied electric field, assay time, and the like. For instance, the resolution of the separation medium may depend on the pore size of the separation medium. In some cases, the pore size depends on the total polymer content of the separation medium and/or the concentration of cross-linker in the separation medium. In certain instances, the separation medium is configured to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a total acrylamide content, T (T=total concentration of acrylamide and bisacrylamide monomer, % w/v), ranging from 1% to 20%, such as from 3% to 15%, including from 5% to 10%. In some instances, the separation medium has a total acrylamide content of 7%. In certain cases, the separation medium has a total acrylamide content of 6%. In certain embodiments, the separation medium includes a polyacrylamide gel that has a crosslinker content, C (% w/v), ranging from 1% to 10%, such as from 2% to 7%, including from 2% to 5%. In some instances, the separation medium has a total crosslinker content of 3%.

In certain embodiments, the separation medium is configured to be formed from precursor moieties. For example, the separation medium may be a gel (e.g., a polyacrylamide gel) formed form gel precursors (e.g., polyacrylamide gel precursors, such as polyacrylamide gel monomers). The precursor moieties may be configured to react to form the separation medium. For instance, the gel precursors may be configured to react with each other to form the polyacrylamide gel separation medium. The reaction between the gel precursors may be activated by any suitable protocol, such as, but not limited to, chemical activation, light activation, etc. In some embodiments, the gel precursors are configured to be activated chemically, for example by contacting the gel precursors with an activation agent, such as, but not limited to, a peroxide. In some embodiments, the gel precursors are configured to be activated by light (i.e., photo-activated), for instance by contacting the gel precursors with light. The light may be of any wavelength suitable for activating the formation of the separation medium, and in some instances may have a wavelength associated with blue light in the visible spectrum. For example, the light used to activate formation of the separation medium may have a wavelength ranging from 400 nm to 500 nm, such as from 410 nm to 490 nm, including from 420 nm to 480 nm, or from 430 nm to 480 nm, or from 440 nm to 480 nm, or from 450 nm to 480 nm, or from 460 nm to 480 nm, or from 465 nm to 475 nm. In certain cases, the light used to activate formation of the separation medium has a wavelength ranging from 465 to 475 nm. In some instances, the light used to activate formation of the separation medium has a wavelength of 470 nm.

In some instances, the separation medium has dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less. In some cases, the separation medium has a thickness ranging from 1 µm to 100 µm, such as from 10 µm to 75 µm, or from 10 µm to 50 µm, or from 20 µm to 50 µm. In some cases, the separation medium has a thickness of 30 µm.

In certain embodiments, the separation medium includes a buffer. The buffer may be any convenient buffer used for gel electrophoresis. In certain embodiments, the buffer is a Tris buffer. In certain embodiments, the separation medium includes a buffer, such as a Tris-glycine buffer. For example, the buffer may include a mixture of Tris and glycine.

In some cases, the buffer includes a detergent. In certain instances, the detergent is configured to provide analytes in the sample with substantially similar charge-to-mass ratios. Analytes with substantially similar charge-to-mass ratios may facilitate the separation of the analytes into one or more bands in the separation medium based on the molecular masses of the analytes in the sample. In certain cases, the detergent is anionic detergent configured to provide analytes in the sample with a charge, such as a negative charge. For example, the detergent may be an anionic detergent, such as, but not limited to, sodium dodecyl sulfate (SDS).

In certain embodiments, the separation medium is configured to separate the constituents in the sample based on the isoelectric point (pI) of the constituents (e.g., isoelectric focusing, IEF). In some cases, the separation medium includes a polymeric gel as described above. For example, the polymeric gel may include a polyacrylamide gel, an agarose gel, and the like. In certain instances, the polymeric gel includes a pH gradient, which, in some embodiments, is co-polymerized with the polymeric gel. In embodiments where the pH gradient is co-polymerized with the polymeric gel, the pH gradient may be substantially immobilized resulting in a separation medium having an immobilized pH gradient. In certain instances, the pH gradient includes a weak acid or a weak base (e.g., Immobilines), ampholytes, or the like.

In certain embodiments, the separation medium is configured to separate constituents in a sample based on size. For example, in some cases, the separation medium includes a polymeric gel having a pore size gradient. The pore size gradient may decrease along the directional axis of the separation medium. For example, the pore size gradient may have a pore size that decreases along the directional axis of the separation medium, such that a sample traversing the separation medium encounters progressively smaller and smaller pore sizes in the separation medium. As constituents in the sample traverse the pore size gradient, the constituents in the sample may be separated based on size. For example, larger constituents in the sample may be retained in the separation medium more readily than smaller constituents, which are able to traverse greater distances through the decreasing pore size gradient.

In some cases, the pore size of the separation medium depends on the total polymer content of the separation medium and/or the concentration of crosslinker in the separation medium. In certain instances, the separation medium pore size sufficient to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a pore size that depends on the total acrylamide content, T (T=total concentration of acrylamide and bisacrylamide monomer), where the total acrylamide content, T, ranges from 1% to 20%, such as from 3% to 15%, including from 5% to 10%. In some instances, the separation medium has pore size defined by a total acrylamide content of 7%. In certain cases, the separation medium has a pore size defined by a total acrylamide content of 6%. In certain embodiments, the separation medium includes a polyacrylamide gel that has a crosslinker content, C (% w/v), ranging from 1% to 10%, such as from 2% to 7%, including from 2% to 5%. In some instances, the separation medium has a total crosslinker content of 3%.

In certain embodiments, the separation medium is configured to covalently bond to the constituents of interest. The covalent bond may be formed upon application of an applied stimulus. For example, the applied stimulus may include electromagnetic radiation, such as light. In some cases, the light is ultraviolet (UV) light. In some instances, the light used to covalently bond the constituents of interest to the separation medium has a wavelength ranging from 10 nm to 400 nm, such as from 50 nm to 400 nm, including from 100 nm to 400 nm, or from 150 nm to 400 nm, or from 200 nm to 400 nm, or from 250 nm to 400 nm, or from 300 nm to 400 nm, or form 325 nm to 375 nm, or from 350 nm to 365 nm. In certain cases, the light has a wavelength ranging from 350 to 365 nm.

In certain embodiments, the light used to covalently bond the constituents of interest to the separation medium has a wavelength different from the light used to activate formation of the separation medium. For example, as described above, the light used to activate formation of the separation medium may have a wavelength of blue light in the visible spectrum. As described above, the light used to covalently bond the constituents of interest to the separation medium may have a wavelength of UV light. As such, in certain embodiments, the separation medium is configured to be formed upon application of a first wavelength of light, and configured to covalently bond the constituents of interest upon application of a second wavelength of light. The first and second wavelengths of light may be blue light and UV light, respectively, as described above.

In some cases, the separation medium includes functional groups that covalently bond to the one or more constituents of interest. For example, the constituents of interest may be an analyte of interest, such as, but not limited to, a protein, a peptide, and the like. The functional groups may include functional groups that are activated upon application of an applied stimulus, such as electromagnetic radiation (e.g., light) as described above. As such, in certain instances, the functional groups are light-activatable functional groups. Upon application of light, the light-activatable functional groups may form a reactive species capable of forming covalent bonds, such as a radical alkyl intermediate. Examples of functional groups that may covalently bond to the constituents of interest upon application of an applied stimulus (e.g., light) include, but are not limited to, benzophenone groups, and the like. Once activated by the applied stimulus, the functional group may bond to the constituent of interest (e.g., protein or peptide) forming a covalent bond between the separation medium and the constituent of interest. For example, the functional group may form a carbon-carbon bond between the functional group and the constituent of interest.

In some embodiments, the functional groups are co-polymerized with the separation medium. For example, the functional groups may include a linker group that is attached to the separation medium. The functional group may be bound to the linker group at a first end of the linker group, and a second end of the linker group may be bound to the separation medium, thereby indirectly bonding the functional group to the separation medium. In some instances, the second end of the linker group, which is bound to the separation medium, includes a co-monomer, such as, but not limited to, an acrylamide co-monomer, and the like. In some embodiments, the second end of the linker group includes a methacrylamide co-monomer. In certain cases, the functional group is a benzophenone functional group and the linker group includes a co-monomer, such as an acrylamide co-monomer. For example, the functional group (including the linker group) may be N-(3-[(4-benzoylphenyl)formamido]propyl) methacrylamide (also known as BPMA or BPMAC). As described above, the linker group may have a first end bound to the functional group, and a second end bound to the separation medium. In some instances, the middle portion of the linker group between the first and second ends includes an aliphatic group, such as, but not limited to, a $C_1$-$C_{10}$ alkyl group. In certain cases, the middle portion of the linker group includes a lower alkyl group (e.g., a $C_1$-$C_6$ alkyl group). For instance, the middle portion of the linker group may include a propyl group.

Figure 5:
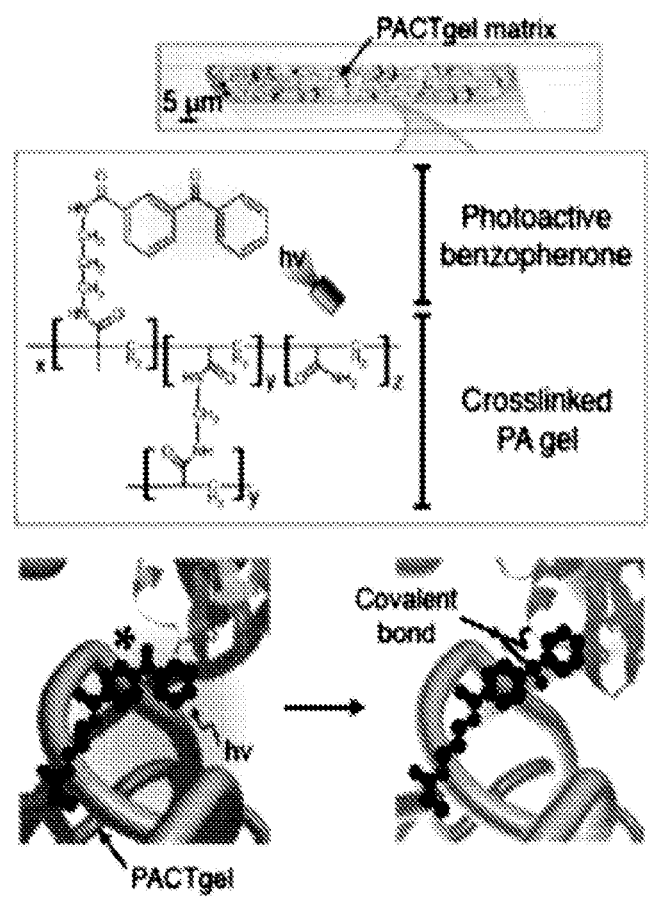
FIG. 5 (top) shows a light-activated benzophenone functionalized polyacrylamide gel, where a covalent bonding reaction between the carbonyl functional groups of the benzophenone methacrylamide (BPMA) monomer and target polypeptide may occur upon the application of a light stimulus, according to embodiments of the present disclosure.

An embodiment of the functional groups that may be co-polymerized with the separation medium is shown in FIG. 5, which shows a cross-linked polyacrylamide gel separation medium that includes photoactive benzophenone functional groups. The photoactive benzophenone groups may be activated by light to form covalent bonds to constituents of interest (e.g., proteins in the separated sample).

In certain embodiments, the separation medium is configured to bind to constituents in a sample at a minimum capture efficiency. The capture efficiency is the percentage of constituents in the sample that are bound by the separation medium. In some instances, the capture efficiency, q, is the ratio of fluorescence measured after gradient washout ($AFU_w$) to the fluorescence during focusing ($AFU_f$), corrected by a factor ε to account for the anticipated influence of pH on the species fluorescence signal. In certain embodiments, the separation medium is configured to have a capture efficiency of 1% or more, such as 5% or more, including 10% or more, or 20% or more, or 30% or more, or 40% or more, or 50% or more, or 60% or more, or 70% or more, or 80% or more, or 90% or more, or 95% or more. In some instances, the separation medium has a capture efficiency of 75% or more.

Additional aspects of the polymeric separation medium are described in U.S. Application Publication No. 2011/0177618, filed May 18, 2010, and U.S. Application Publication No. 2012/0329040, filed Jun. 21, 2012, the disclosures of each of which are incorporated herein by reference.

Additional Aspects of the Device

In certain embodiments, the device includes a channel through a portion of one or more of the polymeric separation medium and a solid support contacting a surface of the polymeric separation medium. In some instances, one or more walls or ends of the channel are in fluid communication with the polymeric separation medium. In certain cases, a channel that has one or more walls or ends of the channel in fluid communication with the polymeric separation medium facilitates the delivery of the contents of the channel (e.g., a buffer, a solution, a reagent, such as an analyte detection reagent, etc.) to one or more regions of the polymeric separation medium. In some instances, delivery of substances to one or more specific regions of the polymeric separation medium increases efficiency by facilitating a reduction in the amount of consumable substances used during an assay protocol. For instance, delivery of an analyte detection reagent through a channel to a predetermined region of the polymeric separation medium may facilitate a reduction in the amount of analyte detection reagent used as compared to an assay protocol where the entire polymeric separation medium is contacted with the analyte detection reagent.

In certain embodiments, the channel may be positioned such that it passes through a portion of the polymeric separation medium. In some embodiments, one or more walls of the channel may be formed by the polymeric separation medium. For example, the channel may be provided in a surface of the polymeric separation medium, such that the channel forms an elongated void in the surface of the polymeric separation medium. In these embodiments, the polymeric separation medium forms the side walls and bottom of the channel. In some instances, one side of the channel (e.g., the top) is open. In other embodiments, the channel passes through a central portion of the polymeric separation medium, such that the channel forms a void surrounded by the polymeric separation medium. In these embodiments, the walls of the channel are formed by the polymeric separation medium. In certain embodiments, the channel is positioned such that the channel is coplanar with the polymeric separation medium.

In some instances, the channel is positioned such that it passes through a portion of the solid support carrying the separation medium. In some embodiments, one or more walls of the channel may be formed by the solid support. For example, the channel may be provided in a surface of the solid support, such that the channel forms an elongated void in the surface of the solid support. In these embodiments, the solid support forms the side walls and bottom of the channel. In some instances, one side of the channel (e.g., the top) is open such that the interior volume of the channel is exposed (e.g., exposed to an overlying polymeric separation medium). In other embodiments, the channel passes through a central portion of the solid support, such that the channel forms a void surrounded by the solid support. In these embodiments, the walls of the channel are formed by the solid support. In certain embodiments, the channel is positioned such that the channel is coplanar with the solid support. In certain embodiments, the solid support is a support with the polymeric separation medium disposed on a surface thereof. In certain instances, one or more channels are provided in the support as described above. In some embodiments, the solid support is a cover disposed on a surface of the polymeric separation medium. In certain instances, one or more channels are provided in the cover as described above. In certain embodiments, the channels may be provided in both the support and the cover.

In certain embodiments, the channel is positioned such that the channel is not coplanar with the polymeric separation medium. For example, the channel may be positioned at an angle relative to the plane of the polymeric separation medium. In some embodiments, the channel is positioned such that the channel is not coplanar with the solid support carrying the polymeric separation medium. For example, the channel may be positioned at an angle relative to the plane of the solid support. In these embodiments, the channel may pass through a portion of the polymeric separation medium and a portion of the solid support.

The channel may be in fluid communication with an input reservoir at a first end (e.g., an upstream end). The input reservoir may contain a buffer, a solution, a reagent, etc. that may be provided to the separation medium during one or more steps in an assay. In some cases, the opposing end of the channel (e.g., the downstream end) may be in fluid communication with an output reservoir. In other embodiments, the downstream end of the channel may be a closed end, such that the contents of the channel may be delivered to the closed end of the channel. For example, the closed end of the channel may be in contact with a portion of the polymeric separation medium, such that the contents of the channel are delivered to that portion of the polymeric separation medium.

In certain embodiments, the device includes one or more channels. For example, the device may include 1 channel, or 2 or more channels, such as 3 or more, 4 or more, 5 or more, 6 or more, 7 or more, 8 or more, 9 or more, 10 or more, 12 or more, 14 or more, 16 or more, 18 or more, 20 or more, 25 or more, 30 or more, 35 or more, 40 or more, 45 or more, 50 or more, 75 or more, or 100 or more channels. The channels may be individual channels. In these embodiments, individual channels may be provided for delivery of a substance to different predetermined portions of the polymeric separation medium. In some embodiments, two or more channels may be in fluid communication with each other. For instance, the interior volumes of two or more channels may be connected to each other such that the contents of a channel may flow into another channel. In some cases, embodiments where two or more channels may be in fluid communication with each other facilitate providing two or more channels with the same buffer, solution, reagent, etc. from a single upstream input channel. In some cases, embodiments where two or more channels may be in fluid communication with each other facilitate providing a single output channel downstream from two or more channels.

In certain embodiments, the interior volume of the channel is a void. In some instances, the void may be filled with a solution, a buffer, a reagent (e.g., analyte detection reagent or antibody, a protein, an enzyme, a metabolite, etc.), combinations thereof, and the like, as may be desired for an assay protocol. In certain embodiments, the interior volume of the channel contains a material. For example, the interior volume of the channel may contain a polymeric material, such as a polymeric gel. The polymeric gel may be a gel suitable for gel electrophoresis. The polymeric gel may include, but is not limited to, a polyacrylamide gel (e.g., a methacrylamide gel), an agarose gel, and the like. In certain embodiments, the polymeric material in the interior volume of the channel has different physical and/or chemical properties as compared to the polymeric separation medium. For instance, the polymeric material in the interior volume of the channel may have a different pore size, total polymer content (e.g., total acrylamide content), concentration of crosslinker, and/or functional group as compared to the polymeric separation medium.

In certain embodiments, the solution, buffer, reagent, etc. in the channel may be delivered to one or more portions of the polymeric separation medium by diffusion. For example, the solution, buffer, reagent, etc. may be provided in the interior volume of the channel and may be allowed to diffuse into one or more portions of the polymeric separation medium in contact with the channel. In some instances, the solution, buffer, reagent, etc. may be delivered to one or more portions of the polymeric separation medium by directed transport, including, but not limited to, electrophoresis, electroosmosis, pressure-driven flow (e.g., using a pump or gravity), combinations thereof, and the like.

Depending upon the use, any or all of the channels may be the same or different from one another and each may be configured to contain distinct buffers, solution, reagents, etc. Aspects of individual channels are described in more detail below, but may be applied to any or all of the channels in the device.

In certain embodiments, the channel is an elongated channel. An elongated channel has a length that is greater than it width. In some cases, the length of the channel is greater than the width of the channel, such as 2 times, 3 times, 4 times, 5 times, 10 times, 25 times, 50 times, 75 times, 100 times, 125 times, 150 times, 175 times, or 200 times or more greater than the width of the channel.

In certain embodiments, the channel is a microchannel. A "microchannel" is a channel that has dimensions in the micrometer scale. While the dimensions may vary, in some instances, the channel has a width of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less, or 5 µm or less, or 1 µm or less. For example, the channel may have a width ranging from 1 µm to 100 µm, such as 1 µm to 90 µm, or 1 µm to 80 µm, or 1 µm to 70 µm, or 1 µm to 60 µm, or 1 µm to 50 µm, or 1 µm to 40 µm, or 1 µm to 30 µm, or 1 µm to 20 µm or 1 µm to 10 µm.

In certain embodiments, the channel has a depth of 100 µm or less, such as 90 µm or less, or 80 µm or less, or 70 µm or less, or 60 µm or less, or 50 µm or less, or 40 µm or less, or 30 µm or less, or 20 µm or less, or 10 µm or less, or 5 µm or less, or 1 µm or less. For example, the channel may have a depth ranging from 1 µm to 100 µm, such as 1 µm to 90 µm, or 1 µm to 80 µm, or 1 µm to 70 µm, or 1 µm to 60 µm, or 1 µm to 50 µm, or 1 µm to 40 µm, or 1 µm to 30 µm, or 1 µm to 20 µm, or 1 µm to 10 µm.

In certain embodiments, the channel has a length of 10 µm or more, such as 20 µm or more, or 30 µm or more, or 40 µm or more, or 50 µm or more, or 60 µm or more, or 70 µm or more, or 80 µm or more, or 90 µm or more, or 100 µm or more, or 150 µm or more, or 200 µm or more, or 250 µm or more, or 300 µm or more, or 350 µm or more, or 400 µm or more, or 450 µm or more, or 500 µm or more, or 550 µm or more, or 600 µm or more, or 650 µm or more, or 700 µm or more, or 750 µm or more, or 800 µm or more, or 850 µm or more, or 900 µm or more, or 950 µm or more, or 1000 µm or more.

In some embodiments, a channel is separated a certain distance from an adjacent channel. For example, a channel may be separated from an adjacent channel by a distance of 500 µm or less, such as 450 µm or less, or 400 µm or less, or 350 µm or less, or 300 µm or less, or 250 µm or less, or 200 µm or less, or 150 µm or less, or 100 µm or less, such as 90 µm or less, or 80 µm or less, or 70 µm or less, or 60 µm or less, or 50 µm or less, or 40 µm or less, or 30 µm or less, or 20 µm or less, or 10 µm or less, or 5 µm or less.

In certain embodiments, the channel is substantially linear. In other embodiments, the channel is curvilinear. In some instance, one or more portions of the channel are substantially linear while one or more adjacent portions of the channel are curvilinear. In some embodiments, the channel includes one or more bends or corners. In these embodiments, the channel may include a first portion connected to a second portion through the bend or corner. Additional portions of the channel connected by one or more bends or corners may be provided as desired.

As described above, a device that includes a channel finds use in the localized delivery of substances (e.g., solution, buffer, reagent, etc.) to one or more specific portions of the polymeric separation medium. In some embodiments, the channel may facilitate delivery of a substance to the polymeric separation medium at a faster rate as compared to a device that does not include a channel. In some embodiments, the channel facilitates delivery of one or more substances to specific portions of the polymeric separation medium at different time intervals during an assay protocol. For example, a first substance may be delivered to a portion of the polymeric separation medium at a first time point, and a second substance may be delivered to the same or a different portion of the polymeric separation medium at a second time point. In certain cases, the timed release of a substance from a channel may depend on the application of an applied stimulus or a reaction that releases the substance. For instance, a substance may be released from the channel by a light activated reaction, an acid or base activated reaction, or the like. For example, in some instances, the substance to be released is bound to a material in the interior volume of the channel (e.g., through a degradable crosslinker), and may be released (e.g., unbound) from the material by application of an applied stimulus as described above. The unbound substance may then traverse from the interior volume of the channel into the polymeric separation medium. In some embodiments, a device that includes a channel facilitates a reduction in the amount of a substance used during an assay protocol. In some cases, the channel may facilitate an increase in the local concentration of a substance at predetermined portions of the polymeric separation medium. For example, the local concentration of a substance provided in a channel may be greater in areas of the polymeric separation medium adjacent to the channel as compared to areas of the polymeric separation medium at a distance away from the channel.

In certain embodiments, the device includes a channel oriented such that a longitudinal axis of the channel is substantially perpendicular to the plane of the polymeric separation medium, e.g., the channel is oriented vertically with respect to a horizontally disposed polymeric separation medium. In some instances, the channel comprises a central well as described herein. As such, the channel may form a void in the polymeric separation medium, where the polymeric separation medium surrounding the void forms the peripheral walls of the channel. In some cases, the channel (e.g., central well) is substantially circular in shape.

In some instances, the separation medium is configured such that a sample is placed in the channel of the separation medium. In certain cases, the channel includes an open end, such as an open end on the surface (e.g., top surface) of the polymeric separation medium. In some cases, the open end of the channel has an opposing closed end. The closed end may be formed by the polymeric separation medium (e.g., where the height of the channel is less than the thickness of the polymeric separation medium), or may be formed by a solid support which carries the polymeric separation medium (e.g., where the channel passes through the entire thickness of the polymeric separation medium).

In certain embodiments, the channel (e.g., central well) of the polymeric separation medium includes a plurality of microwells positioned on the periphery and in fluid communication with the channel. Microwells in fluid communication with the channel may have an open end that faces the interior volume of the channel, such that a fluid and constituents thereof may flow from the interior volume of the channel to the interior volume of the microwells and vice versa. In some embodiments, each microwell has a closed end opposite from the open end of the microwell. In certain cases, the closed ends of the microwells are formed by the surrounding polymeric separation medium. In certain instances, the microwells are coplanar with the channel. For example, the microwells may be configured such that an axis of the microwell from the closed end to the open end of the microwell is coplanar with a transverse (i.e., horizontal) radius of the channel (e.g., similar to spokes in a wheel). As such, the microwells may have an axis of the microwell from the closed end to the open end of the microwell that is coplanar with the polymeric separation medium. Additional aspects of embodiments of the above channel are described herein in relation to a polymeric separation medium with a central well and a circular arrangement of microwells.

Methods

Embodiments of the methods are directed to separating constituents of a sample, such as constituents of a cell (e.g., cellular components). Aspects of the method include contacting a sample with a polymeric separation medium that includes a plurality of microwells as described above. In certain embodiments, the polymeric separation medium includes functional groups that covalently bond to one or more sample components of interest in the separation medium upon application of an applied stimulus, as described in more detail below. In some cases, the method also includes applying an electric field to the polymeric separation medium in a manner sufficient to move at least some components of the sample from the microwell into the polymeric separation medium to produce separated sample components in the polymeric separation medium.

In certain embodiments, the sample may be contacted to the polymeric separation medium such that constituents of the sample are positioned in one or more microwells in the polymeric separation medium. For example, the sample may be applied to a surface of the separation medium and the constituents in the sample may be allowed to passively settle into the microwells, e.g., passively settle out of solution due to gravity). In some instances, as described above, the polymeric separation medium includes a planar array of microwells, and in some cases the sample constituents may be positioned in the planar array of microwells by applying the sample to the separation medium and allowing the constituents in the sample to passively settle into the planar array of microwells. In certain embodiments, the array of microwells may include microwells that have substantially uniform, or in other embodiments non-uniform, shapes and/or sizes as described above. In embodiments, where the polymeric separation medium includes non-uniform microwells, the method may include size selected settling using different shaped and/or sized microwells. For example, a sample may be applied to the separation medium and sample constituents (e.g., cells) may preferentially settle into certain corresponding microwells depending on the shape and/or size of the cells and microwells.

In other embodiments, as described above, the polymeric separation medium may include a circular arrangement of microwells. In these embodiments, the method of positioning the sample constituents in the microwells may include applying a centrifugal force to the polymeric separation medium in a manner sufficient to position components of the sample in the microwells. For example, the sample may be introduced into the central well of the polymeric separation medium, and then a centrifugal force may be applied (e.g., by spinning the device) such that sample constituents in the central well are forced into one or more microwells on the periphery of the central well. In some instances, the applied centrifugal force may be of a magnitude sufficient to position a sample component, such as a cell, into a microwell of the device. In certain instances, the applied centrifugal force may be of a magnitude sufficient to position a sample component, e.g., a cell, into a microwell of the device without causing significant damage to the constituents in the sample (e.g., cells). In certain instances, the applied centrifugal force is 50 g (gravitational force) or more, such as 60 g or more, or 70 g or more, or 80 g or more, or 90 g or more, or 100 g or more, or 110 g or more, or 120 g or more, or 130 g or more, or 140 g or more, or 150 g or more.

Other methods of positioning sample constituents into a microwell are also possible. For example, sample constituents may be positioned in one or more microwells of the polymeric separation medium by one or more or the following: applying an electric field to the sample; applying a density gradient, physically positioning the sample constituents into the microwell using a positioning device, such as but not limited to a micropipetter, a nozzle, optical tweezers, and the like; applying a pressure force; applying a magnetic force (e.g., where the sample constituents of interest are bound to magnetic beads); convection flow; size selected settling using different sized microwells; positioning droplets of sample containing cells or cell lysates into microwells; combinations thereof and the like.

In certain embodiments, the sample and/or sample components may be manipulated prior to or after positioning the sample components into the microwells. For example, the sample and/or sample components may be manipulated prior to positioning into the microwells. In other embodiments, the sample and/or sample components may be manipulated after positioning into the microwells. In some instances, the sample may include one or more cells of interest. As such, the method may include manipulating the cell to produce cellular components. For instance, the method may include lysing the cell to release cellular components from the cell. In some instances, the cellular components may be produced by differential lysis of specific cellular compartments. For example, differential lysis of specific cellular compartments may facilitate the individual analysis of the contents of different cellular compartments. In certain cases, the cellular components may be produced from the cell by treating the cell such that the cell releases the cellular component of interest (e.g., without lysing the cell). For example, the cell may be treated (e.g., incubated in a warmer or cooler temperature, treated with an active agent, etc.) such that the cell secretes one or more cellular components of interest. In certain embodiments, the cell may be encapsulated in a sample droplet and the sample droplet may be treated as described above such that cellular components are produced. The droplets may be positioned in the microwells and then treated as described above, or the droplets may be treated prior to positioning the droplets in the microwells.

Once the sample constituents are positioned in the microwells, the method may further include separating the sample constituents in the separation medium to produce separated sample constituents. In some cases, the separated constituents are produced by gel electrophoresis as the sample traverses a wall of the microwell and through the separation medium. In other cases, the separated sample is produced by isoelectric focusing in the separation medium. The separated sample may include distinct detectable bands of constituents (e.g., analytes), where each band includes one or more constituents that have substantially similar properties, such as molecular mass, size, charge (e.g., charge to mass ratio), isoelectric point, affinity interaction, etc. depending on the type of separation performed.

For example, in embodiments where the polymeric separation medium includes a planar array of microwells as described above, the method may include separating the sample constituents by applying an electric field across the polymeric separation medium in a manner sufficient to move at least some of the sample constituents through a side wall of the microwell and into the polymeric separation medium to produce separated sample constituents in the polymeric separation medium. In other embodiments where the polymeric separation medium includes a circular arrangement of microwells as described above, the method may include separating the sample constituents by applying an electric field across the polymeric separation medium in a manner sufficient to move at least some of the sample constituents through the closed end of the microwell (e.g., the bottom of the microwell) and into the polymeric separation medium to produce separated sample constituents in the polymeric separation medium.

In certain embodiments, the device is configured to subject a sample to an electric field. The electric field may facilitate the movement of the sample through the device (e.g., electrokinetic transfer of the sample from one region of the device to another region of the device). The electric field may also facilitate the separation of the analytes in the sample by electrophoresis (e.g., polyacrylamide gel electrophoresis (PAGE), SDS-PAGE, isoelectric focusing, etc.), as described above.

For instance, separating the analytes in a sample may include applying an electric field configured to direct the analytes in the sample through the separation medium of the device. The electric field may be configured to facilitate the separation of the analytes in a sample based on the physical properties of the analytes. For example, the electric field may be configured to facilitate the separation of the analytes in the sample based on the molecular mass, size, charge (e.g., charge to mass ratio), isoelectric point, etc. of the analytes. In certain instances, the electric field is configured to facilitate the separation of the analytes in the sample based on the molecular mass of the analytes. In other embodiments, the electric field is configured to facilitate separation of the analytes in the sample based on the isoelectric point (pI) of the analytes.

In some instances, the methods further include immobilizing the separated sample components in the polymeric separation medium. Immobilizing may be accomplished using any convenient approach, e.g., covalently bonding the separated sample components to the polymeric separation medium, such as by exposing the polymeric separation medium to ultra-violet (UV) light. For example, after the constituents in the sample have been separated, the method may further include applying a stimulus to the separation medium to covalently bond the constituents to the separation medium. In some cases, the applying the stimulus includes applying electromagnetic radiation to the separation medium. For instance, the method may include exposing the separation medium to light, such as, but not limited to, visible light, UV light, infrared light, etc. In certain cases, the method includes applying light (e.g., UV light) to the separation medium to covalently bond the constituents to the separation medium.

In certain embodiments, the light used to covalently bond the constituents of interest to the separation medium has a wavelength different from the light used to activate formation of the separation medium. For example, as described herein, the light used to activate formation of the separation medium may have a wavelength of blue light in the visible spectrum. As described above, the light used to covalently bond the constituents of interest to the separation medium may have a wavelength of UV light. As such, in certain embodiments, the method includes exposing the separation medium to a first wavelength of light to form the separation medium, and exposing the separation medium to a second wavelength of light to covalently bond the constituents of interest to the separation medium. The first and second wavelengths of light may be blue light and UV light, respectively, as described herein.

In certain embodiments, the method includes determining whether an analyte of interest is present in a sample, e.g., determining the presence or absence of one or more analytes of interest in a sample. In some instances, the devices are configured to detect the presence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which a measurement of the concentration of the analyte is provided to the user.

In certain embodiments, the method includes detecting an analyte of interest bound to the separation medium. Detectable binding of an analyte of interest to the separation medium indicates the presence of the analyte of interest in the sample. In some instances, detecting the analyte of interest includes contacting the analyte of interest with a label configured to specifically bind to the analyte of interest, e.g., as may be present in an analyte detection reagent. The analyte detection reagent can be any molecule that specifically binds to a protein or nucleic acid sequence or biomacromolecule that is being targeted (e.g., the analyte of interest). Depending on the nature of the analyte, the analyte detection reagent can be, but is not limited to: single strands of DNA complementary to a unique region of the target DNA or RNA sequence for the detection of nucleic acids; antibodies against an epitope of a peptidic analyte for the detection of proteins and peptides; or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the analyte detection reagent includes an antibody. The antibody may specifically bind to the analyte of interest.

In certain embodiments, the analyte detection reagent includes a detectable label. Detectable labels include any convenient label that may be detected using the methods and systems, and may include, but are not limited to, fluorescent labels, colorimetric labels, chemiluminescent labels, multicolor reagents, enzyme-linked reagents, avidin-streptavidin associated detection reagents, radiolabels, gold particles, magnetic labels, and the like. In certain embodiments, the analyte detection reagent includes an antibody associated with a detectable label. For example, the analyte detection reagent may include a labeled antibody (e.g., a fluorescently labeled antibody) that specifically binds to the analyte of interest. As such, the method may include detecting the labeled analyte of interest.

As described above, detecting the analyte of interest includes contacting the analyte of interest with an analyte detection reagent (e.g., a label) configured to specifically bind to the analyte of interest (e.g., an antibody that specifically binds to the analyte of interest). For example, contacting the analyte of interest with an analyte detection reagent may include applying a solution of analyte detection reagent to the polymeric separation medium. The analyte detection reagent may be contacted to any surface of the polymeric separation medium, such as the top or one or more sides of the polymeric separation medium. In some cases, the analyte detection reagent may be moved through the polymeric separation medium such that the analyte detection reagent contacts analytes of interest immobilized within the polymeric separation medium. For instance, the analyte detection reagent may be moved through the polymeric separation medium by applying an electric field to the polymeric separation medium, applying a pressure, applying a centrifugal force, passive diffusion, and the like.

In certain embodiments, detecting the analyte of interest includes contacting the analyte of interest with a primary label that specifically binds to the analyte of interest. In certain embodiments, the method includes enhancing the detectable signal from the labeled analyte of interest. For instance, enhancing the detectable signal from the labeled analyte of interest may include contacting the primary label with a secondary label configured to specifically bind to the primary label. In certain instances, the primary label is a primary antibody that specifically binds to the analyte of interest, and the secondary label is a secondary antibody that specifically binds to the primary antibody. As such, enhancing the detectable signal from the labeled analyte of interest may include contacting the primary antibody with a secondary antibody configured to specifically bind to the primary antibody. The use of two or more detectable labels as described above may facilitate the detection of the analyte of interest by improving the signal-to-noise ratio.

In certain embodiments, the analyte detection reagent may not specifically bind to an analyte of interest. In some cases, the analyte detection reagent may be configured to produce a detectable signal from the analyte of interest without specifically binding to the analyte of interest. For example, the analyte of interest may be an enzyme (e.g., a cellular enzyme) and the analyte detection reagent may be a substrate for the enzyme. In some cases, contacting the analyte detection reagent (e.g., enzyme substrate) to the analyte of interest (e.g., enzyme) may produce a detectable signal as the substrate is converted by the enzyme.

In certain embodiments, the method includes removing the analyte detection reagent and then contacting the analyte of interest with another analyte detection reagent (e.g., stripping and reprobing). For instance, the method may include contacting the labeled analyte of interest with a buffer (e.g., a stripping buffer) configured to dissociate the analyte detection reagent from the analyte of interest. The dissociated analyte detection reagent may then be washed from the polymeric separation medium. In some cases, the analyte of interest may then be contacted with a subsequent analyte detection reagent. The subsequent analyte detection reagent may be the same or different from the initial analyte detection reagent. Stripping and reprobing may facilitate contacting analytes of interest with different analyte detection reagents.

In certain embodiments, the method includes storing the polymeric separation medium. For example, the method may include storing the polymeric separation medium by dehydrating the polymeric separation medium. The polymeric separation medium may be stored for an extended period of time, such as, but not limited to, 1 day, 2 days, 3 days, 4 days, 5 days, 6 days, 1 week, 2 weeks, 3 weeks, 1 month, 2 months, 3 months, 4 months, 5 months, 6 months or more. In some embodiments, the method further includes rehydrating the polymeric separation medium. The rehydrated polymeric separation medium may be used in any of the assay steps described herein. For example, dehydrating and rehydrating the polymeric separation medium may be performed between any of the assay steps, such as, between producing the polymeric separation medium and performing an assay, between immobilizing the analytes of interest to the polymeric separation medium and contacting the analytes with an analyte detection reagent, between stripping and reprobing, etc.

Samples that may be assayed with the subject methods may include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analyte of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular mass, size, charge, isoelectric point, affinity interaction, etc.).

In certain embodiments, the analyte of interest are cells and/or cellular components. In some cases, the cells are obtained from samples (e.g., biological samples), such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes (e.g., cells and/or cellular components) in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: nucleic acids, e.g., double or single-stranded DNA, double or single-stranded RNA, DNA-RNA hybrids, DNA aptamers, RNA aptamers, etc.; proteins and peptides, with or without modifications, e.g., antibodies, diabodies, Fab fragments, DNA or RNA binding proteins, phosphorylated proteins (phosphoproteomics), peptide aptamers, epitopes, and the like; small molecules such as inhibitors, activators, ligands, etc.; oligo or polysaccharides; mixtures thereof; and the like.

In certain embodiments, the method is configured to separate and/or detect constituents of interest in a sample, where the sample size is small. For example, the method may be configured to separate and/or detect constituents of interest in a sample, where the sample size is 1 mL or less, such as 750 µL or less, including 500 µL or less, or 250 µL or less, of 100 µL or less, or 75 µL or less, or 50 µL or less, or 40 µL or less, or 30 µL or less, or 20 µL or less, or 10 µL or less, or 5 µL or less, or 1 µL or less. In some instances, the method is configured to separate and/or detect constituents of interest in a sample, where the sample size is 20 µL or less.

In certain embodiments, the method includes concentrating, diluting, or buffer exchanging the sample prior to directing the sample through the separation medium. Concentrating the sample may include contacting the sample with a concentration medium prior to contacting the sample with the separation medium. The concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method includes contacting the separated analytes bound to the separation medium with a blocking reagent prior to detecting the analyte of interest. In some cases, contacting the separated analytes with a blocking reagent prior to detecting the analyte of interest may facilitate a minimization in non-specific binding of a detectable label to the separated analytes. For example, contacting the separated analytes with the blocking reagent prior to detecting the analyte of interest may facilitate a minimization in non-specific binding of a labeled antibody to the separated analytes. The blocking reagent can be any blocking reagent that functions as described above, and may include, but is not limited to, bovine serum albumin (BSA), non-fat dry milk, casein, and gelatin. In other embodiments, no blocking step is required. Thus, in these embodiments, the method does not include a blocking step prior to detecting the analyte of interest.

In certain embodiments, the method also includes optional washing steps, which may be performed at various times before, during and after the other steps in the method. For example, a washing step may be performed after binding the separated sample to the separation medium, after contacting the separated sample with the blocking reagent, after contacting the separated sample with the detectable label, etc.

Embodiments of the method may also include releasing the analyte bound to the separation medium. The releasing may include contacting the bound analyte with a releasing agent. The releasing agent may be configured to disrupt the binding interaction between the analyte and the separation medium. In some cases, the releasing agent is a reagent, buffer, or the like, that disrupts the binding interaction between the analyte and the separation medium causing the separation medium to release the analyte. After releasing the analyte from the separation medium, the method may include transferring the analyte away from the separation medium. For example, the method may include directing the released analyte downstream from the separation medium for secondary analysis with a secondary analysis device such as, but is not limited to, a UV spectrometer, and IR spectrometer, a mass spectrometer, an HPLC, an affinity assay device, a second microfluidic device as described herein, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular mass, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes. In certain embodiments, multiplex analysis also includes the use of two or more different detectable labels. The two or more different detectable labels may specifically bind to the same or different analytes. In some cases, the two or more different detectable labels may specifically bind to the same analyte. For instance, the two or more different detectable labels may include different antibodies specific for different epitopes on the same analyte. The use of two or more detectable labels specific for the same analyte may facilitate the detection of the analyte by improving the signal-to-noise ratio. In other cases, the two or more different detectable labels may specifically bind to different analytes. For example, the two or more detectable labels may include different antibodies specific for epitopes on different analytes. The use of two or more detectable labels each specific for different analytes may facilitate the detection of two or more respective analytes in the sample in a single assay.

In certain embodiments, the method is an automated method. As such, the method may include a minimum of user interaction with the devices and systems after introducing the sample into the device. For example, the steps of separating the sample constituents in the separation medium to produce a separated sample and applying the stimulus to the separation medium to covalently bond the constituents to the separation medium may be performed by the device and system at predetermined intervals, such that the user need not manually perform these steps. In some cases, the automated method may facilitate a reduction in the total assay time. For example, embodiments of the method, including the separation and detection of analytes in a sample, may be performed in 240 minutes or less, e.g., 180 minutes or less, 120 minutes or less, such as 90 minutes or less, or 60 minutes or less, or 45 minutes or less, or 30 minutes or less, such as 20 minutes or less, including 15 minutes or less, or 10 minutes or less, or 5 minutes or less, or 2 minutes or less, or 1 minute or less.

Aspects of embodiments of the present disclosure further include methods of making the above polymeric separation medium. In some instances, the methods include positioning a monomeric precursor composition of the polymeric separation medium between a first surface and second surface comprising one or more structural features; irradiating the monomeric precursor composition with light having a wavelength sufficient (e.g., blue light) to initiate polymerization of the precursor composition so as to produce the desired composition. The method may further include removing the second surface comprising the one or more structural features such that the first surface (e.g., the solid support) carries a polymeric separation medium that includes a plurality of microwells as described herein. In certain embodiments, the structural features on the second surface include a plurality of posts. The posts on the second surface may include shapes and sizes that correspond to the desired shapes and sizes of the interior volumes of the microwells. In embodiments that include a plurality of posts on the second surface, a polymeric separation medium may be produced that includes a planar array of microwells. In other embodiments, the structural feature on the second surface may correspond to the shape and size of a central well of a polymeric separation medium that includes a circular arrangement of microwells as described herein. For instance, the second surface may include a structural feature such as a cylinder that includes a plurality of posts extending away from the perimeter of the cylinder. The posts on the perimeter of the cylinder may include shapes and sizes that correspond to the desired shapes and sizes of the interior volumes of the microwells. In some embodiments, the height of the cylinder corresponds to the desired thickness of the polymeric separation medium.

Systems

Aspects of certain embodiments include a system configured to perform methods of the present disclosure. In some instances, the system includes a separation medium as described herein. The system may also include a source of electromagnetic radiation (i.e., an electromagnetic radiation source). In some cases, the electromagnetic radiation source is a light source. For example, the light source may include a visible light source, a UV light source, an infrared light source, etc. In some instances, the electromagnetic radiation source includes a light source, such as a UV light source. As described above, the electromagnetic radiation source may be used to apply electromagnetic radiation to the separation medium in the microfluidic device to immobilize (e.g., covalently bond) sample constituents to the separation medium.

In certain embodiments, the system also includes a detector. In some cases, the detector is configured to detect a detectable label. The detector may include any type of detector configured to detect the detectable label used in the assay. As described above, detectable label may be a fluorescent label, colorimetric label, chemiluminescent label, multicolor reagent, enzyme-linked reagent, avidin-streptavidin associated detection reagent, radiolabel, gold particle, magnetic label, etc. In some instances, the detectable label is a fluorescent label. In these instances, the detector may be configured to contact the fluorescent label with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected by the detector to determine the presence of the labeled analyte bound to the separation medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

Systems of the present disclosure may include various other components as desired. For example, the systems may include fluid handling components, such as microfluidic fluid handling components. The fluid handling components may be configured to direct one or more fluids through the device. In some instances, the fluid handling components are configured to direct fluids, such as, but not limited to, fluid samples, buffers (e.g., electrophoresis buffers, wash buffers, release buffers, etc.), and the like. In certain embodiments, the fluid handling components are configured to deliver a fluid to the separation medium of the device, such that the fluid contacts the separation medium. The fluid handling components may include pumps (e.g., microfluidic pumps). In some cases, the pumps are configured for pressure-driven fluid handling and routing of fluids through the devices and systems disclosed herein. In certain instances, the fluid handling components are microfluidic fluid handling components configured to deliver small volumes of fluid, such as 1 mL or less, such as 500 µL or less, including 100 µL or less, for example 50 µL or less, or 25 µL or less, or 10 µL or less, or 5 µL or less, or 1 µL or less.

In certain embodiments, the systems include one or more electric field generators. An electric field generator may be configured to apply an electric field to various regions of the device, e.g., to the separation medium. The system may be configured to apply an electric field such that the sample is electrokinetically transported through the device. For example, the electric field generator may be configured to apply an electric field to the separation medium. In some cases, the applied electric field may be aligned with the directional axis of the separation medium. As such, the applied electric field may be configured to electrokinetically transport the analytes and components in a sample through the separation medium. In some instances, the electric field generators are configured to apply an electric field with a strength ranging from 10 V/cm to 1000 V/cm, such as from 100 V/cm to 800 V/cm, including from 200 V/cm to 800 V/cm, or from 400 v/cm to 800 V/cm.

In certain embodiments, the system includes an electric field generator configured to apply an electric field such that analytes and/or constituents in the sample are isoelectrically focused in the separation medium. For instance, an applied electric field may be aligned with the directional axis of the separation medium and configured to isoelectrically focus the sample constituents along the directional axis of the separation medium.

In some embodiments, the electric field may be directionally distinct. For example, the electric field may be aligned with the directional axis of the separation medium. The electric field may be configured to direct the sample or analytes through the separation medium along the directional axis of the separation medium.

In certain embodiments, the system includes one or more electric field generators configured to generate an electric field. In certain instances, the electric field generators may be proximal to the device, such as arranged on the device. In some cases, the electric field generators are positioned a distance away from the device. For example, the electric field generators may be incorporated into the system for use with the device.

Utility

The subject devices, systems and methods find use in a variety of different applications where determination of the presence or absence, and/or quantification of one or more analytes in a sample is desired. For example, the subject devices, systems and methods find use in the separation and detection of proteins, peptides, nucleic acids, and the like. In some cases, the subject devices, systems and methods find use in the separation and detection of proteins.

The subject devices, systems and methods find use in development and validation of stem cell de-differentiation and differentiation protocols. For instance, induced pluripotent stem cells may be derived from somatic cells such as skin cells, which may involve reprogramming of somatic cells with various external stimuli (e.g., chemical or biological stimuli) to induce the cells to a pluripotent state. In some instances, when experimenting with new external stimuli to achieve pluripotency, it may be desirable to measure the response of the cell population to determine if pluripotency has been achieved. The subject devices, systems and methods find use in measuring these responses of the cell population to determine if pluripotency has been achieved. For example, the subject devices, systems and methods find use in measuring multiple protein targets that are known pluripotency indicators such as, but not limited to, Oct-3/4, Nanog, SSEA-4, and SOX2. The subject devices, systems and methods find use in determining the heterogeneity of the transformed cell population to determine the percentage of the cells that have been successfully transformed to a pluripotent state. Such induced pluripotent stem cells can then be differentiated via external chemical or biological stimuli to derive various cell types such as, but not limited to, cardiomyocytes, neurons, hepatocytes and endothelial cells. The subject devices, systems and methods find use in the validation of such differentiation protocols because, in certain embodiments, subject devices, systems and methods can simultaneously detect multiple protein markers that are indicative of successful differentiation to the target cell type. The subject devices, systems and methods find use in determining the heterogeneity of the transformed cell population to determine the percentage of the cells that have successfully differentiated to the target cell type.

The subject devices, systems and methods also find use in development and validation of "disease-in-a-dish" models. For example, it may be challenging for researchers to study diseases in the human brain since extracting neurons from living patients is difficult and risky. As an alternative, cellular models of disease may be created to allow basic scientific research and drug development. Such models can be created, for example, by differentiation of neurons from induced pluripotent stem cells (IPSCs) derived from skin cells donated by patients with a genetic neurodegenerative disease. To create these models, stem cell differentiation protocols may be developed and validated as previously described to de-differentiate skin cells to stem cells and then differentiate the stem cells to neurons. Once this transformation is successful, the model may be validated by determining that characteristics of the disease are present in the differentiated cells. For example, neurons can be created from the skin cells of patients with Huntington's disease. Once created, the derived cells may be tested for expression of the diseased form of the Huntingtin protein. The subject devices, systems and methods find use in detecting the presence and heterogeneity of the Huntingtin protein in the disease model and verifying similarity to primary cells. Disease-in-a-dish models may also be created through selection or genetic modification of cell lines. Such cells may be validated to ensure that the genetic modification results in stable expression of a diseased biomarker (e.g., a protein) that mimics what is seen in diseased primary cells. The subject devices, systems and methods find use in creating disease models of the liver, kidney, heart, brain, blood or other organs, tissues and cell types.

The subject devices, systems and methods also find use in measuring the heterogeneity of cancerous tumors. Specific biomarkers such as, for example, HER-2 and BRAF, are indicative of certain cancer mutations and are targets for drugs such as trastuzumab and vemurafenib, respectively. Cancer may be a highly heterogeneous disease and targets such as HER-2 and BRAF may not be expressed uniformly within a tumor. Such heterogeneity may have implications for clinical diagnosis and treatment. The subject devices, systems and methods find use in analyzing the heterogeneity of multiple targets in a cell population derived from a tumor biopsy. Such an approach may facilitate basic scientific research, drug discovery and development, and companion diagnostics for targeted therapeutics.

The subject devices, systems and methods also find use in the determination of the mechanism of action of drug compounds. For example, "disease-in-a-dish" models may be used as in vitro test platforms for drug development.

Drugs can be developed to target specific targets and pathways that are present in both the disease and disease models. The subject devices, systems and methods find use in analyzing the heterogeneous response of a cell population after exposure to a drug candidate. Response to the drug can be correlated to the presence of the primary target and heterogeneous responses within the cell population not explained by the presence or absence of the primary target can be further correlated with other proteins and signaling pathways. In this way, the subject devices, systems and methods find use in determining the mechanism of action of the drug, which may facilitate more efficient research, development and eventual approval of the drug compound.

The subject devices, systems and methods also find use in the analysis of circulating tumor cells (CTCs) isolated from blood. CTCs are cancerous cells in circulation that are shed from primary tumors and may be used for early cancer diagnosis, prognosis, monitoring of treatment, detection of metastases, or other uses. Since the CTCs are heterogeneous, each individual cell may be tested for protein biomarkers that are indicative of invasiveness, proliferation, or other factors. Typical methods for enriching CTCs from whole blood yield a suspension of cells enriched in the target CTCs. The subject devices, systems and methods find use in analyzing such a cell suspension, for example using methods utilizing active settling of the cells to maximize the number of cells in the input suspension that are captured and analyzed. Analysis of CTCs by the subject devices, systems and methods find use for basic scientific research, management of minimum residual disease, and cancer diagnosis. In certain instances, active settling includes positioning the sample constituents in one or more microwells using one or more or the following: applying an electric field to the sample; applying a density gradient, physically positioning the sample constituents into the microwell using a positioning device, such as but not limited to a micropipetter, a nozzle, optical tweezers, and the like; applying a pressure force; applying a magnetic force (e.g., where the sample constituents of interest are bound to magnetic beads); convection flow; size selected settling using different sized microwells; positioning droplets of sample containing cells or cell lysates into microwells; combinations thereof and the like.

The subject devices, systems and methods also find use in analysis downstream of fluorescence activated cell sorting (FACS). FACS can sort millions of cells and isolate subpopulations as small as a few hundred cells. However, further analysis of such small subpopulations by flow cytometers may not be suitable because typical flow cytometers require a minimum of 10,000 or more cells. The subject devices, systems and methods find use in analyzing such small cell subpopulations, for example using methods utilizing active settling or placement of the cells to maximize the number of cells in the input suspension that are captured and analyzed. The subject devices, systems and methods find use in the further analysis of the subpopulation for protein targets that include targets in the FACS sort as well as targets that were not part of the FACS sort. For example, primary cells derived from cancerous human or animal tissue can be sorted by FACS to isolate a subpopulation of cells that are putative cancer cells based on one or more surface markers. The subject devices, systems and methods can then be used to confirm the presence of the one or more surface markers and assay for additional targets such as, for example, intracellular proteins and transcription factors that will further characterize the state and heterogeneous composition of the isolated subpopulation.

The subject devices, systems and methods find use in the detection of nucleic acids, proteins, or other biomolecules in a sample. The methods may include the detection of a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, or in the ongoing management or treatment of a disease condition in a subject, etc. In addition, the subject devices, systems and methods may find use in protocols for the detection of an analyte in a sample, such as, but not limited to, Western blotting, and the like.

The subject devices, systems and methods find use in detecting biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods find use in portable and point-of-care or near-patient molecular diagnostics.

The subject devices, systems and methods find use in detecting biomarkers for a disease or disease state. In certain instances, the subject devices, systems and methods find use in detecting biomarkers for the characterization of cell signaling pathways and intracellular communication for drug discovery and vaccine development. For example, the subject devices, systems and methods may be used to detect and/or quantify the amount of biomarkers in diseased, healthy or benign samples. In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like.

The subject devices, systems and methods find use in diagnostic assays, such as, but not limited to, the following: detecting and/or quantifying biomarkers, as described above; screening assays, where samples are tested at regular intervals for asymptomatic subjects; prognostic assays, where the presence and/or quantity of a biomarker is used to predict a likely disease course; stratification assays, where a subject's response to different drug treatments can be predicted; efficacy assays, where the efficacy of a drug treatment is monitored; and the like. For example, one or more biomarkers may be detected and monitored over an extended period of time, such as over several days, several weeks or several years. Changes in the presence and/or quantity of the one or more biomarkers may be monitored over an extended period of time.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time. For example, the subject devices, systems and methods find use in probed IEF separation medium for affinity reagent screening. High-throughput microfluidic devices that include a separation medium as described herein may be used to select biomarker isoform-specific affinity reagents, such as specific monoclonal antibodies. Such reagents may be used in ELISA assays for disease-specific biomarker isoforms present in clinical proteinaceous samples. In some cases, reagents may be screened in serial or for their multiplexed (parallel) capability for highly specific binding.

The subject devices, systems and methods also find use in a variety of different applications where separation of one or more constituents (e.g., analytes) in a sample is desired. The constituents in the sample may be separated based on a variety of different separation techniques, such as, but not limited to, electrochromotography, electrophoretic immunoassays, equilibrium separations (including isoelectric and temperature gradient focusing), micellar electrokinetic chromatography, chromatography variants, native electrophoresis, and separation by protein mass under denaturing conditions (e.g., SDS-PAGE). Any of the separation techniques may be coupled to subsequent analyte probing by, for example, antibodies (or variants), lectins, substrates, ligands, lipids, coated particles or dyes. For example, separation based on protein sizing with subsequent antibody probing provides an integrated microfluidic Western blotting device.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the mass and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of embodiments of the present disclosure further include kits configured for use in the methods described herein. In some instances, the kits include a device as described herein, such as a device that includes a polymeric separation medium having a plurality of microwells. In certain embodiments, the kit may include a packaging configured to contain the device. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

Aspects of the present disclosure additionally include kits that further include a buffer. For instance, the kit may include a buffer, such as an electrophoresis buffer, a sample buffer, and the like. In certain cases, the buffer is an electrophoresis buffer, such as, but not limited to, a Tris buffer, a Tris-glycine, and the like. In some instances, the buffer includes a detergent (such as sodium dodecyl sulfate, SDS).

The kits may further include additional reagents, such as but not limited to, release reagents, denaturing reagents, refolding reagents, detergents, detectable labels (e.g., fluorescent labels, colorimetric labels, chemiluminescent labels, multicolor reagents, enzyme-linked reagents, detection reagents (e.g., avidin-streptavidin associated detection reagents), e.g., in the form of at least one if not more analyte detection reagents (such as first and second analyte detection reagents), calibration standards, radiolabels, gold particles, magnetic labels, etc.), and the like.

In certain embodiments, the kit may include an analyte detection reagent, such as a detectable label, as described herein. The detectable label may be associated with a member of a specific binding pair. Suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the member of the specific binding pair includes an antibody. The antibody may specifically bind to an analyte of interest in the separated sample bound to the separation medium. For example, the detectable label may include a labeled antibody (e.g., a fluorescently labeled antibody) that specifically binds to the analyte of interest.

In addition to the above components, the subject kits may further include instructions for practicing the subject methods. These instructions may be present in the subject kits in a variety of forms, one or more of which may be present in the kit. One form in which these instructions may be present is as printed information on a suitable medium, e.g., a piece or pieces of paper on which the information is printed, in the packaging of the kit, in a package insert, etc. Another means would be a computer readable medium, e.g., CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example 1

Single Cell Immunoblotting Via Photoactive Polyacrylamide Micropatterning
Summary Embodiments of the present disclosure provide for rapid, quantitative analysis of single cell protein expression in a single instrument. Embodiments include a microfluidic approach to single cell immunoblotting that includes single cell capture into a thin photoactive polyacrylamide sheet micropatterned with wells on the order of the size of a single cell. In a single microscope slide format, the single cell blot is used to perform polyacrylamide gel electrophoresis, protein immobilization with SDS removal (blotting), and subsequent antibody probing. The scalable, high-throughput nature of microfluidic design underpins single cell immunoblots adaptable to approx. 10,000 cell throughput per slide, and to fast 3 hr assay implementations. This method can also be used for other immunoblotting assays (e.g., native, DNA-protein, RNA-protein) and for reagents other than antibodies (e.g., aptamers, nanobodies, lectins, proteins). Embodiments may also be used for assays of single cells or multiple cells. In certain embodiments, a photopatternable (blue light) and photoreactive (UV light) polyacrylamide gel is used for both an SDS-PAGE separation matrix with a defined stacking interface and, after brief UV-switching, a protein immobilization matrix with high capture efficiencies (>75%). In some instances, analytes are immobilized in the separation medium only after applied UV light, and as such blocking steps are not required. In the examples discussed below, the single cell immunoblot assay was used for neural stem cell analysis, showing sensitivities on the order of 40,000 protein molecules of a given analyte of interest.

In certain embodiments, cells are immunoblotted for a range of protein differentiation markers at a throughput in the thousands of cells per hour of assay time (total assay times are less than 2 hours). The microscope slide format integrates with microarray scanning detection, allowing 4-plex calibrated detection of markers in the $10^2$-$10^6$ copies-per-cell concentration range.

Single cell western blotting may reduce sample requirement from the 10,000-cell+ range of typical western blotting workflows to single cell sensitivity. In some embodiments, this technique separates protein constituents of single cells as well as quantifying them, providing performance in comparison to standard methods such as flow cytometry, single-cell transcriptomics and whole-cell imaging techniques. Extracting molecular weight information from protein separations allows for the analysis of protein-protein interactions.

Methods

Dual Band-Tunable Photoactive Capture Gel with Tunable Porosity (PACTgel) for Protein Separations and Capture from Single Cells A glass microscope "open-gel" for single cell immunoblotting was used. Thin (approx. 30 micron) thick polyacrylamide gels were fabricated by chemical or photochemical polymerization at the interface between methacrylate-functionalized glass slides and SU-8-on-silicon micropost molds. Microposts were typically 30 microns in height and 20 microns in diameter. The fabricated gel was lifted away from the silicon mold to yield thin polyacrylamide sheets stippled with microwells that served as containers for single cells. The polyacrylamide was also photoactive and included a dual spectral band photoactive protein capture gel with tunable porosity (PACTgel) separation and blotting polymer. Using microfluidics and the functional polymer, the assay steps from cell settling to weight-based separation of denatured protein analytes (SDS-PAGE) to immunoblotting with fluorescently labeled primary and secondary antibodies were performed within the polymer layer in about 3 hrs. The polyacrylamide-based PACTgel scaffold was built using a riboflavin-driven photopolymerization strategy that preserved a spectrally distinct UV light-responsive capture functionality of the gel. Photochemically fabricated PACT-gels were patterned using blue light. PACTgels were also optimized for quantitative protein analyte capture following PAGE separations (~30% capture efficiencies for all analytes) with UV exposure times of 45 s applied via a UV spot light source. Because of the benzophenone-functionalized, light-activated character of the gel, no separate blocking steps were needed after protein immobilization. Simultaneous probing of up to 4 protein analyte species has been performed with spectrally multiplexed secondary antibody detection.

Single Cell Immunoblot Assay Design

The polyacrylamide gel layer was engineered for several functional roles including: 1) capture via gravity-based settling into microwells suited to single cell capture at 50% or more occupancy, 2) lysis and constraint of solubilized protein contents in a picoliter-scale injection volume, 3) stacking of protein contents against and through the walls of the microwells, 4) sieving of protein bands within the gel matrix, 5) immobilization of proteins via a highly efficient UV-light triggered capture process mediated by copolymerization of protein cross-reactive benzophenone groups within the gel scaffold, and 6) fluorescent in-gel antibody-based probing.

Using this platform, expression of key rat neural stem cell markers (namely nestin and sox2) were tracked during in vitro differentiation through intermediate states towards neuronal and glial endpoints. An array of subpopulation dynamics were resolved with absolute quantitation of marker levels from single cell immunoblots, allowing dissection of proteomic heterogeneity in the differentiation process.

Detailed Protocol

This protocol describes fabrication and experimental procedures used for single-cell immunoblotting using a perforated polyacrylamide sheet on a 1"×3" microscope slide chip. Materials and equipment used:

Methacrylate-functionalized glass slides from Arraylt (product no. SMRY3; Sunnyvale, Calif.).

Optional: 8×2 well gasketed hybridization cassette from Arrayit (product no. AHC1×16).

ThorLabs (Newton, N.J.) collimated blue 470 nm LED light source (M470L2-C1) with driver (LEDD1B) and 15V power supply (TPS001).

Small trays for slide incubation. These were made from e.g. the bases of cell culture bottles.

Standard gel electrophoresis power supply, e.g. BioRad PowerPac HV (Hercules, Calif.). (e.g., a power supply of >50 mA to run the full chip).

Hamamatsu UV spot light source (San Jose, Calif.).

Fluorescence microscope for separations and readout imaging.

Reagents (all Percentages are w/v Unless Otherwise Noted in Table 1):

TABLE 1

Reagent composition & preparation.

| PACTgel precursor—Photoactive protein capture gel with tunable porosity. Reagents are listed in suggested order of addition: | | |
| --- | --- | --- |
| H$_2$O | 324 µl | |
| BioRad 1.5M Tris HCl pH 8.8 | 25 µl | 75 mM final |
| 30% T, 2.6% C acrylamide stock (37.5:1) | 117 µl | 7% T, 2.7% C |
| 100 mM BPMAC in DMSO | 15 µl | 3 mM, 3% DMSO |
| Degas before adding remaining reagents | | |
| 5% SDS | 10 µl | 0.1% |
| 5% Triton X-100 | 10 µl | 0.1% |
| 0.1% Riboflavin 5' phosphate | 3 µl | 0.0006% |
| 10% ammonium persulfate (APS) | 0.75 µl | 0.015% |
| 10% v/v Tetramethylethylenediamine (TEMED) | 2.5 µl | 0.05% |
| | 0.5 ml | |
| Pulse gel precursor twice by gentle vortexing to just mix, avoiding introduction of oxygen. | | |
| RIPA-like Lysis/EP buffer: | | |
| H$_2$O | to 100 ml | |
| 10X BioRad Tris-Glycine pH 8.3 | 5 ml | 0.5X |
| SDS | 500 mg | 0.5% |
| Triton X-100 | 100 µl | 0.1% v/v |
| Sodium Deoxycholate | 250 mg | 0.25% |
| | 100 ml | |

Protocol (Optional Stopping Points are Indicated by \STOP"):

1. Gel Fabrication
   (a) Begin with a silicon wafer fabricated with the desired post geometries in SU-8,
   (b) The wafer was silanized in vacuo next to a small petri dish containing 2 ml of dichlorodimethylsilane (DCDMS) for 60 min. The wafer was rinsed with water and dried using a nitrogen stream.
   (c) A methacrylate-functionalized glass slide was placed onto the wafer over the post structures, with the treated side down.
   (d) PACTgel precursor solution was prepared and degassed.
   (e) Detergents and initiators were added to PACTgel precursor, mix, and injected steadily from one of the short sides of the slide, after fully wetting the edge to prevent bubble entrainment.
   (f) After loading, the slide was gently pressed to squeeze excess precursor solution from the gap and to ensure that the posts on the wafer were in contact with the slide.
   (g) A blue LED was directed downwards and at an angle to illuminate the entire slide from above. The slide was illuminated for 7.5 min at a local intensity of approx. 470 lux.
   (h) Polymerization was allowed to continue for 10-15 more minutes on the bench top, with the LED off.
   (i) 2 ml PBS was applied along the edges of the slide with a 1 ml pipetor. This facilitated lifting the slide from the wafer.
   (j) The slide was lifted from one of the short edges using a sharp razor blade to lever the slide from the silicon wafer.
   (k) Well integrity was checked using a microscope and the slide was immersed in PBS, gel side up, until settling cells.

STOP

Figure 6:
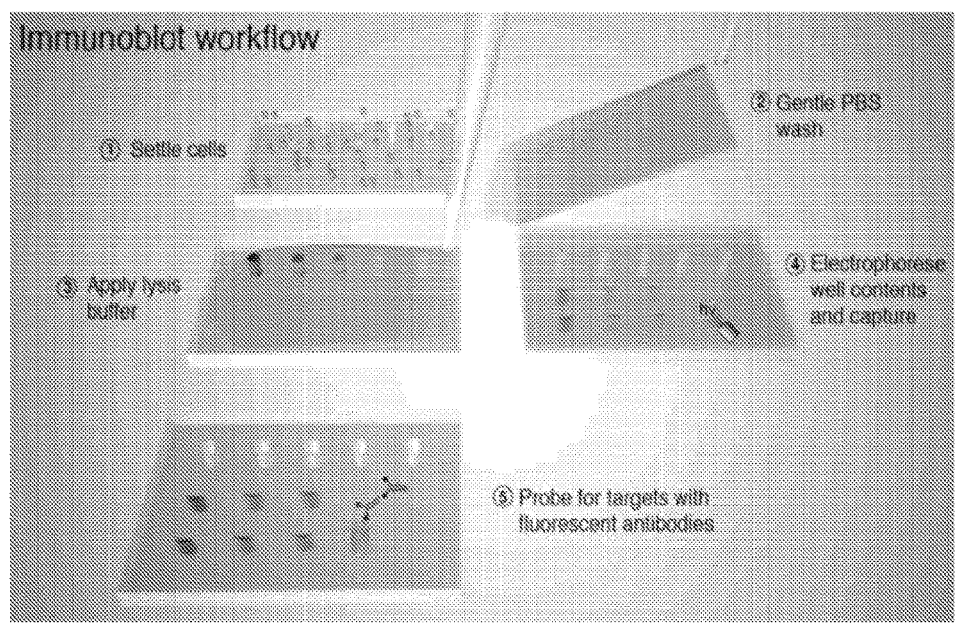
FIG. 6 shows an immunoblot workflow according to embodiments of the present disclosure.

2. Cell Settling (FIG. 6)
   (a) Cells were resuspended in PBS and counted. In certain embodiments, optimal well filling occurred at approximately 1-3×10$^6$ cells/ml.
   (b) The slide was removed from PBS bath, excess liquid was removed by draining to a corner, and the slide was placed on a large dry petri dish. 1-1.5 ml cell solution was applied and incubated for 5-10 minutes. Cell settling was checked periodically using a microscope.
   (c) The petri dish was tipped at a 10-20° angle and cell solution was removed from the lower edge using a pipet or gentle vacuum.
   (d) The slide was washed gently by applying 1 ml aliquots (2-3 times) to the elevated edge and removing from the lower edge with gentle vacuum. The slide surface was checked for stray cells and the assay proceeded when slide was relatively clean.
   (e) 1 ml PBS was applied to one edge of the at slide so that it spread over about half of the slide, and a clean plain slide was applied to the top by lowering from one edge. The PBS spread evenly between the gap as the slide was lowered, and excess ran off the edges.
   (f) Excess PBS was wiped away.
   (g) The whole slide was imaged under bright field using 4× magnification, 1×1 binning to allow later counting of well occupancy.
   (h) The top slide was removed and the following steps were performed immediately to prevent the slide from drying out.

3. Lysis & Separation (FIG. 6)
   (a) The cell slide was placed in an open, dry electrophoresis dish with platinum electrodes running the length of each edge of the slide, using vaseline at short edges to temporarily adhere slide to the dish.
   (b) The dish was placed on a clear-bottomed stage on the microscope.
   (c) After focusing on a fluorescent cell, 8 ml N2-purged lysis/EP buffer was poured over the entire slide and against the electrodes.
   (d) Cell lysis (approx. 10 s) was observed, then 200-250V was applied and fluorescent protein migration was observed.
   (e) The electric field was stopped and UV light was applied via the Hamamatsu supply at a distance of approx. 75 mm for approx. 45 s to capture protein bands. The power was approximately 40 mW cm$^2$.
   (f) The slide was removed from EP dish and placed in a 40 ml conical with PBS and stored at 4° C. until probing (can be done up to a week or more after separation and capture).

STOP

4. Immunoblotting (FIG. 6)
   (a) Antibodies were applied at high concentration to minimize exclusion from the polyacrylamide layer (approx. 10× dilution, or about 0.6 µM) in TBS (100 mM tris pH 7.5+150 mM NaCl) containing 0.1% Tween (TBST) and 2% BSA.

(b) Antibodies were incubated with the slide against a plain glass wafer in the gap formed by 60 µm SU-8 shims (approx. 140 µl antibody solution), or using the Arraylt microarray hybridization cassette (approx. 40 µl antibody solution per cassette well) if multiple targets are to be probed. The incubation time was about 1 hr.

(c) The slide was washed between probings in a bath of TBST (no BSA) for 10-20 min.

(d) The chip was imaged by tiled exposures on fluorescence microscope or using a microarray scanner.

Example 2

Introduction

Understanding protein-mediated cell signaling and differentiation processes may be facilitated by capturing response heterogeneity for single cells in large populations. Experiments were performed using single-cell western blots on standard microscope slides that achieved 103-104 molecule detection limits for >6 protein targets per blot in a<4 hr process. An open microfluidic polyacrylamide microwell array enabled gravity-driven capture of single cells into the polyacrylamide microwell array, which was capable of UV-initiated protein capture. Large-scale lysis of cells within microwells, electrophoretic separation of protein species, blotting, and antibody-mediated detection of specific targets was performed for ~2,000 single cells per slide. The physical principles of the assay and device design are described below. Experiments were performed to apply the single cell western blot to two dynamic processes: neural stem cell responses over stimulation and differentiation timescales. The devices and methods disclosed herein find use for high throughput analysis of protein signaling that may be difficult to detect using typical currently available protocols due to reliance on antibody-based detection alone, or by sensitivity limits that require analysis of pooled populations of cells.

The devices and methods of the present disclosure also find use in the study of heterogeneity in cellular processes, including tissue and organismal development, cancer, response to pharmaceuticals, and immune response. For example, the devices and methods disclosed herein find use in the study of cellular responses, and for targeted protein measurement tools suitable for assaying single cells in large populations. The present devices and methods find use for high specificity protein assays capable of measuring cell-to-cell heterogeneity among populations of cells. The devices and methods may be used for assays in which thousands of cells are individually assessed by western blotting. Western blotting combines protein electrophoresis (to report molecular mass) and subsequent labeling with a detectable probe (to yield probe-target interaction), making the assay useful for semi-quantitative protein analyses in complex backgrounds.

Experiments were performed to study pluripotent stem cell differentiation into a diverse set of cell lineages in response to a homogeneous stimulus in vitro by studying heterogeneous and dynamic protein expression and phosphorylation responses for a neural stem cell model system over response timescales of minutes to days.

Methods

Cell Culture

Neural stem cells (NSCs) were isolated from the hippocampi of adult female Fisher 344 rats and cultured on tissue culture-treated polystyrene plates coated with 10 µg/mL polyornithine (P3655, Sigma-Aldrich, St. Louis, Mo.) and 5 µg/mL laminin (23017-015, Life Technologies, Foster City, Calif.). NSCs were cultured in 1:1 DMEM/F12 (11039-021, Life Technologies) supplemented with N-2 (17502-048, Life Technologies) and 20 ng/mL recombinant human FGF-2 (100-18, PeproTech, Rocky Hill, N.J.), and subcultured at 80% confluency using accutase (A11105-01, Life Technologies) for cell detachment.

Figure 2:
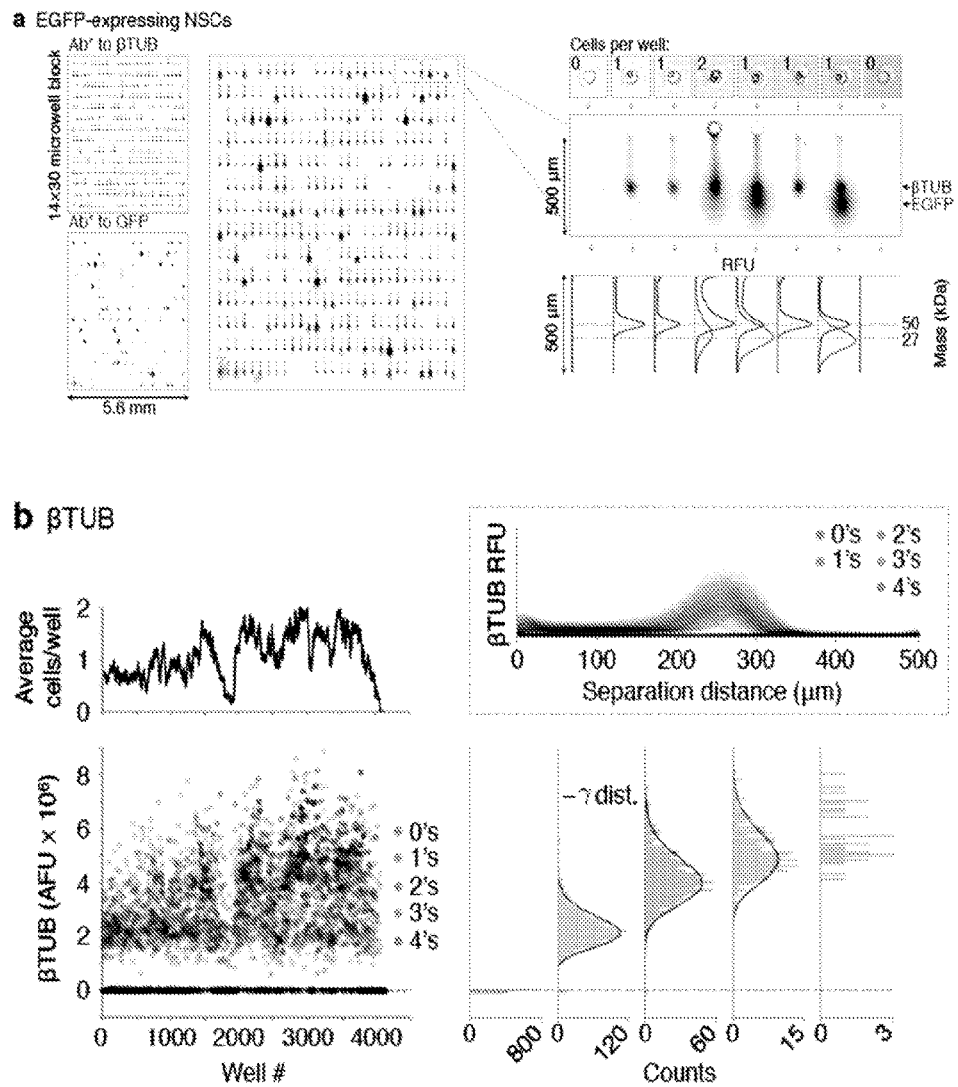
FIG. 2a shows images of scWestern blotting of neural stem cell (NSC) populations, according to embodiments of the present disclosure.
FIG. 2b (top right) shows a graph of the uniformity of separations performance across a scWestern array indicated by profiles of line fluorescence intensity across 4,128 blots for βTUB, grouped by cells-per-well (0's, 1's, 2's, etc.), according to embodiments of the present disclosure.
FIG. 2c shows graphs of calibrated fluorescence distributions for single and zero cell-per-well EGFP blots were comparable in expression gating and dynamic range to conventional flow cytometry following antibody probing of EGFP in fixed NSCs (EGFP transfected, +ve, and untransfected, −ve, NSCs), note arcsin h-transformed scales, according to embodiments of the present disclosure.
FIG. 2d shows linear direct calibration curves for ERK1, pERK1 (Thr202/Tyr204), βTUB, and EGFP purified standards (±SD, n=3 regions of interest per dot blot) span approximate physiological concentration ranges for ERK and βTUB (corrected to the expected concentration in a blotted band from literature values for in-cell concentration), according to embodiments of the present disclosure.

EGFP NSC cell lines were created through stable retroviral infection. The retroviral vector pCLPIT-GFP was packaged and purified virus was titered on NPCs. High-expressing EGFP NSCs were infected at a multiplicity of infection of 3 (MOI=3) and analyzed in FIG. 2, while low expressing EGFP NSCs were infected at MOI=0.5 and used in all other studies. Stable cell lines were obtained through selection in media containing 0.3 µg ml$^{-1}$ puromycin for 72 h (P8833, Sigma-Aldrich).

EGFP NSCs for scWestern blot EGFP expression studies were cultured as described for uninfected NSCs. For scWestern blot signaling studies, EGFP NSCs were FGF-starved for 16 hours. Cells were detached with accutase and suspensions analyzed by scWestern blotting (see Single cell immunoblot assay, below). EGFP NSCs for scWestern blot differentiation studies were cultured in DMEM/F12/N2 supplemented with 0.5 ng/mL FGF-2, 1 µM retinoic acid (RA, BML-GR100, Enzo Life Sciences, Farmingdale, N.Y.), and 1% fetal bovine serum (FBS, SH3008803, Thermo-Fisher Scientific, Waltham, Mass.) for 0-6 days. Cells were detached with trypsin EDTA after the desired differentiation time (25-053-Cl, Corning Cellgro, Manassas, Va.) and analyzed (N.B. cells were not differentiated within microwells; see Single cell immunoblot assay, below). For related flow cytometry, western blotting, and immunocytochemistry experiments, see Validation assays.

Proteins and Reagents

15 µm fluorescent polystyrene microspheres were from Life Technologies (F-8844, Foster City, Calif.). Alexa Fluor 488-labeled purified ovalbumin and bovine serum albumin were also from Life Technologies (034781, A13100). Purified standards for single-cell immunoblot calibration were: β-tubulin from bovine brain (TL238, Cytoskeleton, Denver, Colo.), recombinant EGFP, His-tagged (4999-100, BioVision, Milpitas, Calif.), recombinant human pERK1 (ab116536, Abcam, Cambridge, Mass.). Aliquots of these purified standards were labeled with Alexa Fluor 568 using a protein labeling kit according to vendor instructions (A-10238, Life Technologies) for the determination of partition coefficients in indirect calibration experiments (see Single cell immunoblot calibration, below).

Purified His-tagged Dronpa was expressed in Rosetta competent cells transformed using a pET His6 tobacco etch virus (TEV) ligase independent cloning (LIC) cloning vector, 2BT (EMD Millipore, Billerica, Mass.), grown in 2YT medium at 37° C. to an OD600 of 0.5, induced with 0.5 mM IPTG and grown for an additional 2.5 hours at 37° C. before harvesting. Cells were pelleted by centrifugation at 5,000 rpm for 15 mins at 4° C. and the pellets resuspended in Nickel buffer A supplemented with protease inhibitors (25 mM HEPES pH 7.5, 400 mM NaCl, 10% glycerol, 20 mM imidazole, 1 µg/ml leupeptin and pepstatin, 0.5 mM PMSF). Cells were lysed using an Avestin C3 homogenizer (Ottawa, ON, Canada) at a pressure of 15,000 psi. Cell debris was pelleted at 15,000 rpm for 30 min. The clarified lysate was loaded onto a 5 ml HisTrap FF Crude column (GE Healthcare, San Francisco, Calif.), and unbound material was washed out with Nickel buffer A. Bound protein was eluted with a 10CV gradient up to 400 mM imidazole in Nickel buffer A. Absorption of the eluting material was monitored at 503 nm as well as at 280 nm to aid in pooling the target protein. Fractions containing dronpa were pooled and desalted into IEX buffer A (50 mM sodium phosphate pH 6.5). Desalted protein was loaded onto a 5 ml SP HP ion exchange column (GE Healthcare) and unbound material was washed out with IEX buffer A. Bound material was eluted with a 20CV gradient up to 1 M NaCl in IEX buffer A. Fractions containing dronpa were pooled and assayed for aggregation by analytical size exclusion chromatography on a Superdex 200 5/150 column (GE Healthcare) equilibrated in 25 mM HEPES, 400 mM NaCl, 10% glycerol, 1 mM DTT. Samples were finally desalted into storage buffer (50 mM sodium phosphate pH 6.5, 150 mM NaCl, 10% glycerol, 1 mM DTT).

Details of antibody reagents used are listed in the methods sections corresponding to scWestern, conventional western blotting, and immunocytochemistry assays.

N-[3-[(4-benzoylphenyl)formamido]propyl]methacrylamide (BPMAC) was synthesized in-house via the reaction of the succinimidyl ester of 4-benzoylbenzoic acid with N-(3-aminopropyl)methacrylamide hydrochloride in the presence of catalytic triethylamine according to standard protocols.

Fabrication of Microwell scWestern Solid Supports

SU-8 microposts were fabricated on mechanical grade silicon wafers by standard soft lithography methods. SU-8 2025 photoresist (Y111069, MicroChem, Newton, Mass.) was spun to layer thicknesses of (typically) 30 µm according to manufacturer guidelines and exposed to 365 nm UV light at ~40 mW cm$^{-2}$ for 12 s under a mylar mask printed with 20 µm circular features at 20,000 dpi. The features were arranged in a square configuration with a pitch of 500 µm in the direction of separations and 190 µm in the transverse direction. 2×8 blocks of 14×30 features (6,720 total) were spaced 9 mm apart to match the dimensions of a 2×8 well microarray hybridization cassette (AHC1X16, ArrayIt Corp., Sunnyvale, Calif.). 1 mm-thick rails spanning the length of the micropost array at a spacing of 24 mm were also patterned to support glass solid supports at the height of the microposts. Uniformity of features after exposure and development using SU-8 developer solution (Y020100, MicroChem) were verified by optical profilometry. The measured feature heights and diameters within a micropost block were 30.30±0.15 µm (±SD, n=4 microposts) and 20.52±0.68 µm (±SD, n=4 microposts) respectively. Between-block CV's in the height and diameter measurements for blocks spaced across the full length of the array were 1.1% and 5.2%, respectively (n=3 microposts). Wafers were silanized by vapor-deposition of 2 ml of the hydrophobic silane dichlorodimethylsilane (DCDMS, 440272, Sigma-Aldrich) for 1 hr in vacuo, washed thoroughly with deionized water, and dried under a nitrogen stream immediately prior to use.

Plain glass microscope slides (48300-047, VWR, Radnor, Pa.) were silanized to establish a self-assembled surface monolayer of methacrylate functional groups according to standard protocols. Silanized slides were placed face-down onto micropost wafers and manually aligned to the SU-8 rail and micropost features. Gel precursor solutions were 8% T (wt/vol total acrylamides), 2.7% C (wt/wt of the crosslinker N,N'-methylenebisacrylamide from a 30% T, 2.7% C stock (A3699, Sigma-Aldrich); 3 mM BPMAC from a 100 mM stock in DMSO, 0.1% SDS (161-0301, BioRad, Hercules, Calif.), 0.1% Triton X-100 (BP151, Fisher, Hampton, N.H.), 0.0006% riboflavin 5' phosphate (F1392, Sigma-Aldrich), 0.015% ammonium persulfate (APS, A3678, Sigma-Aldrich), and 0.05% tetramethylethylenediamine (TEMED, T9281, Sigma-Aldrich) in 75 mM tris buffer titrated with HCl to a pH of 8.8. For confocal imaging of cells in rhodamine-tagged scWestern gels, the precursor included the fluorescent monomer methacryloxyethyl thiocarbamoyl rhodamine B (23591, Polysciences, Warrington, Pa.) at 3 µM from a 100 µM stock in DMSO. The precursor mixture was sonicated and degassed (Aquasonic 50D, VWR) for 1 min in vacuo immediately prior to the addition of detergents (SDS, Triton) and polymerization initiators (riboflavin, APS, TEMED). The precursor was then injected into the gap between the glass slide and silicon wafer using a standard 200 µl pipet. After allowing ~30 s for precursor to wick through the gap, the slide was exposed to blue light for 7.5 min at 500 lux (advanced light meter, 840022, Sper Scientific, Scottsdale, Ariz.) from a collimated 470 nm LED (M470L2-C1, Thor labs, Newton, N.J.) mounted above the slide. Polymerization was allowed to continue for an additional 11 min. Gel-fabricated glass slides were wetted at their edges using 2 ml of phosphate-buffered saline (PBS), pH 7.4 (21-040, Corning, Tewksbury, Mass.) and levered from wafers using a razor blade. Fabricated slides could be stored at 4° C. in PBS for up to 2 weeks before use without loss of sieving or photocapture properties.

Single-Cell Immunoblot Assay

Fabricated slides were removed from PBS and excess liquid drained to a corner by gravity and absorbed using a kimwipe (Kimberly-Clark, Irving, Tex.). 1-2 ml of cell suspension was applied evenly across the surface of the slide and allowed to settle on a flat surface within a 100×100 mm petri dish. Settling times varied from 5-30 min, with microwell occupancy monitored by bright field microscopy until single-cell occupancies of roughly 40-50% were achieved. Intermittent, gentle movement of the petri dish every 2-5 min for 10 s was sufficient to ensure cell access to microwells through cell rolling on the gel surface. After settling, slides were lifted to a 10-20° angle from one of the short edges to remove excess cell media, and cells on the surface of the slide were removed by gentle pipetting of 4-5 1 ml aliquots of PBS to the raised edge of the slide surface, with excess buffer removed from the lower edge by vacuum. Slides were placed flat and prepared for cell counting by applying 1 ml of PBS onto the slide. A second plain glass slide was applied to the PBS layer from one short edge to the other to prevent entrapment of bubbles, and lowered to form a "sandwich" of slides. Microwells within the sandwich were imaged using bright field microscopy at 4× magnification (Olympus UPlanFLN, NA 0.13) using 50 ms exposure times at 1×1 pixel binning and a preset position list to guide a mechanical stage (Olympus IX71 inverted fluorescence microscope equipped with iXon+ EMCCD camera, Andor, Belfast, UK; motorized stage, ASI, Eugene, Oreg.; and shuttered mercury lamp light source, X-cite, Lumen Dynamics, Mississauga, Ontario, Canada; controlled by MetaMorph software, Molecular Devices, Sunnyvale, Calif.). All 6,720 features could be imaged in ~4 min.

After cell counting, the top glass slide was removed from the sandwich by sliding gently across the gel layer. The scWestern slide with settled cells was then immediately transferred to a custom 60×100 mm horizontal electrophoresis chamber fabricated from 3 mm-thick perspex plastic. Platinum wire electrodes (0.5 mm diameter, 267228, Sigma-Aldrich) were placed along the long edge of the chamber and interfaced with alligator clips to a standard electrophoresis power supply (Model 250/2.5, BioRad). Slides were temporarily adhered to the bottom face of the chamber using petroleum jelly. 10 ml of a modified RIPA lysis/electrophoresis buffer consisting of 0.5% SDS, 0.1% v/v Triton X-100, 0.25% sodium deoxycholate (D6750, Sigma-Aldrich) in 12.5 mM tris, 96 mM glycine pH 8.3 (0.5× from a 10× stock, 161-0734, BioRad) was poured over the slide to lyse cells. This buffer was supplemented with 1 mM sodium fluoride and sodium orthovanadate for phosphoprotein blots. Lysis proceeded for 10 s with electric field off, followed by application of 200V (E=40 V cm$^{-1}$) for ~30 s. Separations from single EGFP-expressing NSCs were monitored in real time at 10× magnification using a filter set optimized for EGFP (XF100-3, Omega Optical, Brattleboro, Vt.), 4×4 camera binning, 250 ms exposure time. Following separations, slides were immediately exposed for 45 s from above using a UV mercury arc lamp (Lightningcure LC5, Hamamatsu, Bridgewater, N.J.) directed through a Lumatec series 380 liquid light guide with inline UV filter (300-380 nm bandpass, XF1001, Omega Optical) suspended approximately 10 cm above the slide with UV power at the slide surface of ~40 mW cm$^{-2}$ (320-400 nm UV meter; C6080-365, Hamamatsu).

Following separation and photocapture of cell contents, slides were washed using 10 ml of the modified RIPA buffer, followed by 10 ml of TBST (100 mM tris titrated to pH 7.5 with HCl, 150 mM NaCl, 0.1% Tween 20, 9480, EMD Millipore), each for 10 min. Slides could be stored prior to successful immunoprobing for at least 1 wk at 4° C. in TBST.

In FGF stimulation experiments, cells were stimulated between cell-per-well counting and lysis/electrophoresis steps by applying 1 ml of 20 ng/ml FGF-spiked media to the slide surface for the desired stimulation time. Excess media was then drained from the slide surface immediately prior to lysis/electrophoresis.

Purified Protein scWestern Blots

Purified proteins were assayed using a similar protocol to that for single cells. Gel slides were incubated with purified proteins in modified RIPA buffer for 30 min, submerged in fresh modified RIPA for 5 min, and "sandwiched" with a second glass slide to trap proteins within the gel layer. The glass slide sandwich was subjected to electrophoresis, UV-mediated protein capture, washing, and probing as in single cell assays; the top glass layer is removed after the capture step.

Slide Probing, Imaging, and Stripping

Slides were probed with primary and fluorescently labeled secondary antibodies by diffusive delivery in 2×8 well microarray hybridization cassettes (AHC1X16, Arraylt).

Primary antibodies with fold-dilutions employed for single-cell blots (unless otherwise noted) were: rabbit anti-ovalbumin (1:20, ab1221, Abcam), goat anti-GFP (1:20, ab6673, Abcam), rabbit anti-β-tubulin (1:20, ab6046, Abcam), rabbit anti-vimentin (1:20, ab92547, Abcam), rabbit anti-pERK1/2 (1:40, Thr202/Tyr204, 4370, Cell Signaling, Danvers, Mass.), rabbit anti-ERK1/2 (1:20, 4695, Cell Signaling), rabbit anti-pMEK1/2 (1:40, Ser217/Ser221, 9154, Cell Signaling), rabbit anti-MEK1/2 (1:20, 9126, Cell Signaling), goat anti-SOX2 (1:20, sc-17320, Santa Cruz Biotechnology, Santa Cruz, Calif.), mouse anti-nestin (1:20, 611658, BD Biosciences, San Jose, Calif.), goat anti-GFAP (1:20, ab53554, Abcam), mouse anti-βIII-tubulin (1:20, T8578, Sigma-Aldrich, St. Louis, Mo.). Secondary antibodies were Alexa Fluor 488-, 555-, or 647-labeled donkey anti-mouse, rabbit, or goat IgG from Life Technologies (A31571, A31573, A21447, A31570, A31572, A21432, A21202, A21206, A11055), except for the probing of ovalbumin in FIG. 7, which used Alexa Fluor 568-labeled goat anti-rabbit IgG (A-11011, Life Technologies). All were used at the same dilution factor as the corresponding primary antibody.

Figure 7:
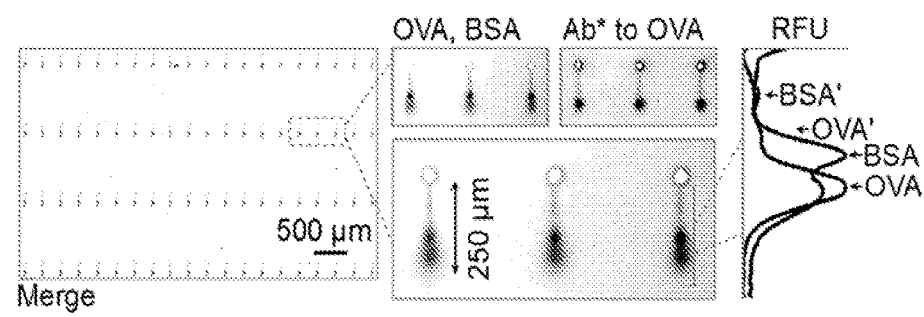
FIG. 7 shows images of in-gel probing of gel-captured purified protein separations according to embodiments of the present disclosure.

For FIG. 7, a mixture of Alexa Fluor 488-labeled OVA and BSA were separated and captured in the sandwich slide configuration over separation distances consistent across the slide (distance of probed OVA band from well lip within block: 167±6.5 μm, ±SD, n=6 blots; between blocks: 164±3.8 μm, ±SD, n=3 blocks). OVA species were probed using a specific primary antibody and an Alexa Fluor 568-labeled goat anti-rabbit IgG secondary antibody, utilizing a separate spectral channel from the Alexa Fluor 488 dye used to label the captured analytes.

Each block of separations was incubated with 40 μl of primary antibody solution diluted to between 1:40 and 1:10 (see Proteins and reagents) in TBST supplemented with 2% bovine serum albumin (BSA, A730, Sigma-Aldrich) for 1 hr. Slides were removed from hybridization cassettes and washed 3 times in 10 ml TBST for 15 min per wash (45 min total). Slides were then similarly probed and washed with fluorescently labeled donkey secondary antibodies at 1:20 dilution in TBST supplemented with 2% BSA. Slides were washed a final time in 10 ml DI water for 5 min and dried under a nitrogen stream. Imaging was conducted using a GenePix 4300A microarray scanner with PMT gains of 400-550 and laser powers of 30-100%, optimized for maximum dynamic range without saturation of immunoblot fluorescence. Filter sets were employed for 3-channel detection using Alexa Fluor 488, 555, and 647-labeled secondary antibodies using 488, 532, and 635 nm lasers, respectively. 12.5 mm diameter emission filters for the 488 and 532 nm spectral channels were from Omega Optical (XF3405 and XF3403, respectively); the 635 nm channel employed a built-in far-red emission filter.

Spectral bleed-through was below noise thresholds of on-target fluorescence line profiles, except for co-probing of ERK or β-tubulin (Alexa Fluor 555-labeled secondary antibody) with EGFP (Alexa Fluor 488-labeled secondary antibody) in FIG. 3 and FIG. 4, respectively. Ratio metrics in FIG. 3d for which ERK blots were affected by EGFP bleed-through above technical noise were discarded from analysis. Ratio metrics in FIG. 4f derived from β-tubulin blots similarly affected by EGFP bleed-through were also discarded. No fluorescence micrographs or derived data sets were fluorescence-compensated for spectral bleed-through.

Stripping of slides was performed via 3 hr incubations in a stripping buffer heated to 50° C. consisting of 2.5% SDS and 1% β-mercaptoethanol (M3148, Sigma-Aldrich) in 62.5 mM tris titrated to pH 6.8 with HCl. Following stripping, slides were washed 3 times in 10 ml TBST for 5 min per wash and stored in TBST at 4° C. until reprobing. This process was found to be robust to extended (~1 month) storage of slides in a dry state prior to stripping.

Single-Cell Immunoblot Data Analysis

Cell-per-well scoring was conducted manually or via custom software designed in-house employing scripts to mate thresholding and particle analysis on the basis of cell size and circularity in Imagej (http://rsbweb.nih.gov/ij/) to downstream gating to identify microwells containing single cells in R (http://www.r-project.org).

To quantify the performance of automated cells-per-well scoring, precision=tp/(tp+fp) and sensitivity=tp/(tp+fn) were calculated, where tp is the number of wells scored as containing single cells that actually contained single cells, fp is the number of wells scored as containing single cells that did not contain a single cell, and fn is the number of wells scored as not containing single cells that actually contained single cells. Precision=1 meant that all wells scored as containing single cells actually contained single cells. Sensitivity=1 meant that all wells actually containing single cells were scored as containing single cells. Precision and sensitivity metrics were 0.90±0.09 (±SD, n=56 blocks of 420 wells on 8 separate slides) and 0.68±0.17 respectively, reflecting stringent selection of single cell wells at the expense of the total number of wells included in downstream analysis.

Fluorescence images from the GenePix scanner were registered using landmark correspondences in Fiji (http://fiji.sc/Fiji). A custom script extracted line profiles from grids of regions of interest (ROIs) from each fluorescence image. Line profiles were background subtracted using linear interpolation between points set to the approximate boundaries of peaks of interest. Data quality control was performed by visually reviewing immunoblot ROIs flagged due to outlying line profiles. Immunoblots that were clearly affected by the presence of e.g., autofluorescent particulates were discarded from data sets, as were zero cell-per-well blots incorrectly scored as single-cell blots that did not contain β-tubulin loading control signals above technical noise.

Total areas under peaks (AUCs) of interest (or metrics derived from them, such as AUC ratios and calibrated AUCs) were transformed, where applicable, using the function $AUC_t = \text{arcsin h}(AUC/F)$, where $AUC_t$ is the arcsin h-transformed value and F is a cofactor prescribing the transition from linear to log-like behavior. The value of F was optimized by setting it according to $F=\mu_{ones,below}+3\sigma_{ones,below}$, where $\mu_{ones,below}$ and $\sigma_{ones,below}$ are the mean and standard deviation of the set of single cell-per-well immunoblots with AUCs (or metrics) below a technical noise threshold. The technical noise threshold T was set at $T=\mu_{zeros}+3\sigma_{zeros}$, where $\mu_{zeros}$ and $\sigma_{zeros}$ are the mean and standard deviation of the AUCs or metric values from zero cell-per-well immunoblots in a given experiment. Where applicable, immunoblots with AUCs in the numerator of ratio metrics falling below T were flagged to display as such when plotted. Immunoblots with AUCs below T in the denominator were discarded from data sets.

Statistical Analysis

Non-parametric comparison of single-cell blot data (single comparisons only) was performed using the Mann-Whitney U test in conjunction with Shapiro-Wilk and Levine tests for normality and equality of variance, respectively, in SPSS v.21 software (IBM, Armonk, N.Y.).

Single-Cell Immunoblot Calibration

A conceptual overview and schematics of direct and indirect calibration assays are provided below and in FIG. 8.

Figure 8:
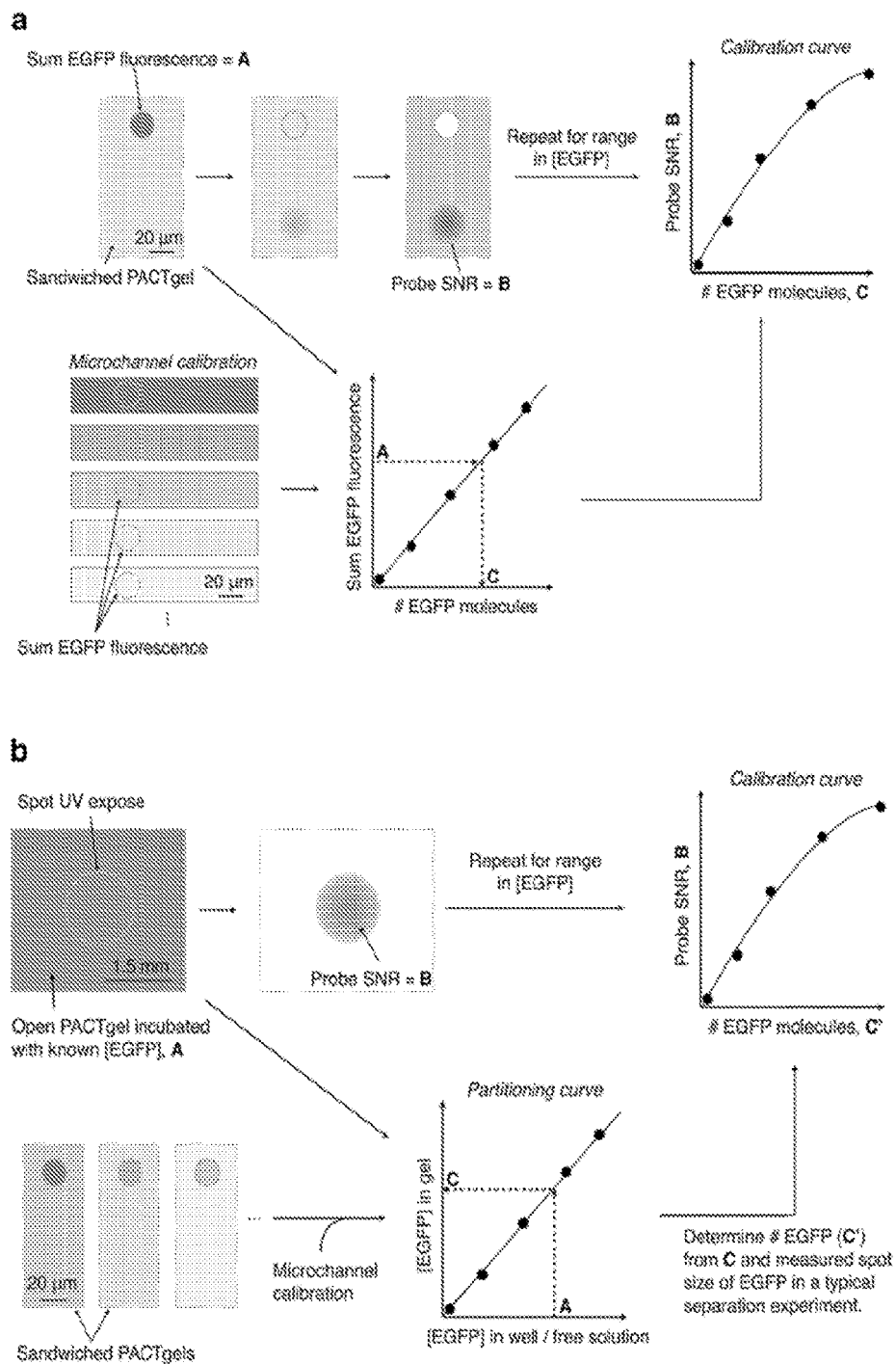
FIGS. 8a and 8b show direct and indirect calibration procedures for purified EGFP in the single-cell immunoblot calibration in Example 2, according to embodiments of the present disclosure.
Figure 9:
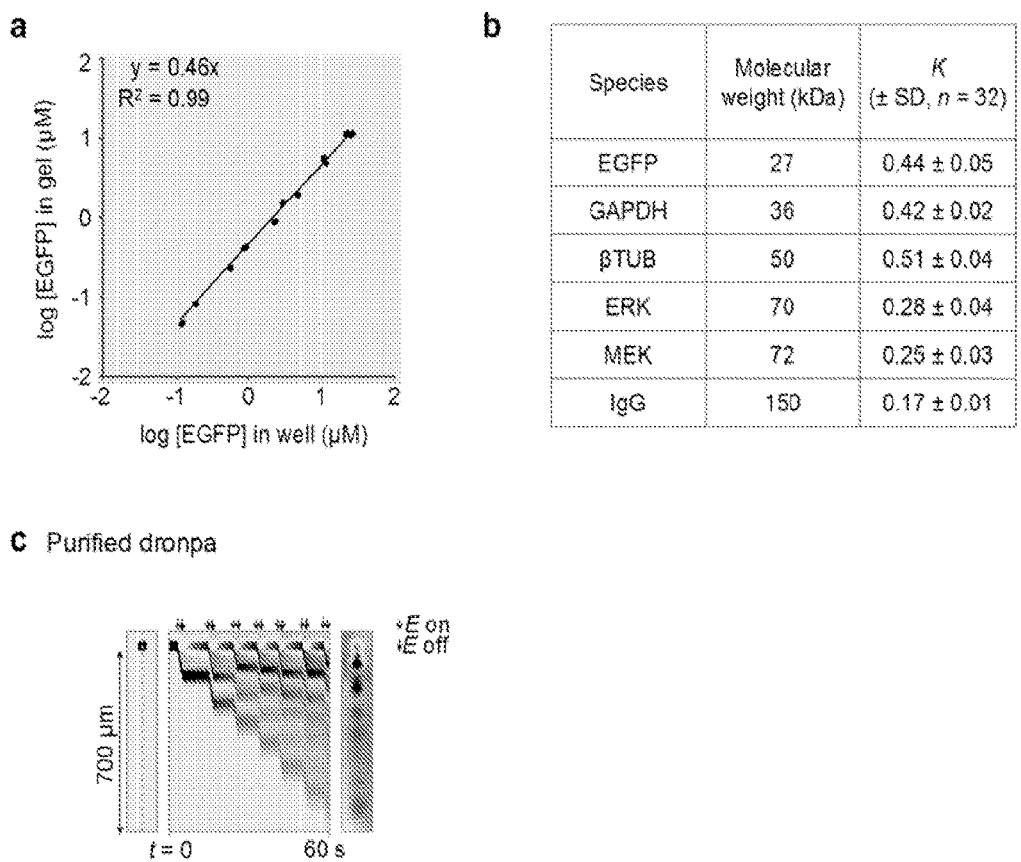
FIG. 9a shows a partitioning curve for EGFP determined for microwell blocks in a 8% T gel sheet incubated with a dilution series of EGFP in modified RIPA buffer via $K=([EGFP]_{gel}-[EGFP]_{gel,bg})/([EGFP]_{well}-[EGFP]_{well,bg})$, where $[EGFP]_{gel}$ and $[EGFP]_{well}$ were in-gel and in-well concentrations of EGFP at equilibrium determined by fluorescence calibration in a separate microchannel of 30 μm depth, according to embodiments of the present disclosure. $[EGFP]_{gel,bg}$ and $[EGFP]_{well,bg}$ correct for the background fluorescence of the scWestern slide prior to incubation with the EGFP solutions.
FIG. 9b shows partition coefficients for several Alexa Fluor 568-labeled proteins determined as in (FIG. 9a), except "IgG", which was for Alexa Fluor 647-labeled donkey anti-rabbit IgG; n is for separate microwells in single experiments for each target.
FIG. 9c shows repeated injections of the fluorescent protein dronpa from a coverglass-enclosed, 50 μm diameter microwell in an 8% T scWestern gel sheet incubated with 1 μM dronpa in modified RIPA buffer for 30 min. Partitioning of dronpa into the microwell allowed repeated injections against a background gel concentration of dronpa.
Figure 10:
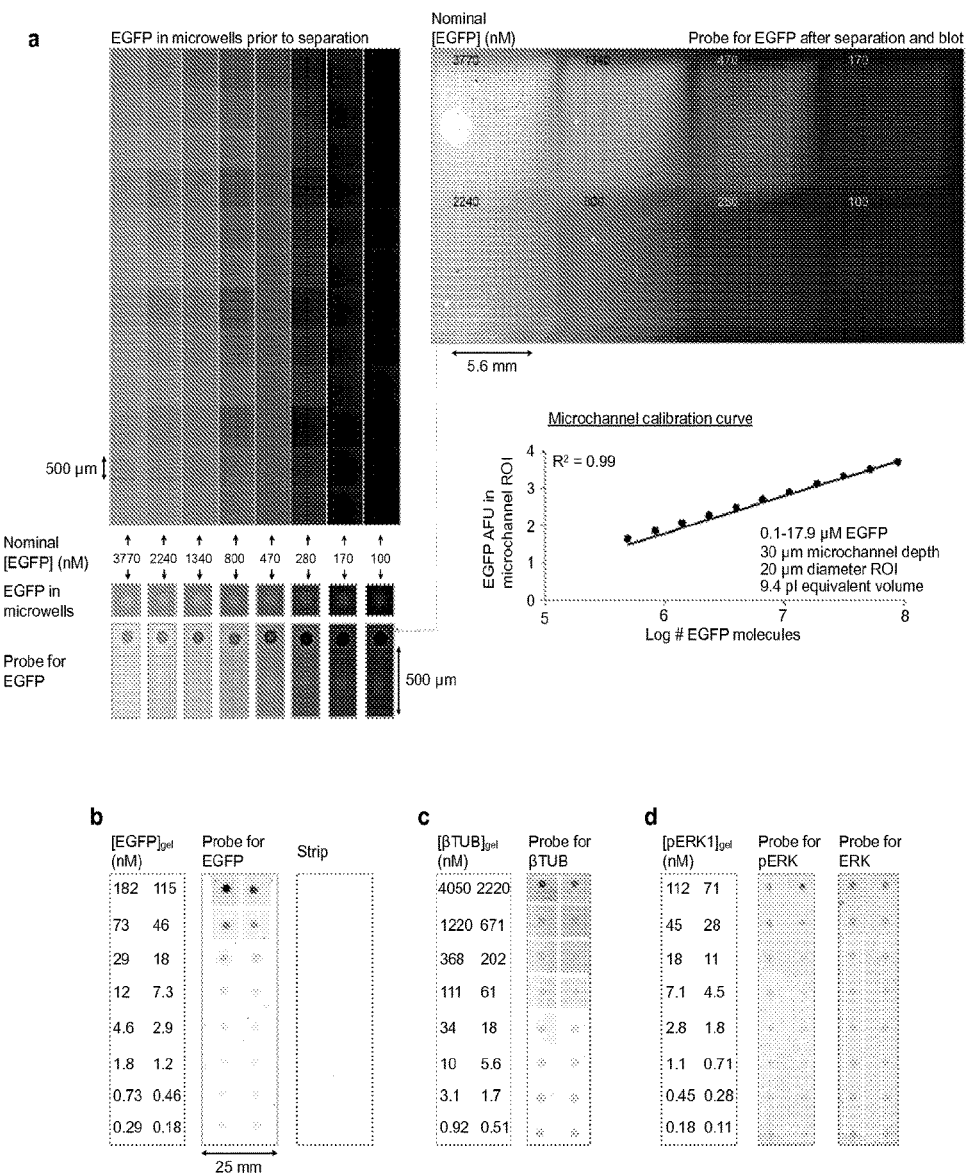
FIGS. 10a and 10b show direct and indirect calibration slides used for calibration curves in FIG. 2d.
FIGS. 10c and 10d show similar indirect calibration slides for purified β-tubulin (Alexa Fluor 647-labeled secondary antibody) and ERK1/pERK1 (both Alexa Fluor 555-labeled secondary antibody; slide stripped between pERK and ERK probing).

In order to determine the linear dynamic range and limit of detection of the single-cell immunoblot assay, two methods were used to calibrate it using purified proteins (FIG. 2d, and FIGS. 8 and 10). The first ("direct") method relied on direct measurement of EGFP concentrations in microwells immediately before separation, capture and probing, for wells incubated with a range in nominal concentrations of EGFP. The endpoint probe fluorescence was plotted on a curve against the number of EGFP molecules originally present in the corresponding microwell, inferred by calibrating the EGFP fluorescence measurements against those made in microchannels of the same depth as the thickness of the scWestern gel sheet (30 μm). The second ("indirect") method did not require direct measurement of the protein molecules present within the microwells, and instead used large spot exposures to capture purified proteins from free solution, where their gel concentrations were inferred from partition coefficient measurements (FIGS. 9a-c). The end result was a calibration curve of the fluorescent probe readout for a given protein against the number of protein molecules present within a spot roughly the size of that expected if the captured protein had originated from a single-cell blot band. Thus, lower concentrations of proteins than can be directly observed can be used in the indirect calibration curve, since the gel concentration of a given protein is known from the nominal solution concentration and the partition coefficient.

The efficacy of antibody stripping was verified for the indirect EGFP calibration slide, showing residual signal at the detection threshold (SNR=3) for the majority of the calibration range (from ~$10^4$-$10^6$ molecules), and fold-reductions in SNR of >10 above this range (FIG. 2d, and FIG. 10).

For "direct" calibration of EGFP, an 8-aliquot dilution series (40 μl per aliquot) of EGFP in modified RIPA buffer supplemented with 4 μM BSA (approximating total protein levels in single cell blots) was added to distinct wells of scWestern slides in the ArrayIt hybridization cassette (FIG. 10). Slides were sandwiched and assayed as for purified protein blots (see Purified protein scWestern blots) with one additional step. A subset of microwells in each block were imaged for EGFP fluorescence (EGFP cube, 10× Olympus UPlanFLN NA 0.3 objective, 200 ms exposure time, 1×1 pixel binning) immediately prior to the electrophoresis step using a preset position list to guide the mechanical stage on the IX71 fluorescence microscope. Partition coefficients across the concentration range were determined from these images according to $K=([EGFP]_{gel}-[EGFP]_{gel,bg})/([EGFP]_{well}-[EGFP]_{well,bg})$, where $[EGFP]_{gel}$ and $[EGFP]_{well}$ are in-gel and in-well concentrations of EGFP at equilibrium determined by fluorescence calibration in a separate microfluidic channel of 30 μm depth (FIG. 9). Custom straight-channel microfluidic chips were fabricated in soda lime glass using standard wet-etching processes (PerkinElmer, Waltham, Mass.). $[EGFP]_{gel,bg}$ and $[EGFP]_{well,bg}$ correct for the background fluorescence of the scWestern slide prior to incubation with the EGFP solutions. The number of molecules of EGFP in each microwell voxel was also estimated from these data, assuming cylindrical microwells of nominal dimensions: 20 μm diameter, 30 μm depth (9.4 μl volume).

"Indirect" calibration was performed by capturing to the scWestern gel sheet and probing a dilution series of a given purified protein in modified RIPA supplemented with 4 μM BSA in the absence of an electrophoresis step (FIGS. 8 and 10). Spot UV exposures were applied to the underside of the slide within each microwell block via the 10× objective for 45 s each on the Olympus IX71 fluorescence microscope through a custom UV-longpass filter set (excitation 300-380 nm, emission>410 nm; XF1001, XF3097; Omega Optical) with a UV power at the slide surface of ~40 mW cm$^{-2}$ (320-400 nm UV meter; C6080-365, Hamamatsu). The in-gel concentrations of purified proteins captured in this manner were determined from separate partition coefficient measurements using Alexa Fluor 568-labeled aliquots of each protein (FIG. 9). Indirect calibration of EGFP reports molecule number using the inferred in-gel concentrations for a voxel size equivalent to that of a typical blotted EGFP band from a single cell blot experiment (45×45 μm in area, 30 μm in depth). Probe AFU and SNR values in indirect calibration data were corrected for fluorescence background caused by non-specific probing of UV-exposed gel spots in the absence of calibration standard.

Determination of Bulk Buffer Velocity During in-Microwell Lysis

Figure 11:
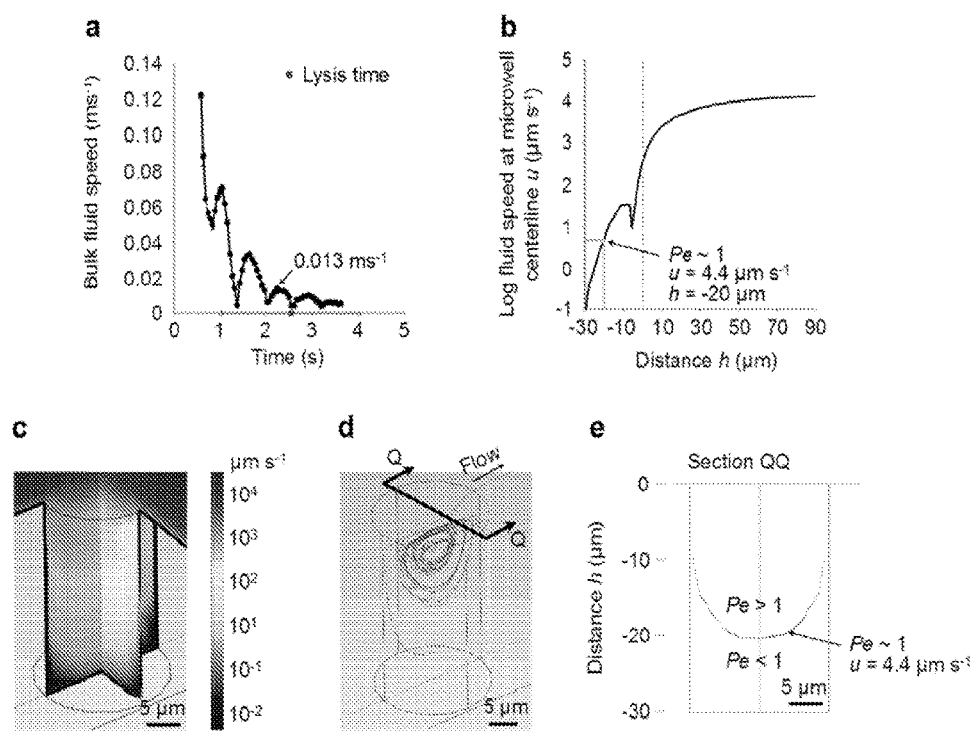
FIG. 11a shows a graph of measured bulk buffer speed during pouring into the scWestern electrophoresis chamber by particle image velocimetry. Lysis time is also shown for context (±SD, n=6 cells). The maximum bulk velocity in the vicinity of the mean lysis time was 0.013 ms$^{-1}$, and was used for fluid flow simulations in FIGS. 11b-11e.
FIGS. 11b-11d show a COMSOL model of unidirectional, steady-state laminar flow during pouring of water over a 20 μm diameter microwell in a 30 μm-thick scWestern gel film with a bulk fluid velocity of 0.013 ms$^{-1}$. Note the presence of a vortex in the well parallel to the bulk flow direction that is traced by streamlines representing the movement of massless, non-buoyant particles from starting locations at 5, 10, 15, 20, and 25 μm into the well. Flow boundary conditions on the well surfaces were "no slip".
FIG. 11e shows a centerline slice transverse to the flow direction for the model velocity distribution; the u=4.4 μm s$^{-1}$ isotach demarcates regions of the well in which mass transport was diffusively (Pe<1) or advectively (Pe>1) dominated during cell lysis.

Bulk maximum flow speeds during lysis (ignoring vector information) were estimated by wide field fluorescence microscopy (4× objective, EGFP filter set) during pouring of a fluorescent microbead-spiked RIPA buffer over a scWestern slide ($10^5$ beads/ml) at an exposure time of 10 ms (FIG. 11). Velocities were extracted from fluorescence streaks caused by movement of beads in the horizontal plane over the exposure period, with the objective focused ~1 mm above the center of the scWestern slide plane to observe bulk fluid behavior.

COMSOL Fluid Modeling

Fluid flow in scWesterm microwells was modeled in COMSOL Multiphysics 4.2a (FIG. 11). COMSOL modeling showed a monotonic decrease in local fluid velocity as a function of vertical distance into the microwell beneath the gel surface, except in the vicinity of a recirculating eddy near the top of the well. Beneath this, a critical local fluid speed of 4.4 µm $s^{-1}$ giving a Peclet number of 1 was determined via Pe=Lu/D, where the characteristic length L is the microwell diameter (20 µm), and u is the local fluid velocity. $D=k_BT/6\pi\mu r_H=8.8\times10^{-11}$ $m^2$ $s^{-1}$ is the free-solution diffusivity of EGFP as a low molecular weight model analyte, with the Boltzmann constant $k_B=1.38\times10^{-23}$ $m^2$ kg $s^{-2}$ $K^{-1}$, temperature T=293.15 K, dynamic viscosity of water µ=0.001 kg $m^{-1}$ $s^{-1}$, hydrodynamic radius $r_H$=0.595 $(M_w)^{0.427}$=2.43 nm ($M_w$=27 kDa, the molecular weight of EGFP).

The isotach at this critical speed of 4.4 µm $s^{-1}$ approximately demarcates regions of diffusively and advectively-dominated mass transport regimes during lysis buffer pouring for microwell coordinates below (Pe<1) and above (Pe>1) it in the z direction, respectively (FIG. 11).

Bulk flow above microwells was simulated as steady-state laminar flow of water in a square channel of cross-section 100×100 µm. The top and side walls of the channel were set to a slip boundary condition. The bottom wall of the channel and the microwell walls were set to no-slip. Inlet velocity was set to 0.0087 $ms^{-1}$ to achieve a maximum bulk flow velocity of 0.013 $ms^{-1}$. Outlet pressure was set to 0. Microwell recirculation flow was visualized by Particle Tracing.

Flow Cytometry

For flow cytometry for EGFP expression, EGFP NSCs and uninfected NSCs were detached with accutase, fixed by suspension in 4% paraformaldehyde (P6148, Sigma-Aldrich) for 15 minutes, and then blocked and permeabilized with flow staining buffer (5% donkey serum with 1 mg/mL saponin; D9663 and 47036, Sigma-Aldrich; in PBS) for 15 minutes. Cells were incubated with goat anti-GFP (1:100; see Slide probing, imaging, and stripping. for product details) in flow staining buffer for 1 hour; followed by incubation with Alexa Fluor 555-labeled donkey anti-goat IgG (1:100) in flow staining buffer for 1 hour. Flow cytometry was performed using a Millipore EasyCyte 6HT-2L.

Conventional Western Blotting

Figure 3:
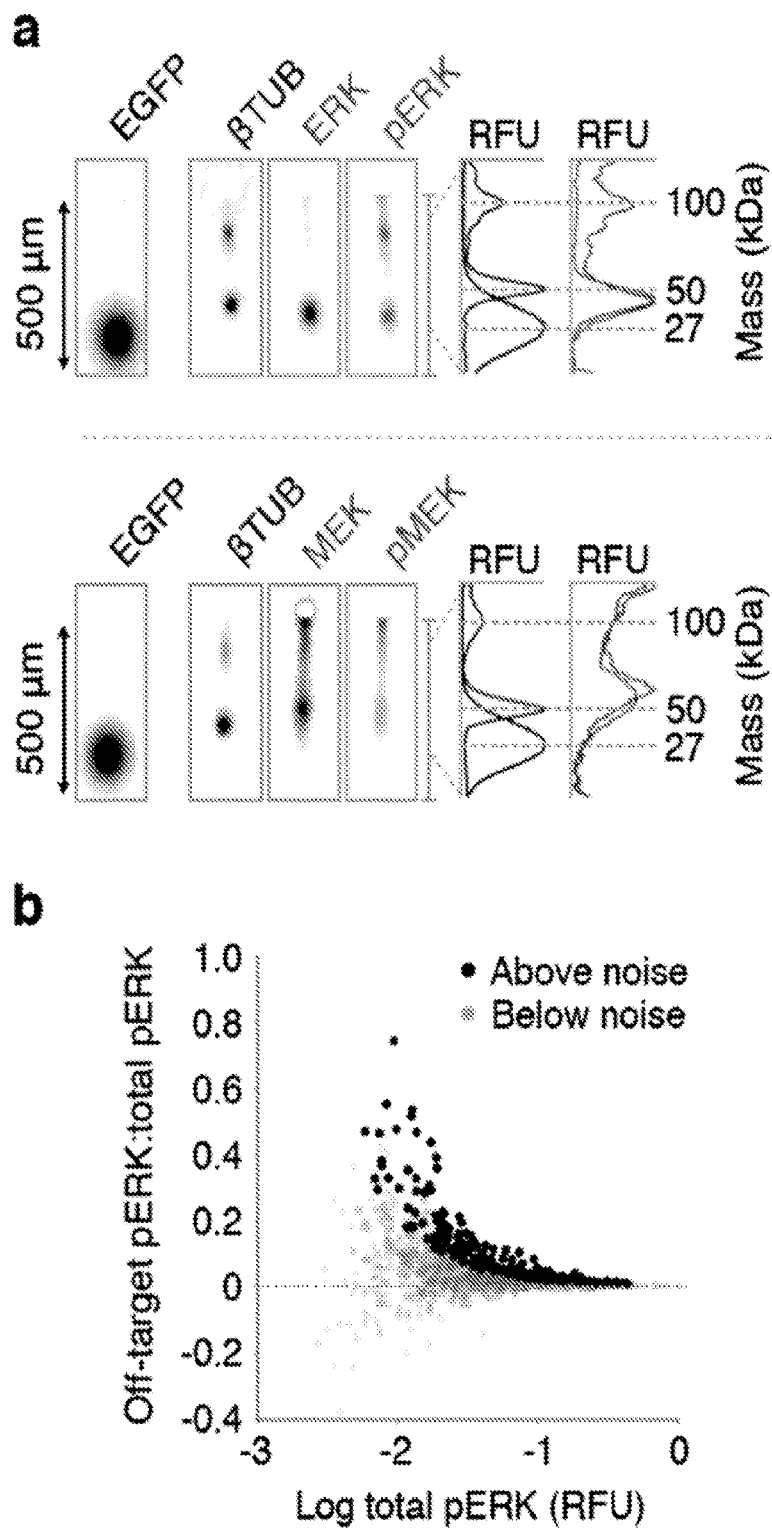
FIG. 3a shows single cell western blots that captured fibroblast growth factor (FGF) signaling pathway dynamics and minimized contribution of off-target antibody probing by gating on molecular mass, according to embodiments of the present disclosure.
FIG. 3b shows a graph of the contribution of probing at the 103 kDa off-target band of pERK to its total fluorescence signal, according to embodiments of the present disclosure.
FIG. 3c shows conventional western blots of ~30,000 cells per lane for 20 ng/ml FGF stimulation of rat NSCs after a 16 hr starve, according to embodiments of the present disclosure.
FIG. 3d shows fold-change violin plots of specific pERK and pMEK band fluorescence as ratios to total ERK and MEK, respectively, upon stimulation of microwell-seeded rat NSCs with 20 ng/ml FGF. Note arcsin h-transformed scales, according to embodiments of the present disclosure. Plots were overlayed with corresponding data determined by densitometry from conventional western blots in FIG. 3d: Data from blots for which ratio metrics were below the technical noise threshold in pERK/pMEK are indicated. *** indicates P<0.001.
FIG. 3e shows complementary ERK and MEK phosphorylation data via high-throughput immunocytochemistry, according to embodiments of the present disclosure. Cells were co-probed for pERK/ERK and pMEK/MEK pairs; phosphorylated targets were probed using an Alexa Fluor 555-labeled secondary antibody, and total targets with Alexa Fluor 647-. pERK, ERK, and MEK were localized to the cytoplasm, pMEK antibody showed improper nuclear localization.

For the signaling study in FIG. 3, EGFP NSCs were seeded at 2.5×105 cells per well in a 6-well plate. Cells were FGF-starved for 16 hours, incubated with 20 ng/mL FGF for the desired stimulation time, and lysed in RIPA buffer (50 mM tris, 150 mM NaCl, 1% NP-40, 0.5% sodium deoxycholate, 0.1% SDS, pH 8) containing protease and phosphatase inhibitor cocktails (87786 and 78420, ThermoFisher Scientific) and 10 mg/mL PMSF (78830, Sigma-Aldrich). For the differentiation assay, EGFP NSCs were seeded at 5×105 cells per dish in 6 cm dishes. Day 0 differentiated cells were lysed the following day; day 6 differentiated cells were cultured in differentiation media (DMEM/F12/N2, 0.5 ng/mL FGF, 1 µM RA, 1% FBS) for 6 days and then lysed. Cell lysates of equal total protein concentrations determined by a bicinchoninic acid assay (23227, ThermoFisher Scientific) were electrophoretically separated on SDS-PAGE gels and transferred onto nitrocellulose membranes using standard methods. Blots were blocked for 1 hour in TBS with 0.1% Tween-20 (BP337, ThermoFisher Scientific) and 3% BSA (A4503, Sigma-Aldrich) for phoshoprotein antibodies or 5% non-fat powdered milk for all other antibodies. Blots were probed overnight with primary antibodies in the same blocking buffer: rabbit anti-pERK1/2 (1:2000), rabbit anti-ERK1/2 (1:1000), rabbit anti-pMEK1/2 (1:1000), rabbit anti-MEK1/2 (1:1000), goat anti-SOX2 (1:500), mouse anti-nestin (1:1000), goat anti-GFAP (1:1000), mouse anti-βIII-tubulin (1:2000), rabbit anti-β-tubulin (1:500); followed by 1 hour incubation with appropriate horseradish peroxidase-conjugated secondary antibodies: mouse anti-goat HRP (1:5000, 31400), goat anti-mouse HRP (1:10000, 32430), goat anti-rabbit HRP (1:10000, 32460), all from Thermo-Fisher Scientific. Protein bands were detected using SuperSignal West Dura Chemiluminescent Substrate (34076, ThermoFisher Scientific) and blots were digitally imaged on a ChemiDoc XRS+ Imaging System (BioRad). Blots were stripped in a solution of 3% acetic acid, 0.5M NaCl, pH 2.5 for 10 minutes, neutralized with 0.5M NaOH for 1 minute, and then re-probed as needed. Blot densitometry was performed in ImageJ by measuring background-subtracted ROI intensities.

Immunocytochemistry

For the signaling study in FIG. 3, EGFP NSCs were seeded at 5×103 cells per well in a 96-well plate. Cells were FGF starved and stimulated as described for conventional western blotting. For the differentiation assay in standard cell culture conditions, EGFP NSCs were seeded at 4×104 cells per well in a 24-well plate and differentiated. For scWestern microwells, EGFP NSCs were differentiated in culture plates, suspended on the appropriate day, settled into scWestern slides, and processed within ArrayIt hybridization cassettes with a similar workflow to that used for culture plates. Cell cultures and settled cells were fixed with 4% paraformaldehyde for 15 minutes, and then blocked and permeabilized with staining buffer (5% donkey serum with 0.3% Triton-X100 in PBS) for 30 minutes. Cultures and cells were incubated 24-48 hours with combinations of primary antibodies in staining buffer: rabbit anti-pERK1/2 (1:200; see Slide probing, imaging, and stripping. for product details), mouse anti-ERK1/2 (1:50, 4696, Cell Signaling), rabbit anti-pMEK1/2 (1:200), mouse anti-MEK1/2 (1:25, 4694, Cell Signaling), goat anti-SOX2 (1:100), mouse anti-nestin (1:200), goat anti-GFAP (1:500), mouse anti-βIII-tubulin (1:500); followed by 2 hour incubations with appropriate Cy3-, Alexa Fluor 555-, and 647-labeled donkey anti-mouse, rabbit, or goat IgG secondary antibodies (1:250, Life Technologies; 15-165-150, 715-605-150, 711-605-152, 705-605-147, Jackson ImmunoResearch, West Grove, Pa.) in staining buffer, with DAPI as a nuclear counterstain (5 µg/mL, D1306, Life Technologies). Cell cultures were imaged using a Nikon Eclipse Ti inverted fluorescence microscope (Nikon Instruments, Melville, N.Y.) or an ImageXpress Micro XL Widefield High Content Screening System (Molecular Devices, Sunnyvale, Calif.). In-microwell cells were imaged using the Olympus IX71 microscope (see Single-cell immunoblot assay.).

Confocal images were obtained on a BX51W1 microscope (Olympus, Center Valley, Pa.) with swept-field confocal optics (Prairie Technologies, Middleton, Wis.) and analyzed with Icy bioinformatics software (Quantitative Image Analysis Unit, Institut Pasteur, Paris, France). For confocal imaging of differentiated cells in scWestern microwells in FIG. 4c, rabbit anti-GFAP (1:500, ab7260, Abcam) was used; all other antibody reagents were identical to those listed.

Immunochemistry Data Analysis

For the signaling study in FIG. 3a, cells were identified via custom ImageJ scripts using thresholding and particle analysis to locate DAPI-stained nuclei. Single cells for analysis were isolated and selected by gating for distance to nearest neighbor and uniformity of background signal in R. Fluorescence was quantified by summing pixel intensities of a background-subtracted 75×75 pixel ROI around each single cell. Approximately 50% of pixels in each ROI consisted of background signal, which was Gaussian in distribution. The intensity value with highest pixel count was taken to be the mean background intensity and used for background subtraction for individual ROIs. A noise threshold was set to $T=3\sigma_{bg}$, where $\sigma_{bg}$ is the maximum standard deviation of background signal intensity in the fluorescence micrographs at each experimental condition. Measurements with fluorescence below T in the numerator were identified as such in plotted data. Measurements with fluorescence below T in the denominator were discarded from data sets.

Figure 4:
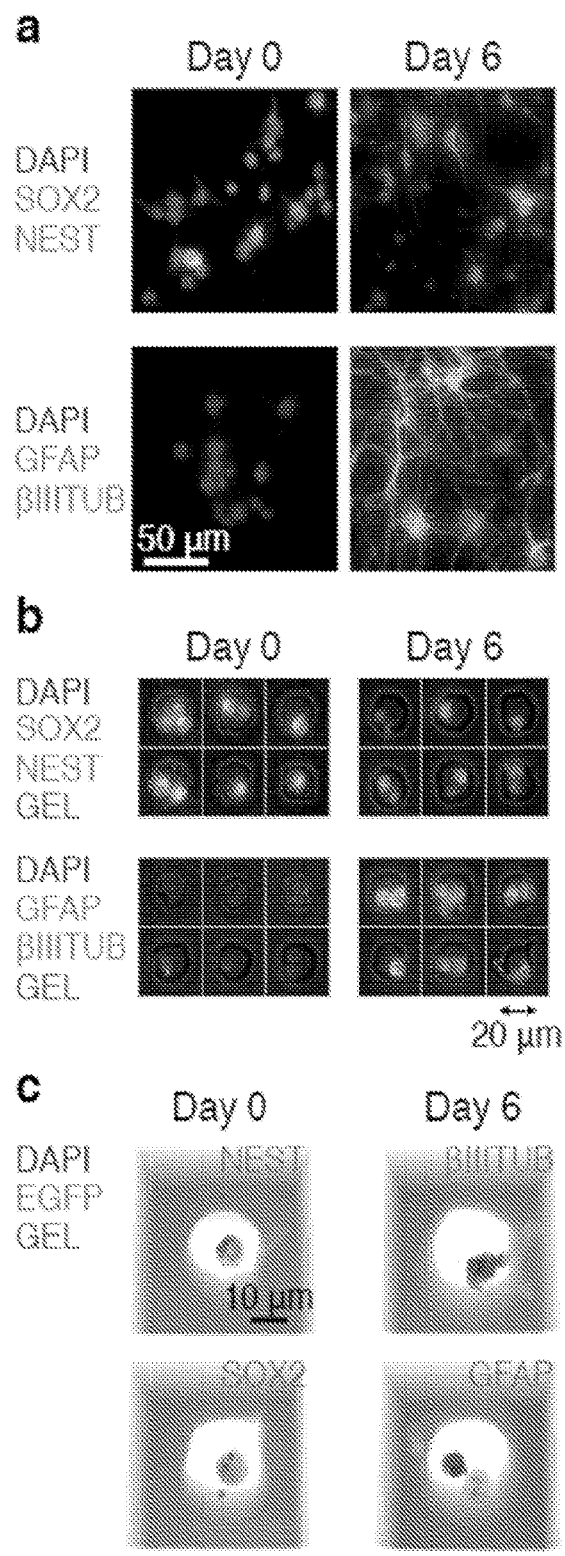
FIG. 4a shows images of single cell western blots used to track NSC differentiation dynamics in the presence of a strong morphological gradient, according to embodiments of the present disclosure.
FIG. 4b shows fluorescence micrographs for NSCs seeded into scWestern microwells, fixed and stained as in FIG. 4a, according to embodiments of the present disclosure. Bright field images were overlaid to highlight microwell edges.
FIG. 4c shows confocal images of fixed and stained stem (NEST+, SOX2+), neuron (βIIITUB+) and astrocyte (GFAP+) cell types settled within a rhodamine-tagged gel (GEL), according to embodiments of the present disclosure.
FIG. 4d shows fluorescence micrographs and line profiles for scWestern blots of neural stem cell and differentiation markers (RFU: relative fluorescence units), according to embodiments of the present disclosure. SOX2 (Alexa Fluor 555-labeled secondary antibody) and nestin (Alexa Fluor 488-) were co-probed in separate blocks as GFAP (Alexa Fluor 555-) and βIIITUB (Alexa Fluor 488-); both sets of blocks were then stripped and co-probed for βTUB (Alexa Fluor 555-) and EGFP (Alexa Fluor 488-). Sets of blots from each day were from the same separation, except EGFP blots, which were from a separation in the same row of the array as the corresponding set.
FIG. 4e shows conventional western blots of ~30,000 cells per lane for markers at days 0 and 6 of differentiation, according to embodiments of the present disclosure.
FIG. 4f shows plots of stem cell and differentiation marker total scWestern blot fluorescence normalized by βTUB blot fluorescence across the 6 day differentiation experiment. Note arcsin h-transformed scales, according to embodiments of the present disclosure.

Fluorescence micrographs from ICC experiments in culture plates and scWestern microwells for the differentiation experiment in FIG. 4 were manually scored for marker expression according to arbitrarily determined fluorescence thresholds in ImageJ. Different, blinded researchers conducted ICC counting and scWestern marker expression analyses.

Results

Design and Characterization of scWestern Blot Arrays for Single Cell Analysis

Single cell western (scWestern) blotting was performed on a microscope slide coated with a thin photoactivatable polyacrylamide (PA) gel micropatterned with an array of 6,720 microwells (FIG. 1). The scWestern array included thousands of microwells (20 µm diameter, 30 µm deep) patterned in a 30 µm-thick photoactive polyacrylamide gel seated on a glass microscope slide. The array included 16 blocks of 14×30 microwells cast against an SU-8 photoresist master fabricated by soft lithography (FIG. 1a).

The microwells (20 µm diameter) were patterned during polymerization of a 30 µm-thick PA gel against a silicon wafer studded with SU-8 microposts (FIG. 1b). To allow for concurrent western blotting of thousands of single cells, the scWestern array and assay designs integrated all six western blot stages in a dense array format and allowed for manipulation of thousands of cells concurrently. Three attributes underpin the scWestern array design and form the basis for the single cell western blotting capability.

Figure 12:
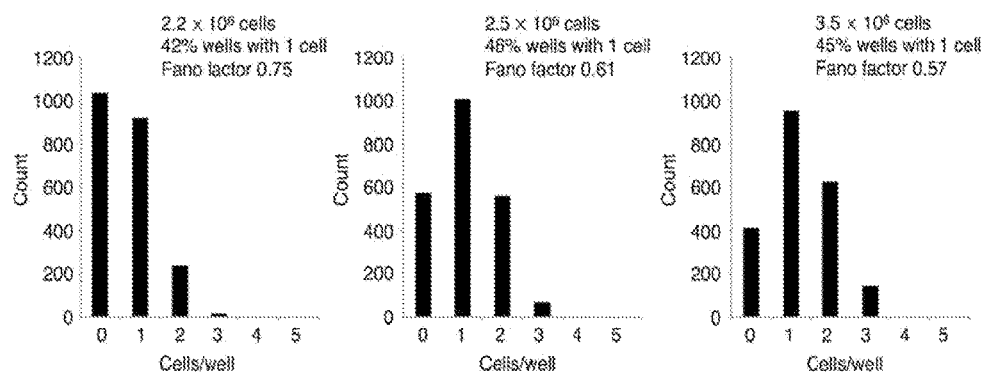
FIG. 12 shows graphs of cell-per-well counts for rat neural stem cells, according to embodiments of the present disclosure. Rat neural stem cells were settled into 2,240 scWestern microwells of nominal dimensions 20 μm in diameter and 30 μm in depth for 5 min and counted by hand from bright field micrographs for 3 cell densities in the original suspension. Single cell-per-well occupancies were in the 40-50% range, with fano factors ($\sigma^2/\mu$) of between 0.55 and 0.75, indicating departure from a Poissonian seeding distribution, likely due to restricted seeding of more than 4 cells per well.

First, the scWestern array was addressed globally, in contrast to localized actuation of each of thousands of microwells. For cell seeding, passive gravity-driven cell settling was used. A suspension of single cells was settled onto the scWestern array, leading to capture of 0-4 cells per microwell in settling times of 5-10 minutes. For rat neural stem cell densities of 1,000-1,800 cells mm$^{-2}$ slide area (2-3.5×10$^6$ cells total), single cells in 40-50% of the wells were observed (FIG. 12). Lysis of the settled cells was used for subsequent protein electrophoresis. To globally lyse cells, bulk buffer exchange over the scWestern array surface was used. A RIPA buffer modified to maximize solubilization of intracellular proteins while maintaining a suitable conductivity for subsequent electrophoresis was used. The RIPA buffer provided denaturing, non-reducing conditions. Cell lysis was observed in microwells in 2.6±1.5 s (±SD, n=6 cells), followed by protein extraction from cells within ~10 s (FIG. 1e). Pouring lysis buffer over the open microwells did not advectively purge cell contents from the microwells (FIG. 11). Fluid flow in the microwells was simulated at the mean cell lysis time. The simulations indicated a recirculating flow in the first ~20 µm of microwell depth with a nearly stagnant flow occupying in the bottom 10 µm of the microwells (with Péclet number Pe<1). As settled cells were largely shielded from advective transport, diffusion was likely largely responsible for protein loss from the wells. Empirically, combined EGFP protein losses of 40.2±3.6% were measured during lysis (±SD, n=3 microwells from 3 separate slides). In FIG. 1e, distinct fluorescent dyes on each secondary antibody enabled multiplexed target analysis (EGFP: Alexa Fluor 488-labeled secondary antibody, βTUB: Alexa Fluor 555-). Stripping and reprobing via chemical stripping allowed scWestern blotting of vimentin in dimeric form (VIM', 107 kDa; Alexa Fluor 555-). Antibody dilution factors for all figures are previously set forth above.

Second, to achieve a high density microwell array layout, the array was optimized for short separation-distance protein electrophoresis. In the scWestern array, the pitch between microwells determines the available separation distance. To initiate and drive electrophoresis after cell lysis, an electric field was applied across the submerged scWestern slide. The applied field drove the proteins through the microwell walls and into the thin gel sheet, which initiated polyacrylamide gel electrophoresis (PAGE). To understand PAGE performance in this architecture, a model solution of fluorescently labeled ladder proteins (27-132 kDa, FIG. 1d) that partitioned into the microwells was assayed (FIG. 9).

Partitioning of proteins between free solution and polyacrylamide gels—Particles including proteins were expected to partition between dense hydrogel networks and free solution according to a partition coefficient, K, a ratio of $c_l$ and $c_b$, the local gel and bulk free solution protein concentrations:

$$K = \frac{c_\ell}{c_b} = e^{-\phi\left(1+\frac{a}{a_f}\right)^2} \quad (1)$$

Where $\phi$ is the volume fraction of the polymer network, a is the Stokes-Einstein radius of the protein and $a_f$ is the polymer fiber radius. A demonstration of equilibrium partitioning and repeated injections of the fluorescent protein dronpa from scWestern microwells is shown in FIG. 9, along with measured partition coefficients for a range of purified proteins targets of interest.

Figure 13:
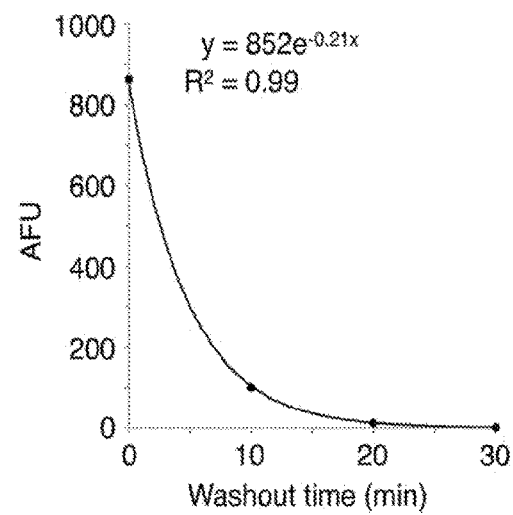
FIG. 13 shows a graph of antibody transport kinetics across scWestern gel films, according to embodiments of the present disclosure. Residual slide fluorescence was determined by fluorescence microscopy for TBST washing of an 80 μm-thick gel layer after incubation with 100 nM Alexa Fluor 568-labeled anti-ovalbumin in free solution for 30 min. The time constant τ=4.8 min for antibody equilibration with the scWestern gel layer was the inverse of the exponent of the fit.

Given the anticipated partitioning effect, which was expected to be exacerbated by the large (~150 kDa) size of probe antibodies, the equilibration time of probe antibodies in an 80 µm-thick scWestern gel layer was determined (FIG. 13). After incubating a fluorescently labeled primary antibody in the free solution above a gel-coated slide for more than 30 min, the slide was washed in TBST and imaged periodically. As antibody left the slide by diffusion, an exponential decay in the slide fluorescence was observed with a time constant τ of roughly 5 min, and the time for complete washout of ~4τ=20 min compared well with an estimated diffusion time $t \sim x^2/4D=27$ min. The gel layers were typically 30 µm thick to minimize the incidence of vertical stacking of multiple cells within the microwells by more closely matching the dimension of a cell. An antibody diffusion time of roughly 4 min was expected.

This experiment indicated that rapid equilibration of probe antibodies with the scWestern gel can be achieved during probing and washing, given its microscale thickness, although the solution concentration of probe was increased to compensate for the effect of partitioning in reducing the gel concentration of the probe by a measured partition coefficient of 0.17 with respect to its bulk solution concentration (FIG. 9).

Figure 14:
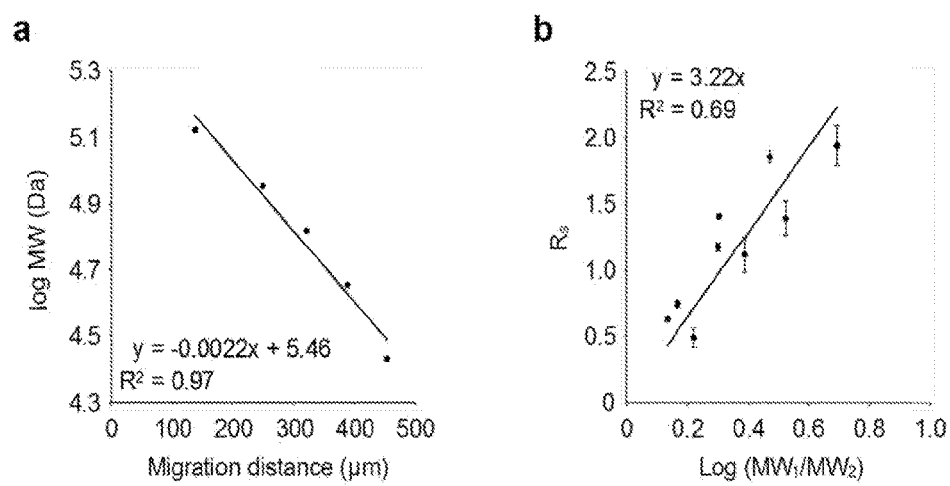
FIGS. 14a and 14b show graphs of separation properties of fluorescently labeled proteins in scWestern gel sheets, according to embodiments of the present disclosure.

During electrophoresis stacking of proteins against the rim of the microwells was observed followed by PAGE. Under denaturing, non-reducing PAGE conditions, a log-linear relationship between protein molecular mass and migration distance was verified, as expected for fully denaturing and reducing SDS-PAGE (R2=0.97, FIG. 14). Separation of dimers was observed, indicating that the buffer conditions may be applicable to analyses of protein-protein interactions. Moderate PAGE performance was achieved; pairs of proteins with molecular mass differences of 51±1.6% (±SD, n=3 separations) were resolvable in ~500 µm separation lengths. In the scWestern array, coefficients of variation for analyte migration distances were within 4% both within and between blocks of arrays (FIG. 7).

The third scWestern attribute was the use of small characteristic lengths for reaction and transport, which facilitated both the blotting and probing stages of the western blot assay. For the blotting stage the followed PAGE, protein bands were covalently immobilized in the photo-active PA gel after PAGE via brief exposure to UV light (45 s). A benzophenone methacrylamide co-monomer crosslinked into the gel conferred this photocapture behavior. Unlike approaches designed to immobilize species to a channel surface, use of a photoactive gel provides a more efficient pseudo-homogeneous 3D reaction environment. To understand the capture efficiency, linearity, and species-specificity of the photoactive PA gel, we first measured the apparent capture efficiency of EGFP expressed in NSCs. After settling, lysis, and PAGE analysis of EGFP-expressing NSC's, the intrinsic fluorescence of the EGFP band was compared with its fluorescence after UV-induced capture and washing (FIG. 1e). A capture efficiency of q=27.5±2.9% was measured (±SD, n=6 blots from experiments on 4 separate days), indicating consistent day-to-day capture performance at efficiencies between those previously determined for native PAGE (η=1.8% for unlabeled, wild-type GFP) and denaturing/reducing PAGE (η>75% for various fluorescently labeled targets) PAGE. The lysis, separation, and blotting steps were completed in 75 s.

Probing of the immobilized protein separations was performed by diffusion of antibodies into the thin PA gel layer. To multiplex the scWestern blots, the microwell arrays were typically organized into 16 "blocks" consisting of 420 microwells; a layout compatible with microarray gaskets allowing application and isolation of unique probing solutions. The probing step consisted of sequential 1 hr incubations of the scWestern array with primary and fluorescently labeled secondary antibody solutions alternating with 45 min buffer wash steps (FIG. 7). Antibody diffusion kinetics through the thin PA gels indicated equilibrium time constants of <5 min (FIG. 13). After probing, the scWestern array was imaged using a fluorescence microarray scanner, scWestern blots of 48 targets in a single sample with 3-plex target quantitation.

Figure 15:
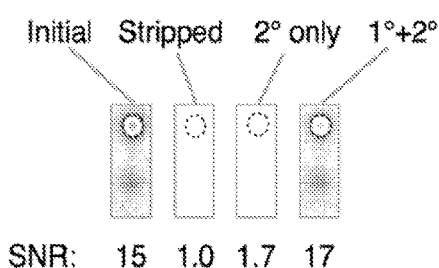
FIG. 15 shows images of stripping and reprobing of single-cell western blot slides according to embodiments of the present disclosure. The "direct" EGFP calibration slide from FIG. 2d was imaged, stripped and reprobed with either an Alexa Fluor 555-labeled secondary antibody only (negative control), or with a primary and Alexa Fluor 555-labeled secondary antibody to EGFP. The signal-to-noise ratio (SNR) of the example reprobed blot approximately matches that of the original probing, while the example negative control blot shows negligible specific signal.

To afford multiplexed target analysis in each cell, the single cell scWestern blot was assessed for reprobing performance using chemical stripping. By incubating the scWestern array with a strongly denaturing buffer after single cell blotting, >10-fold reductions in the signal-to-noise ratios associated with probes to EGFP and β-tubulin were achieved (FIG. 1e). Further, reprobing of EGFP on stripped slides recovered a similar SNR to that of the first probing round, but not for secondary antibody-only controls (FIG. 15).

Single-Cell Western Blotting of Cell Populations

Figure 16:
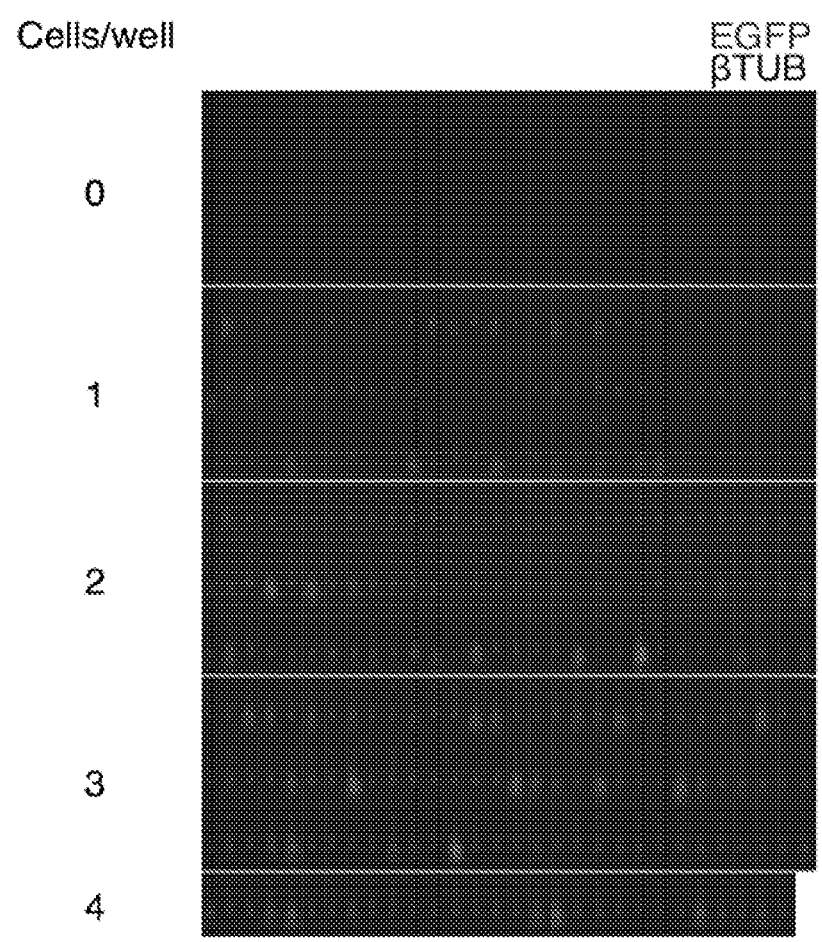
FIG. 16 shows an image of a random sample of blots presented in FIG. 2 ranked by cells-per-well, according to embodiments of the present disclosure. All blots passed semi-automated screening for dust and other fluorescence artifacts.

Experiments were performed to scale the scWestern blot for concurrent analyses from 6,720 microwells. FIG. 2a shows a block of 420 of a total of 5,040 concurrent scWestern blots of EGFP-expressing NSCs for βTUB (Alexa Fluor 647-labeled secondary antibody) and EGFP (Alexa Fluor 555-, RFU: relative fluorescence units). Bright-field micrographs of cells seeded in microwells allowed determination of the number of cells per well. The scWestern blot assay was used to analyze EGFP-expressing neural stem cells (NSCs) spanning 12 blocks of a single slide. 4,128 blots of a possible 5,040 (82%) passed semi-automated gating on dust particles and defects. 1,608 of these (39%) were performed on single cells. Two targets, EGFP and β-tubulin, were probed on the same scWestern array with the resulting scWestern blot readout intensities indexed to the associated microwell occupancy (cell-per-well) value determined via manual scoring (FIG. 2a, and FIG. 16). Automated scoring optimized for gating of single cell-per-well devices was used for all other data sets (see Methods).

The spatial microwell occupancy running average ranged between 0-2.1 cells/well with a mean of 1.1 cells/well (FIG. 2b). The spatial variation in this metric was likely due to non-uniform cell settling densities across the scWestern array. The total fluorescence of the β-tubulin band varied non-linearly with the number of cells per well (FIG. 2b). The non-linearity was attributed to non-Poissonian cell settling statistics that likely reflected cell size bias in microwell seeding (FIG. 2d).

Cell settling statistics and effect on β-tubulin fluorescence distributions—Fano factor describing cell-per-well settling distributions deviated from a Poissonian distribution ($F=\sigma^2/\mu=1$ for Poissonian distributions; $F\sim0.55$-$0.75$ for cell-per-well distributions; FIG. 12). The curtailed cell-per-well distributions may reflect size bias imposed by microwell seeding, which may reduce the per-cell contribution of β-tubulin along the cell-per-well axis. On average, each additional cell above 1 cell/well added 79% and 42% of the β-tubulin contribution of the original cell for 2 and 3 cell/well blots respectively; with standard deviations of 105% and 36% relative to the expected standard deviations based on simple addition of identical 1 cell/well β-tubulin distributions (i.e. $\mu_{f,2's}=\mu_{f,1's}+0.79\mu_{f,1's}$, $\mu_{f,3's}=\mu_{f,2's}+0.42\mu_{f,1's}$; $SD_{f,2's}=SD_{f,1's}+1.05(\sqrt{2}-1)SD_{f,1's}$, $SD_{f,3's}=SD_{f,2's}+0.36(\sqrt{2}-1)SD_{f,1's}$; where $\mu_{f,i's}$ and $SD_{f,i's}$ are the means and standard deviations in β-tubulin fluorescence signal across i cell/well blots, respectively).

β-tubulin fluorescence distributions were well-described by a gamma distribution stemming from a stochastic kinetic model of transcription and translation in a homogeneous population of dividing cells. The model assumed Poissonian mRNA production and exponentially distributed protein burst sizes, yielding: $f(x)=(x^{a-1}e^{-x/b})/(\Gamma(a)b^a)$, where x is the total blot fluorescence, $a=\mu_p^2/\sigma_p^2$ (the inverse of a noise term), $b=\sigma_p^2/\mu_p$ (the Fano factor), and $\Gamma$ is the gamma function. The scWestern β-tubulin data thus agreed with gamma-distributed single cell protein expression profiles for fluorescent protein fusion libraries in E. coli and mammalian cells.

Analytical Performance of the scWestern Blot

To assess the detection performance of scWestern blots, EGFP-expressing NSCs generated by retroviral transduction were assayed, as EGFP expression in these NSCs was expected to vary (FIG. 2c). The EGFP+ cells (for blot signals above technical noise) were 19% and 26.7±1.1% for scWestern blots and flow cytometry assays respectively (±SD, n=3 technical replicates), and dynamic ranges were comparable. Zero cell-per-well scWestern blots from a sparsely seeded region of the slide (blots 4,100-4,128, 0's*) allowed estimation of ideal technical noise. Antibody consumption was ~32 μg of each antibody per scWestern array or 4.8 ng per single-cell blot compared to ~0.5-2 μg of each primary antibody per lane of a conventional slab-gel western blot (FIG. 17).

Figure 17:
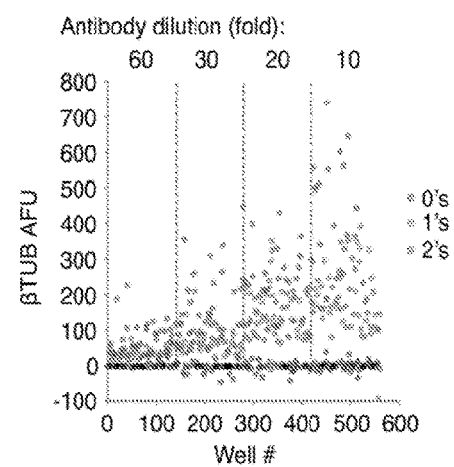
FIG. 17 shows a graph of the effect of antibody fold-dilution on β-tubulin fluorescence readout signal for rat NSCs, according to embodiments of the present disclosure.

Analytical performance of the scWestern blot—Antibody dilution factors of 1:20 were used to provide an acceptable balance between scWestern blot fluorescence signal and reagent consumption for EGFP and β-tubulin (FIG. 17). Under these probing conditions, consumption of 32 μg of each antibody was estimated per slide comprised of 6,720 scWestern blots or 4.8 ng per blot (compared to ~0.5-2 μg of each primary antibody per lane of a conventional slab-gel western blot).

The scWestern blot dynamic range was estimated from the technical noise limit and the maximal cell fluorescence intensity. The scWestern blot technical noise was determined by assessing signal from blots with two characteristics: (i) the microwell contained no cells and (ii) the microwell was distant from microwells that did contain cells. These criteria were chosen since scWestern signals from zero cell-per-well blots that are proximal to finite-cells-per-well assays were ~10 higher than scWestern signals from spatially isolated zero cell-per-well blots (from a pixel number-normalized threshold of $\mu_{zeros}+3\sigma_{zeros}=2.5\times10^4$ to $2.4\times10^5$ molecules). Consequently, in cell populations with high dynamic range targets, a design tradeoff exists between array density and the fidelity of low copy number limit measurements. After determining technical noise limits, ideal dynamic ranges were found to be comparable for the scWestern blots and conventional flow cytometry at 2.9 and 2.6 orders of magnitude, respectively.

Figure 18:
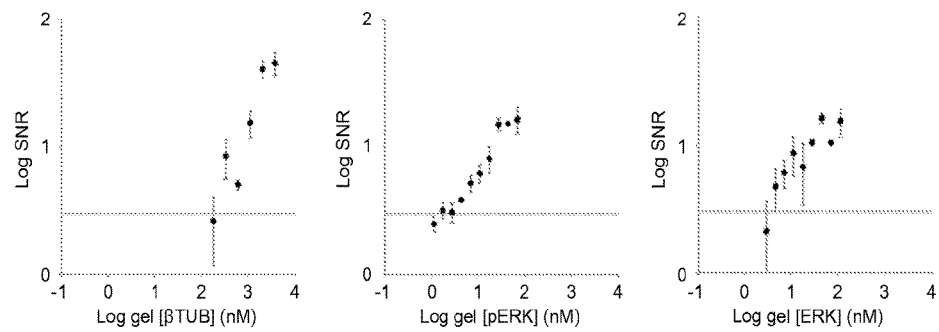
FIG. 18 shows plots of SNR for indirect calibration curves in FIG. 2d, according to embodiments of the present disclosure. Signal-to-noise ratios for indirect calibration curves in FIG. 2d set concentration limits of detection for each purified target at SNR=3.

The linearity and sensitivity of scWestern blot fluorescence readouts was analyzed. "Direct" calibration of EGFP and "indirect" calibration of β-tubulin, pERK, and ERK targets was determined (FIG. 2d). The direct method correlated the number of purified EGFP molecules in a cover-glass-enclosed microwell separation to the probe fluorescence after immunoblotting; while the indirect method used a partition coefficient measurement to infer the number of molecules in a blotted scWestern band from a dot blot-type experiment (FIGS. 8 and 10). The calibration results agreed for EGFP (FIG. 2d), indicating a linear dynamic range of 2.2 orders of magnitude from a limit of detection at 27,000 molecules (45 zmol). This limit of detection matched an "ideal" noise threshold of detection of 25,000 molecules to within 10%, indicating that the detection limit was approximately set by the technical noise associated with the fluorescence microarray scanner. The 27,000 molecule limit of detection was a 45-fold improvement over microwestern arrays, and a 3.2-fold improvement over microfluidic western blotting. Efficient antibody stripping was verified across the indirect EGFP calibration slide (FIG. 2d). Indirect calibration curves for β-tubulin, pERK, and ERK showed linearity over 1.3-1.8 orders of magnitude in the inferred in-gel concentration of each purified standard extending from concentrations yielding SNR=3 ($R^2$=0.94-0.98, FIG. 2d, and FIGS. 10 and 18). Further, estimated physiological concentrations of β-tubulin and ERK corrected for the ~40-fold dilution factor inherent in transfer of proteins from intact cells to blotted bands are within the linear regions of both curves.

Figure 19:
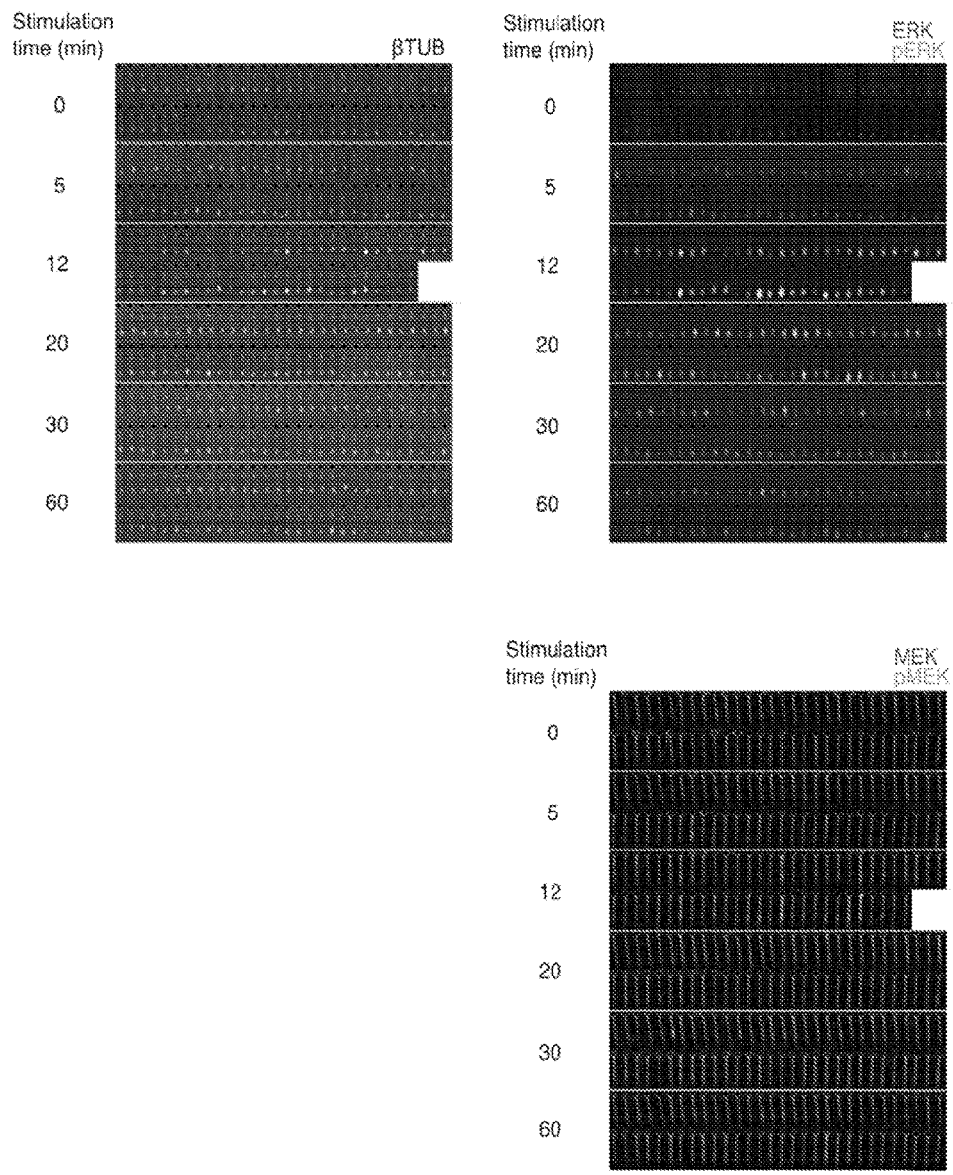
FIG. 19 shows a random sample of blots presented in FIG. 3d, according to embodiments of the present disclosure. All micrographs were for the same set of separations. All blots were for single cell-per-well devices, passed semi-automated screening for dust and other fluorescence artifacts, and for spectral bleed through from EGFP co-probing with ERK. Distinct bands were observed at inferred molecular masses of 38.8±1.0 kDa (pERK), 39.1±0.6 kDa (ERK), 47.4±1.1 kDa (pMEK), and 48.1±1.8 kDa (MEK; ±SD, n=3 separations); nominal masses are pERK/ERK: 43 kDa, pMEK/MEK: 46 kDa.
Figure 20:
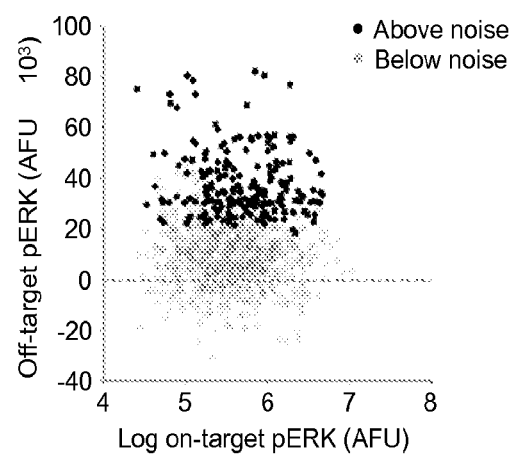
FIG. 20 shows a plot of total single-cell blot fluorescence of the putative off-target pERK band at 103 kDa against the specific fluorescence at the 39 kDa pERK band across all time points of the FGF stimulation experiment in FIG. 3, according to embodiments of the present disclosure.
Figure 21:
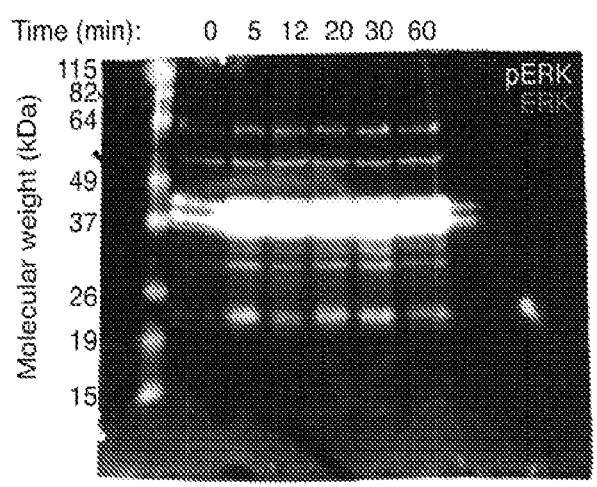
FIG. 21 shows an image of over-exposed western blots of pERK and ERK showing putative non-specific pERK bands at ~58 and 71 kDa, according to embodiments of the present disclosure.

Observation of Cell-to-Cell Heterogeneity in Signaling after FGF Stimulation of NSCs The scWestern array was used to monitor MAPK signaling dynamics in rat NSCs after stimulation by the neural progenitor mitogen FGF. scWestern blots were conducted over a 60 min time course at six intervals (FIG. 3). We first probed for phosphorylated ERK (pERK) and MEK (pMEK) targets, followed by reprobing for total ERK and MEK (FIG. 3a, and FIG. 19). β-tubulin and EGFP allowed estimation of molecular mass for each target. Observed molecular masses for pERK, ERK, pMEK, and MEK were within 10% of their nominal masses. For each pair of phosphorylated and total target readouts, separation profiles corresponded, except for a putative non-specific band in the pERK profile at 103±3 kDa (±SD, n=3 separations). EGFP blot was from a cell in the same row of the array as the other blots, which were each from the same cell. Note an off-target peak at 103 kDa identified by the pERK antibody that did not coincide with an ERK band. This unknown peak showed strong cell-to-cell variability that did not correlate with on-target pERK signal, as corroborated by conventional western blotting (FIG. 3b, and FIGS. 20 and 21).

Non-specific probe binding to off-target species can influence single cell analysis of intracellular proteins (e.g., immunocytochemistry, ICC; flow cytometry). In light of this analytical concern, the contribution of off-target signal in scWestern blots for ERK was further characterized. The non-specific 103 kDa contribution to the total pERK probe signal comprised 13% (maximum of 52%) of the zero time point (unstimulated) scWestern blot signals on average. However, at the 12 min time point corresponding to maximal NSC response to the FGF stimulus, the 103 kDa off-target pERK probe signal included an average of just 0.7% of the total signal (maximum of 18%). Without scWestern blotting the cell-to-cell variability in the contribution of the ~103 kDa off-target peak to immunofluorescence across the stimulation timescale would be difficult to detect as basal levels of ERK phosphorylation are not readily distinguishable from off-target probing in conventional assays without a target-specific knock-down experiment.

Figure 22:
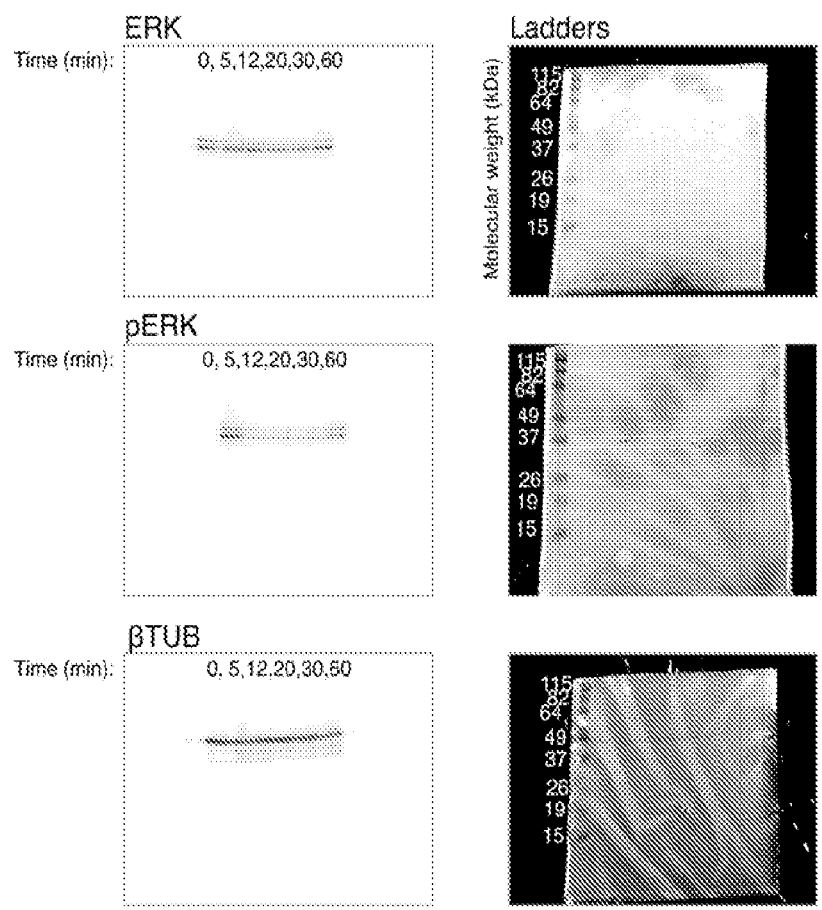
FIG. 22 shows images of full western blots for the stimulation experiment in FIG. 3c, according to embodiments of the present disclosure.

Next, dynamic response measurements from the scWestern blot were compared to conventional slab-gel western blotting. Both the conventional western blot and the scWestern blot showed similar trends in the phosphorylation dynamics of ERK and MEK (FIG. 3c and FIG. 3d, and FIG. 22), and that differences between unstimulated and maximal cell population responses by scWestern blot were statistically significant.

Figure 23:
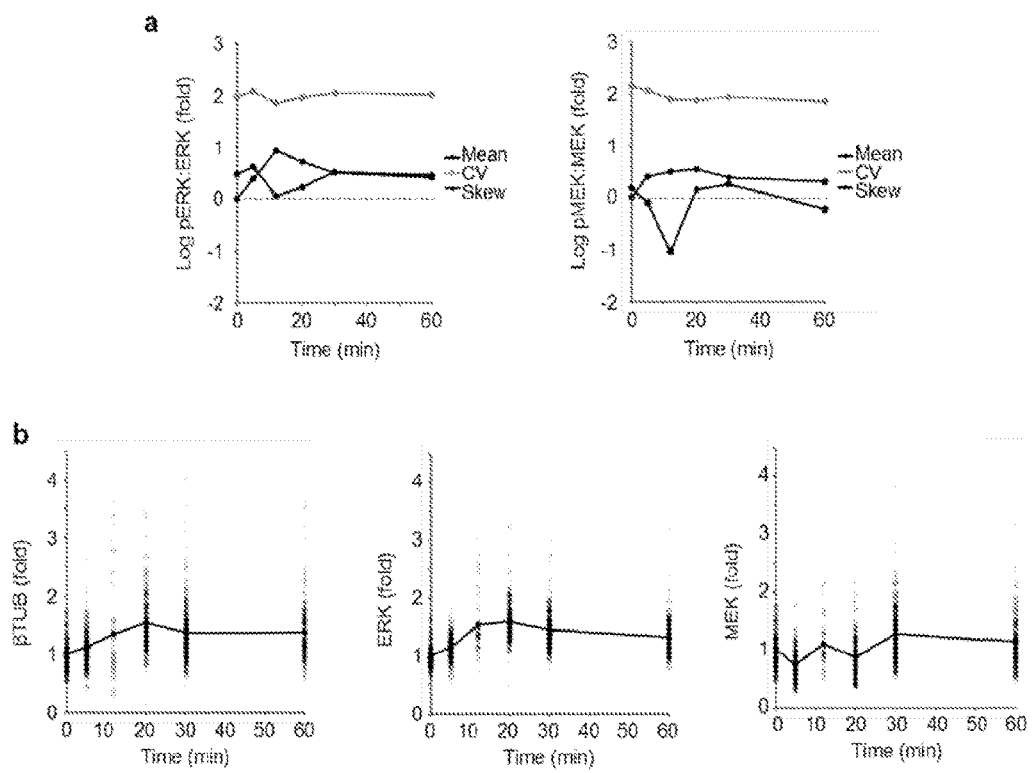
FIGS. 23a and 23b show graphs of the distribution statistics for pERK:ERK and pMEK:MEK, and fold-change dot plots for β-tubulin, ERK, and MEK over the FGF stimulation time course for scWestern blot data in FIG. 3d.
Figure 24:
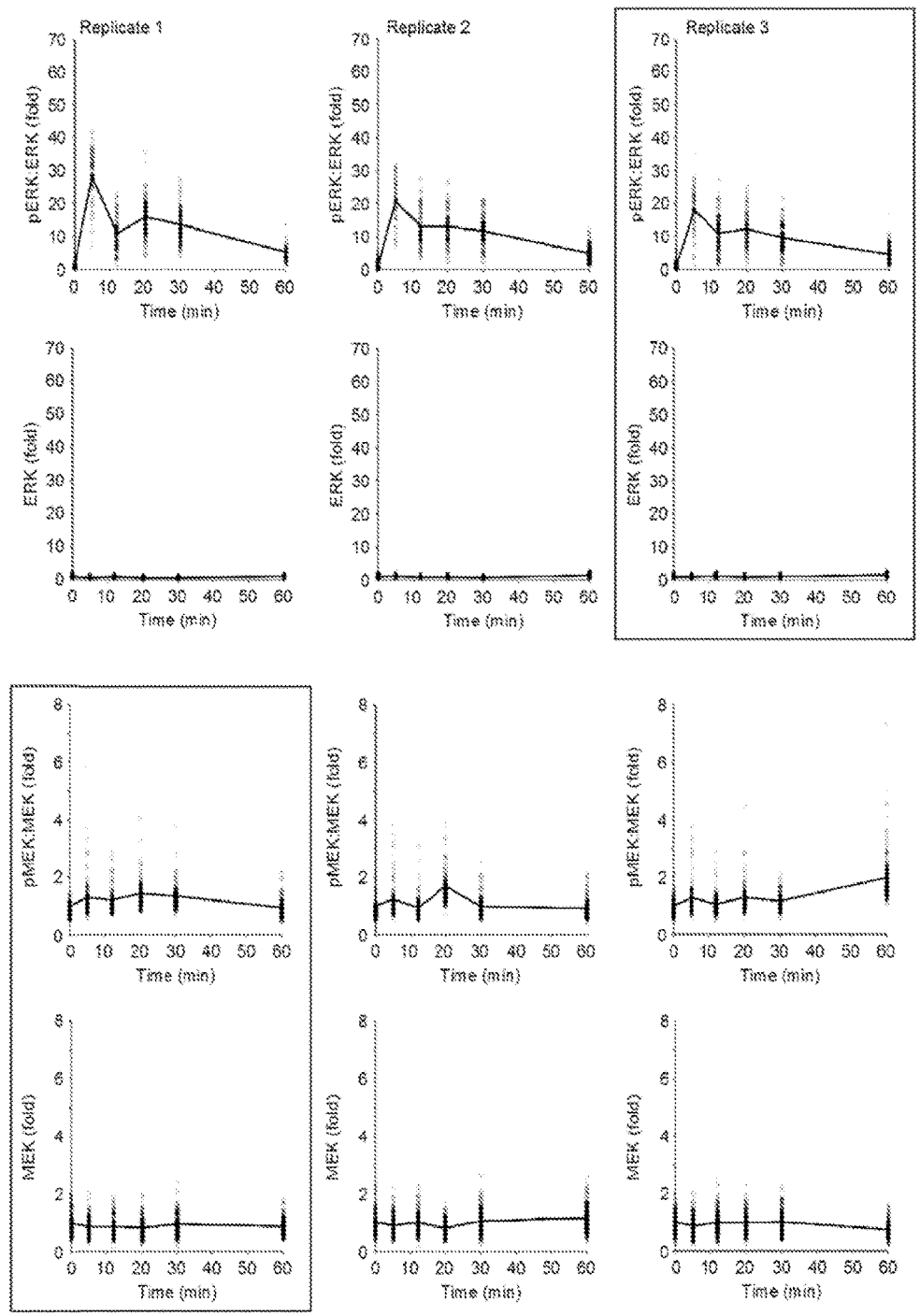
FIG. 24 shows graphs of the full data for the ICC study complementing scWestern blot data for FGF stimulation of NSCs in culture plates in FIG. 3e. Cells were co-probed for pERK/ERK and pMEK/MEK pairs, phosphorylated targets were probed using an Alexa Fluor 555-labeled secondary antibody, and total targets with Alexa Fluor 647-. Data for pMEK/MEK probed separately are presented in FIG. 25. Specific replicates presented in FIG. 3e are shown in boxes. Mean pMEK:MEK ratio does not exceed 2 across the 3 replicates; mean ERK and MEK values show little variation over the stimulation time course.

Statistical analysis of scWestern and ICC data in FGF stimulation experiments (FIG. 3d,e). Fold-change distributions at 12 and 20 min maxima in the single-cell pERK:ERK and pMEK:MEK scWestern blot data respectively differed significantly from corresponding time zero distributions (pERK:ERK: Mann-Whitney U=537, $n_{0\ min}$=186, $n_{12\ min}$=57, P<0.001; pMEK:MEK: Mann-Whitney U=6,884, $n_{0\ min}$=186, $n_{20\ min}$=236, P<0.001). For context, average fold-changes for β-tubulin, ERK, and MEK by scWestern blotting were <1.6 across cell populations at each stimulation time (FIG. 23). Similarly, fold-change distributions at 5 and 20 min maxima for pERK:ERK and pMEK:MEK ICC data (FIG. 24) differed significantly from corresponding time zero distributions (pERK:ERK: Mann- Whitney U=123, $n_{0\ min}$=160, $n_{5\ min}$=115, P<0.001; pMEK: MEK: Mann-Whitney U=6,653, $n_{0\ min}$=184, $n_{20\ min}$=223, P<0.001). For context, average fold-changes for ERK and MEK by ICC were <1.5 across cell populations at each stimulation time (FIG. 24).

Maximal pMEK:MEK phosphorylation trends agreed quantitatively, with ~3.5-fold increase in the ratio at the maximum values versus those at the zero time point. For both assay formats, the response in the pERK:ERK ratio was greater than that observed for the pMEK:MEK ratio, yet the maxima did differ in time between conventional blot densitometry and scWestern fluorescence imaging. A lag in response was observed between the conventional western and scWestern blots that was attributed to intermediate processing steps between stimulation and lysis in the conventional western blot. pERK:ERK distributions had skewnesses of greater than 2.5 for 0, 5, 30, and 60 min time points (FIG. 23), indicating the contribution of rare activated cells to resting populations. These may arise due to constitutive signaling or transient FGF-independent excursions from baseline phosphorylation states. For pERK:ERK and pMEK:MEK phosphorylation responses, skewness was smallest at the 12 min stimulation time point (1.1 and 0.1 respectively) and the pMEK:MEK ratio was normally distributed at the 12 min stimulation time point (Shapiro-Wilk W=0.98, n12 min=57, P=0.58), indicating population-wide approaches to a ceiling of maximum phosphorylation for each target. Cell-to-cell heterogeneity in response kinetics and/or magnitude was high, with interquartile ranges of 7.3 and 3.7 fold-change units at 12 min for pERK:ERK and pMEK:MEK respectively.

Figure 25:
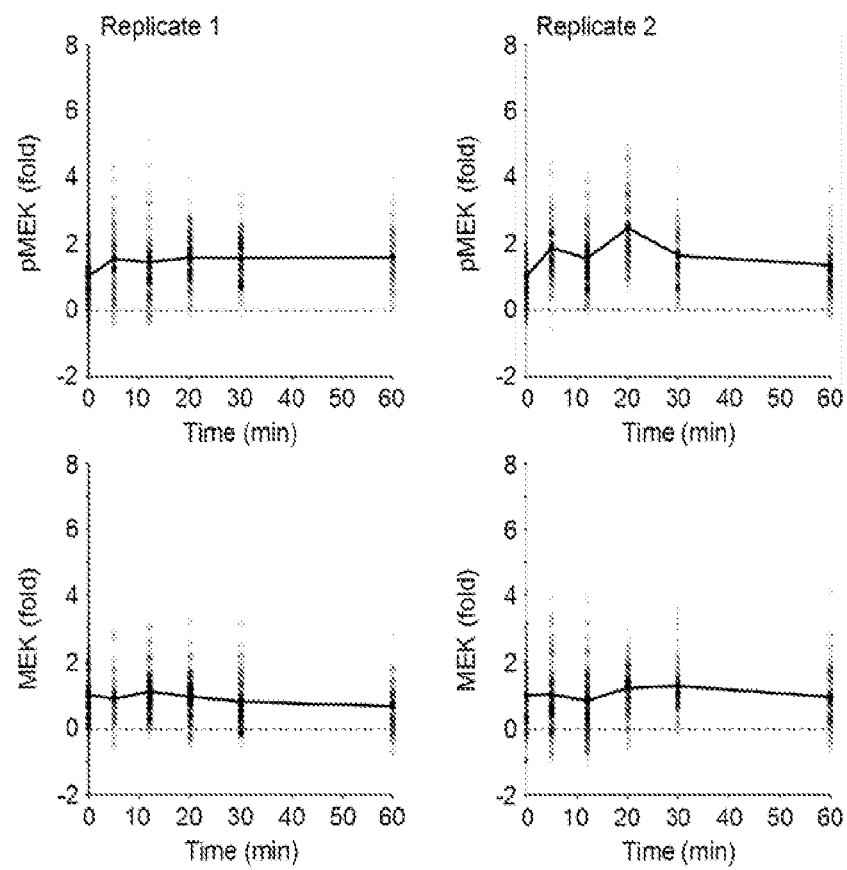
FIG. 25 shows graphs of single-probe pMEK/MEK distributions for the ICC study in FIG. 3e. pMEK and MEK targets were probed in separate cells to examine the possibility of epitope competition between antibodies in the co-probing experiment (Cy3-labeled secondary antibody). No evidence of competition is observed, since mean pMEK fold-change values are in a similar range as mean pMEK:MEK values in FIG. 24.
Figure 26:
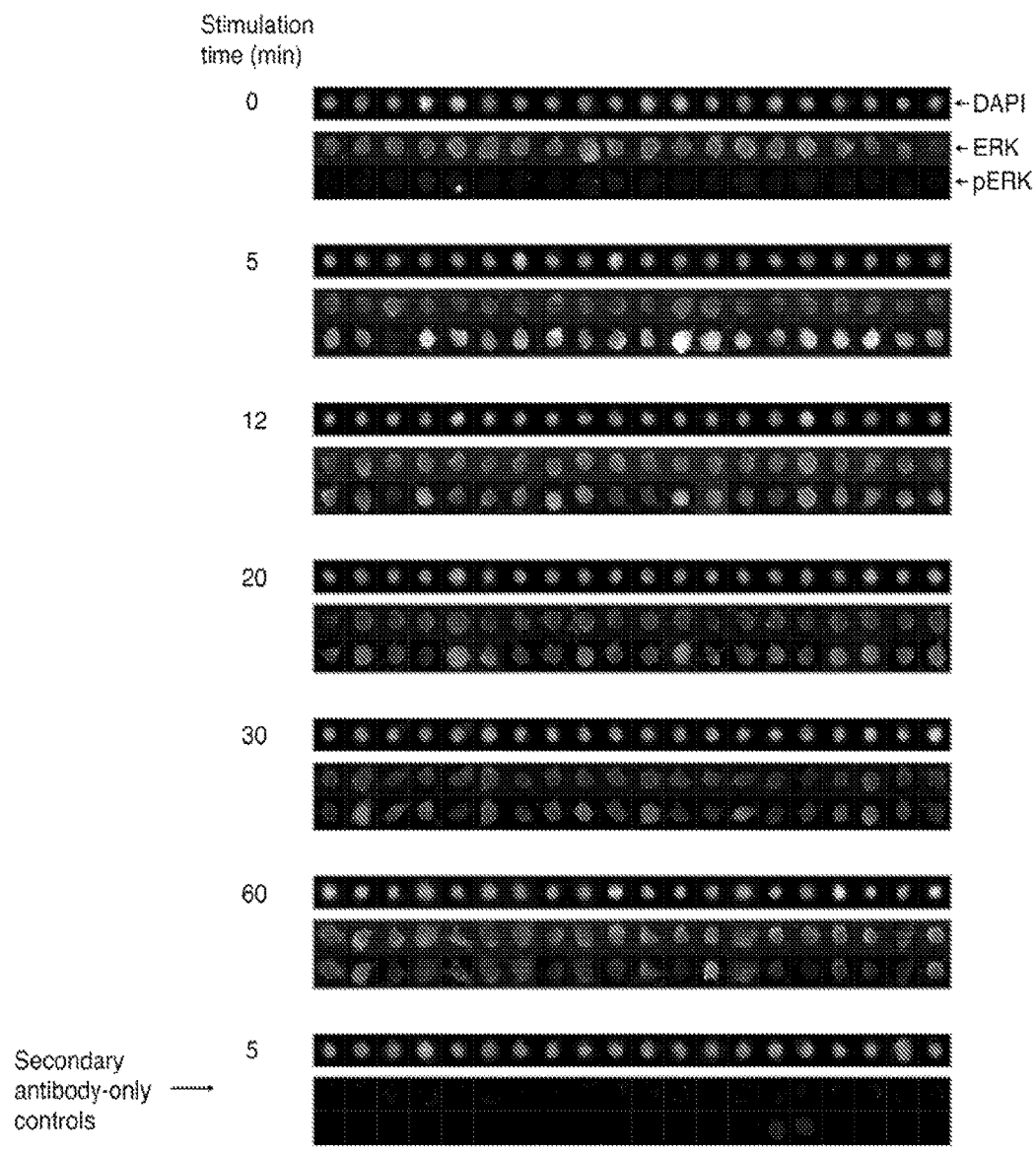
FIG. 26 shows an example of single-cell ROIs chosen at random, as determined by automated analysis of culture plate ICC fluorescence micrographs of pERK and ERK targets for the FGF stimulation experiment in FIG. 3e. See FIG. 24 for experimental details.
Figure 27:
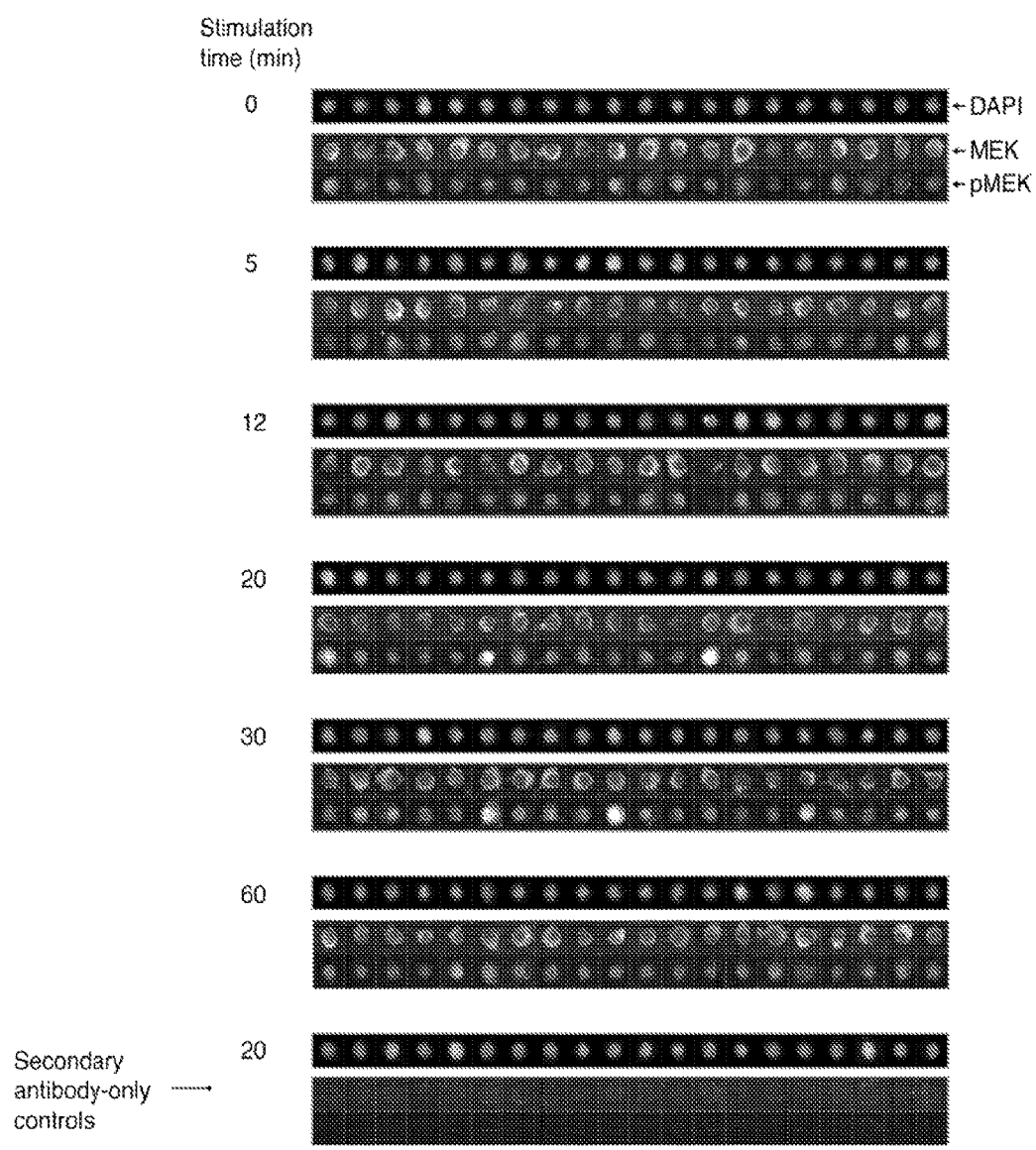
FIG. 27 shows an example of single-cell ROIs chosen at random, as determined by automated analysis of culture plate ICC fluorescence micrographs of pMEK and MEK targets for the FGF stimulation experiment in FIG. 3e. See FIG. 24 for experimental details. Note improper nuclear localization of the primary antibody to pMEK; secondary antibody controls do not account for this apparent localization.

To compare cell-to-cell heterogeneity in protein signaling response to FGF stimulation with a conventional single-cell technique, we analyzed ERK and MEK phosphorylation by high-throughput ICC (FIG. 3e, and FIGS. 24 and 25). pERK:ERK profiles were broadly similar to both scWestern and conventional western blot data. By contrast, pMEK:MEK responses were strongly attenuated with a maximum average fold-change of <2 across three technical replicates, despite being statistically significant. This poor response was attributable to an improper nuclear localization of the pMEK antibody, which conflicted with the expected cytoplasmic localization of pMEK/MEK28 (FIGS. 26 and 27). The off-target specificity of the pMEK antibody in ICC likely obscured the subtle phosphorylation response captured by both scWestern and conventional western blotting.

Cell-to-Cell Heterogeneity During Differentiation of NSCs

Figure 28:
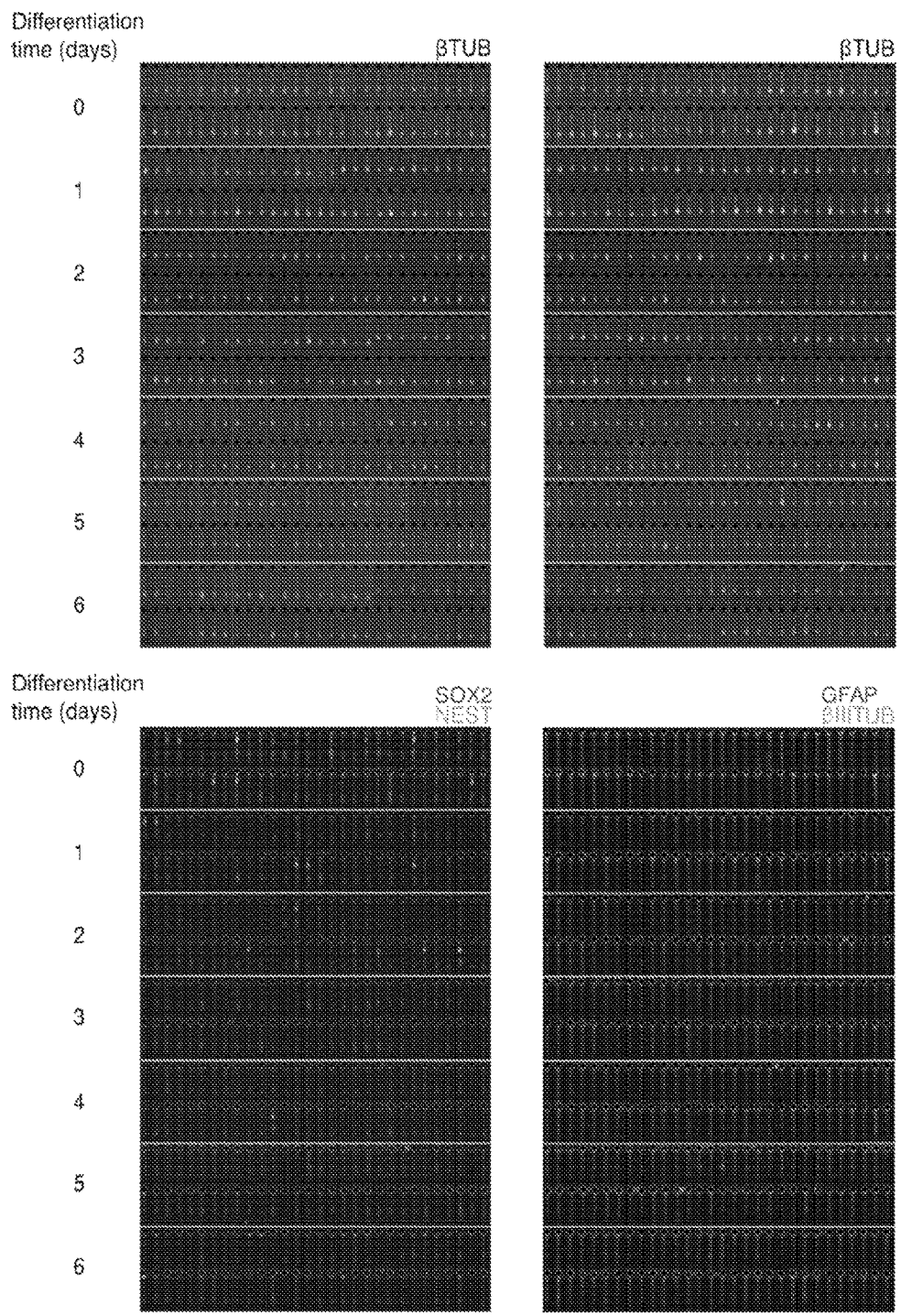
FIG. 28 shows a random sample of single-cell blots presented in FIG. 4f. β-tubulin micrographs matched separations for two-color micrographs within columns. All blots were for single cell-per-well devices, passed semi-automated screening for dust and other fluorescence artifacts, and screening for spectral bleed through from EGFP co-probing with β-tubulin.
Figure 29:
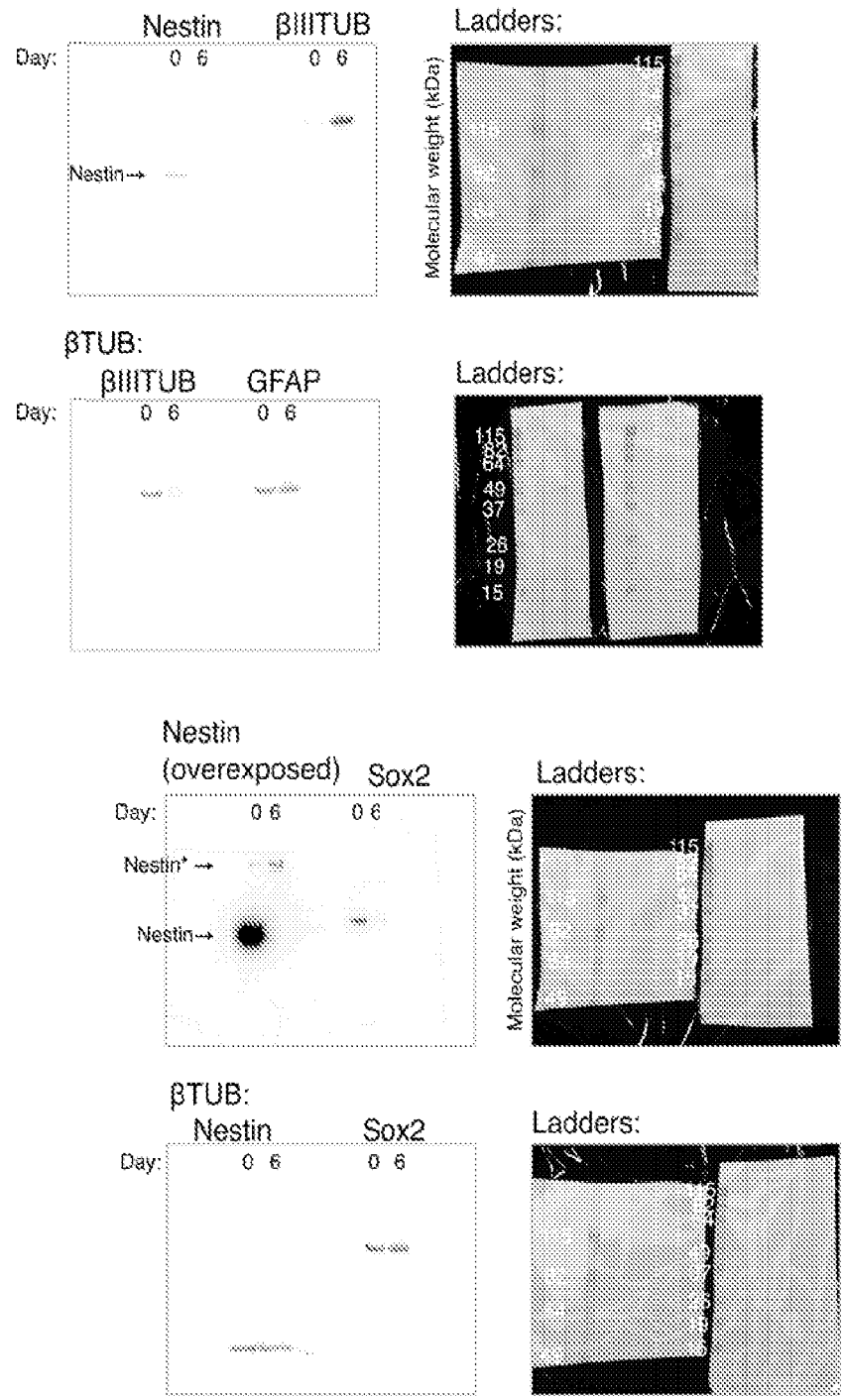
FIG. 29 shows images of full western blots for the differentiation experiment in FIG. 4e.

Large arrays of cells were analyzed via the scWestern blot to study single-cell level nestin (NEST)+/SOX2+ NSC differentiation dynamics towards astrocytic (glial fibrillary acidic protein, GFAP+) and neuronal (βIII-tubulin, βIIITUB+) endpoints over a six day period. NSCs were differentiated towards a mixed neuronal and astrocytic population in culture plates (FIG. 4a). Every 24 h, NSCs were settled into scWestern microwells (FIG. 4b,c) and single-cell blots were conducted over a six day period. The scWestern blots successfully reported specific bands for NEST (95.7±3.5 kDa), SOX2 (43.3±1.9 kDa), βIIITUB (47.2±0.7 kDa), and GFAP (54.0±1.0 kDa, all ±SD, n=3 separations; FIG. 4d, FIG. 28). Each target protein was within 20% of its expected mass (as determined by conventional western blotting), except for SOX2, which differed by 28% from its nominal mass of 33.8 kDa. Differences in the observed SOX2 mass were hypothesized to stem from one of three sources: (i) the high 9.7 pI of the protein and the denaturing, but non-reducing PAGE conditions in the scWestern, (ii) the limited lysis time and differential impact on extraction of SOX2 from the nucleus as compared to the other (all cytosolic) protein targets, (iii) off-target probing. Concordant with literature reports, NEST exhibited two bands in conventional western blotting (82 and 149 kDa for NEST and NEST* respectively, FIG. 4e, FIG. 29); the scWestern blots, however, report only the lower molecular mass band with retention of higher molecular mass material observed in the microwell.

Figure 30:
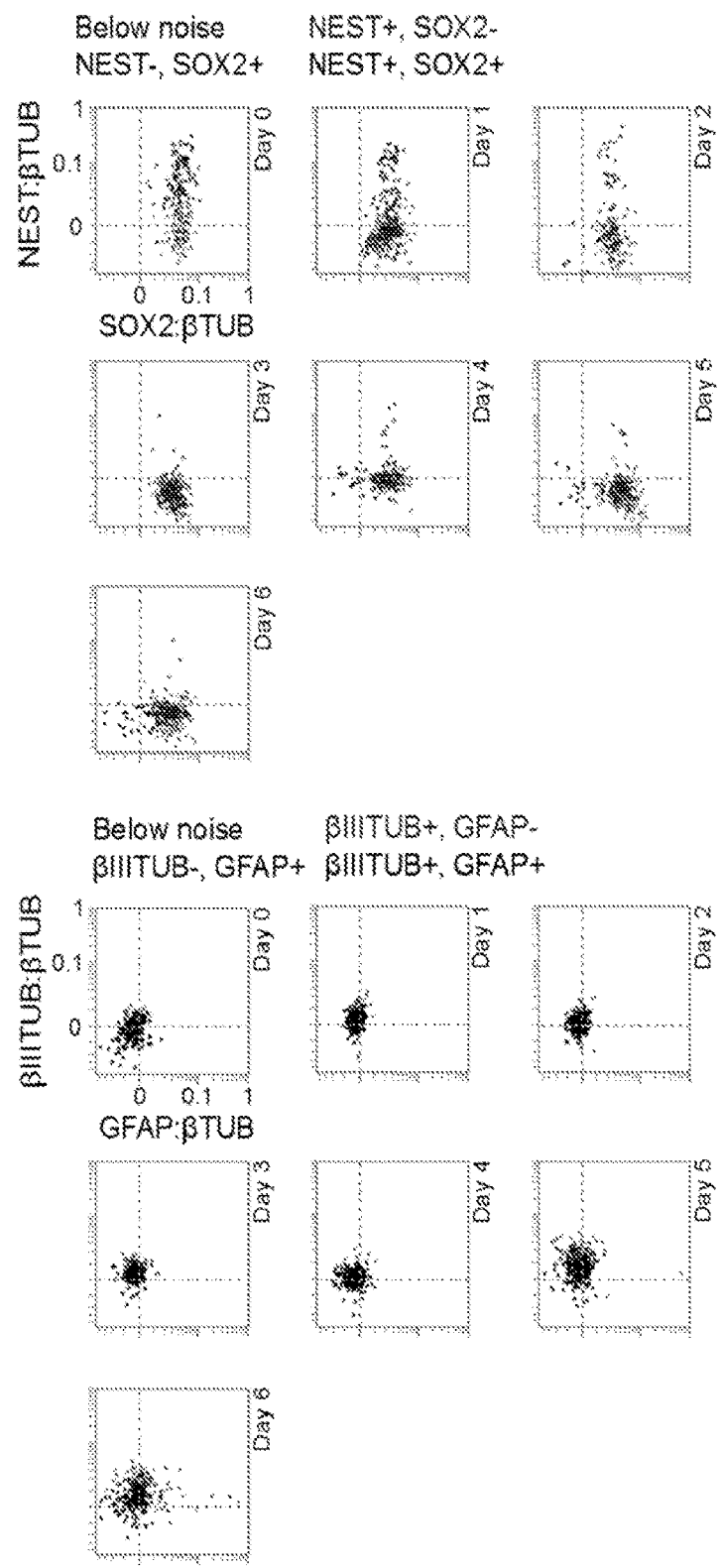
FIG. 30 shows graphs of full stem cell and differentiation marker expression data for FIG. 4f.
Figure 31:
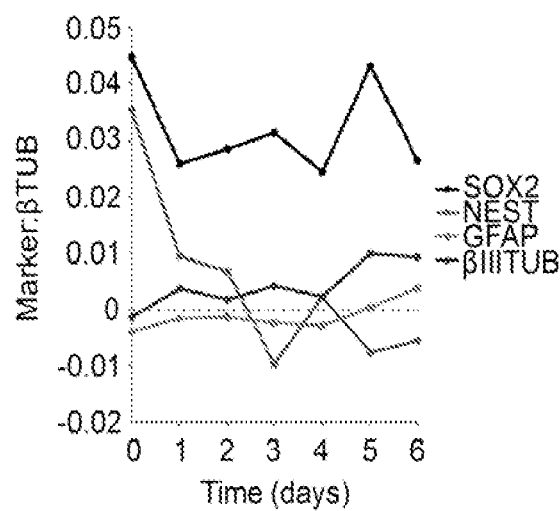
FIG. 31 shows a graph of mean β-tubulin-normalized marker expression levels from scWestern blot data in FIG. 4f.

Conventional western blotting showed >10-fold reductions in NEST (82 kDa band) and SOX2 and >10-fold increases in βIIITUB and GFAP over the six day differentiation time course (FIG. 4e). Similar trends were apparent in β-tubulin-normalized scWestern blot data across the differentiation timescale for NEST, βIIITUB, and GFAP; and for SOX2 to a lesser extent (FIG. 4f, and FIGS. 30 and 31). Single-cell expression levels of NEST and GFAP at days 0 and 6 respectively were particularly heterogeneous, spanning ranges of 22- and 46-fold from their corresponding technical noise thresholds. Percentages of βIIITUB+(neurons) and GFAP+(astrocytes) cell types scored above technical noise in scWestern blots were 53% and 7.1% at day 6. These values matched manually scored counts from a researcher-blinded ICC experiment in the original culture plates to within 15% (Table 1, below), indicating that technical noise thresholds in scWestern blots faithfully delineated marker positive and negative cell states.

No evidence of cell type bias was observed during cell settling in manually scored counts from ICC data in culture plates and scWestern microwells (post-settling). These data indicated that scWestern blotting was robust to cell morphologies as diverse as spheroidal NSCs to highly ramified neuronal and glial cell types (Table 1, below). By culture plate and in-microwell ICC, the counts of NEST+ NSCs dropped from roughly 90 to 40% from day 0 to 6; a similar magnitude to the percentage change in this population was observed by scWestern blotting (53 to 2%). The apparent shift in register of this measurement indicated the capability of the scWestern assay to isolate fluorescence signal from the stimulus-responsive 82 kDa NEST species, whereas ICC measurements may have reached a lower threshold set by expression of the stimulus-unresponsive 149 kDa NEST* species (FIG. 4a). However, both ICC and scWestern assays did not reflect the precipitous drop in SOX2 expression observed by conventional western blotting between days 0 and 6, perhaps indicating off-target antibody readouts in each, further evidenced by the relatively high error in the molecular mass of SOX2 predicted by scWestern blotting.

Discussion

Single-cell western blotting is disclosed herein, which is capable of targeted proteomic analysis of thousands of single cells. The scWestern blot finds use in high-throughput single-cell proteomic tools for investigating basic cellular processes, such as immunocytochemistry, flow cytometry, and the like. Whereas existing protein analysis tools suffer from a shared vulnerability to reagent specificity, inclusion of both separation and immunoprobing steps reduces this vulnerability in scWestern blotting. The scWestern blot facilitates a reduction in the false-positive rate for assays because immunofluorescence detection readouts are supplemented with an assay of secondary characteristics, such as target molecular mass. scWestern blotting also find use in a wide range of inquiry from analysis of rare primary cells in workflows that integrate upstream functional or morphological screens, to antibody library screens for specificity assessment, to quantitation of cell-to-cell variability in response to pharmaceutical agents (e.g., for rare cells, such as circulating tumor cells). Finally, the scWestern blot detailed here is designed for broad adoption, owing to a purposeful absence of complex macro-to-micro interfacing and flow control schemes.

TABLE 2

Percentage of cells (±SD, n = 3 technical replicates, >100 cells scored per replicate) scoring as marker positive by culture plate and in-microwell ICC, and by thresholds set at technical noise levels in single-cell scWestern blot fluorescence data from FIG. 4f at differentiation days 0 and 6. Of interest are endpoint counts for neurons ($\beta$IIITUB$^+$) and astrocytes (GFAP$^+$), in bold.

|        | Culture plate ICC | | In-microwell ICC | | Single-cell blot | |
|--------|------------------|------|------------------|------|------------------|------|
|        | Day 0            | Day 6 | Day 0           | Day 6 | Day 0           | Day 6 |
| SOX2+  | 98.8 ± 2.1       | 99.3 ± 0.7 | 93.3 ± 7.1 | 73.4 ± 4.6 | 97.9 | 89.1 |
| NEST+  | 93.6 ± 4.1       | 46.1 ± 9.4 | 87.3 ± 10.0 | 40.3 ± 2.1 | 52.6 | 1.8 |
| $\beta$IIITUB+ | 2.8 ± 1.4 | 51.8 ± 3.0 | 1.9 ± 1.5 | 61.9 ± 2.1 | 12.3 | 52.7 |
| GFAP+  | 0.0 ± 0.0        | 8.0 ± 2.7 | 0.6 ± 0.2 | 11.9 ± 2.7 | 0.6 | 7.1 |

Example 3

Polymeric Separation Medium that Includes a Circular Arrangement of Microwells

Figure 34:
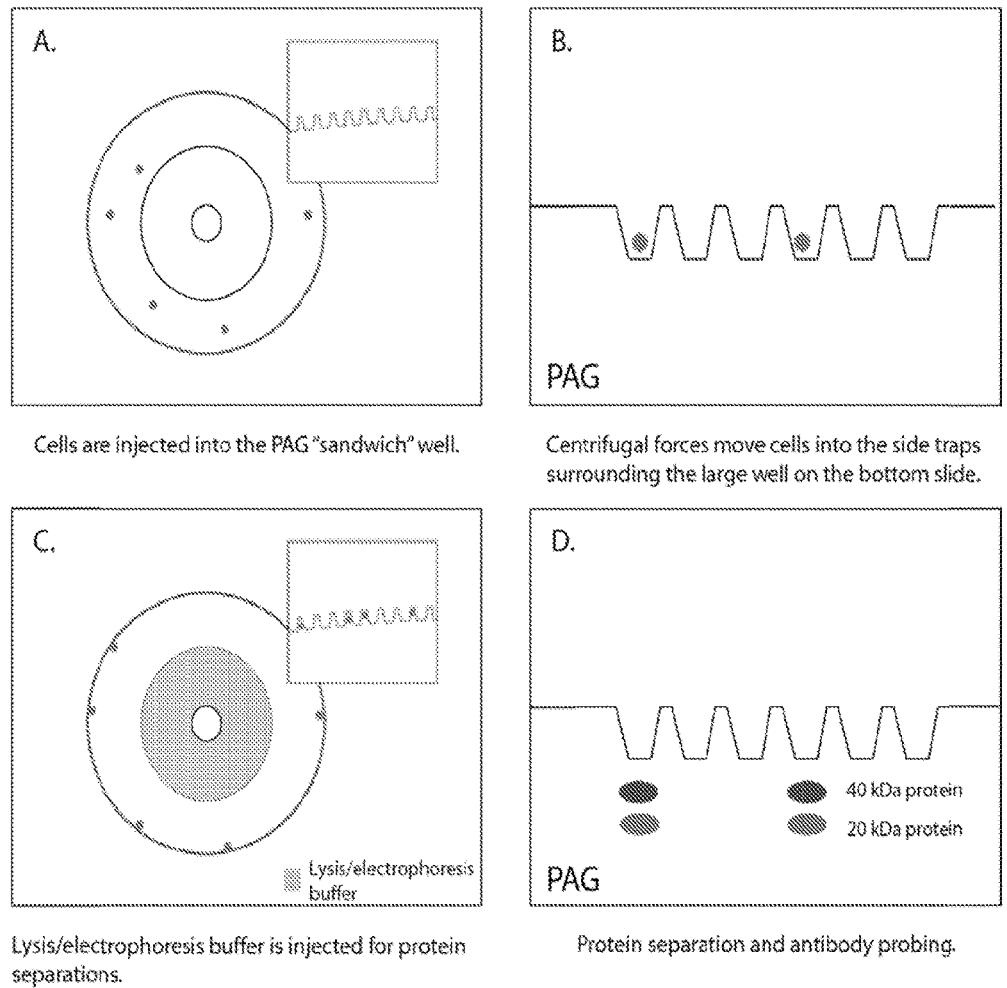
FIG. 34, Panels A-D, show a schematic of a workflow for a cell assay using a device according to embodiments of the present disclosure.
Figure 36A:
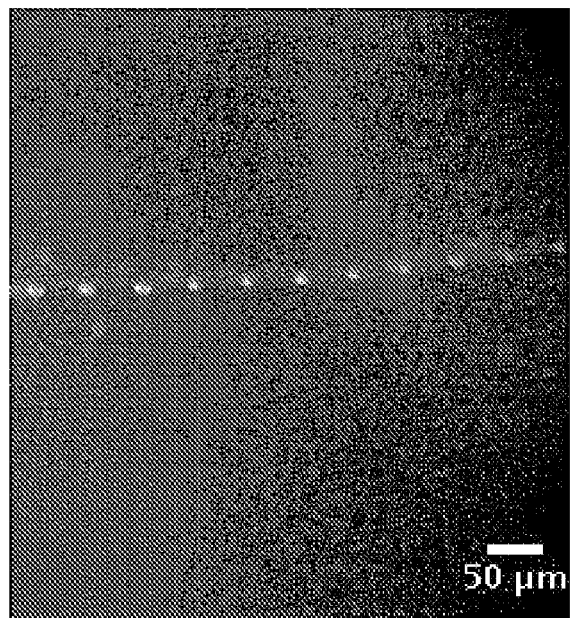
FIGS. 36A and 36B show images of protein movement through polyacrylamide gel (PAG) according to embodiments of the present disclosure.
Figure 36B:
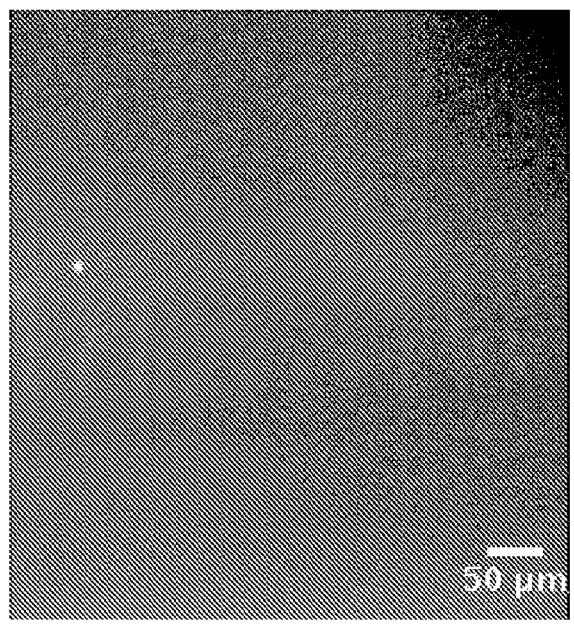

Experiments were performed using a device according to the present disclosure that included a polymeric separation medium having a circular arrangement of microwells, as shown in FIG. 32. The device included two patterned polyacrylamide gel (PAG) slides (FIG. 32). The bottom PAG was patterned with a 12 mm diameter central well, which was surrounded by planar, slanted microwells to capture cells of different sizes (FIG. 33). An 8 mm diameter reservoir was patterned in the top PAG with no microwells, and the two PAG slides were "sandwiched" together to create an enclosed chamber to trap cells. Cells and buffers were injected into the central inlet in the top PAG. Deposited solution initially moved to the void between the 8 and 12 mm well edges (FIG. 32—blue dye; e.g., outer shaded ring) before filling the space in the smaller well (FIG. 32—green dye; e.g., center shaded area). This filling positioned cells close to the side microwells and created a void into which the chamber was filled with buffer or other solutions. Centrifugal forces were used to actively position cells into the microwells. The device quickly settled cells into the microwells for subsequent protein separations. The PAG slides were separated (FIGS. 36A and 36B) and probed for proteins of interest. FIG. 34 shows a schematic of a workflow for analysis of cellular proteins.

Figure 35:
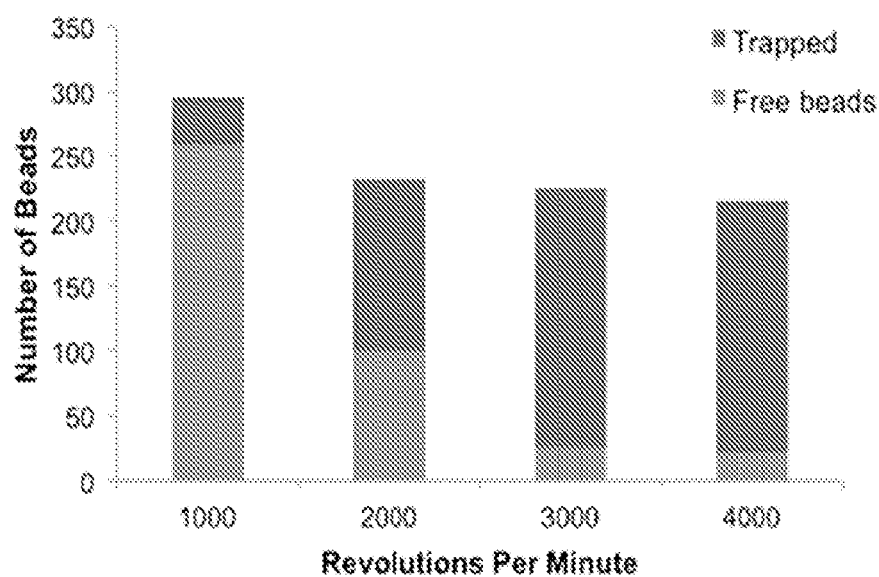
FIG. 35 shows a graph of bead capture rates at various RPMs according to embodiments of the present disclosure. The average capture rate for beads spun at 1000, 2000, 3000, and 4000 RPM is 13, 57, 89, and 90 percent, respectively. The relative centrifugal force at 4000 RPM is ~112 g. (n=2)

Embodiments of the subject device provide for single cell protein analysis for cell populations (e.g., rare cell populations, such as circulating tumor or stem cells). These rare cell populations may require special handling to prevent cell loss. When tested with polystyrene beads, the capture rate for embodiments of the subject device was ~90% when spun for 2 minutes at 4000 RPM or ~112 g (FIG. 35). The rapid cell settling into the microwells and enclosed chamber of the device protected the cells during processing, which facilitated a reduction in cell death. Embodiments of the subject device facilitate the analysis of proteins of interest (e.g., intracellular proteins). Analyzing protein on the single cell level may facilitate detection of variations in cellular behavior.

Embodiments of the present disclosure are further described by, but not limited to, the following clauses:
1. A device comprising:
a polymeric separation medium comprising a plurality of microwells, wherein the polymeric separation medium comprises functional groups that covalently bond to one or more sample components of interest in the separation medium upon application of an applied stimulus.

2. The device of Clause 1, further comprising a solid support contacting a surface of the polymeric separation medium, wherein the device comprises at least one channel through a portion of one or more of the polymeric separation medium and the solid support.

3. The device of Clause 1 or Clause 2, wherein the microwells are arranged as an array of microwells in the polymeric separation medium.

4. The device of any of the preceding Clauses, wherein the microwells comprise an open end on the surface of the polymeric separation medium and an opposing closed end in the polymeric separation medium.

5. The device of Clause 1, wherein the polymeric separation medium comprises a central well comprising a plurality of microwells positioned on the periphery and in fluid communication with the central well.

6. The device of Clause 5, wherein each microwell comprises an open end in fluid communication with the central well and an opposing closed end in the polymeric separation medium.

7. The device of Clause 5 or Clause 6, wherein the microwells are arranged around substantially the entire periphery of the central well.

8. The device of Clause 5, further comprising a solid support carrying the polymeric separation medium, wherein the device comprises at least one channel through a portion of one or more of the polymeric separation medium and the solid support.

9. The device of Clause 5, wherein the polymeric separation medium comprises functional groups that covalently bond to one or more sample components of interest in the separation medium upon application of an applied stimulus.

10. The device of any of the preceding Clauses, wherein the polymeric separation medium comprises 100 or more microwells.

11. The device of any of the preceding Clauses, wherein the microwells are dimensioned to accommodate single cells.

12. The device of Clauses 4 or 6, wherein the open end of the microwell has a width greater than the closed end of the microwell.

13. The device of any of the preceding Clauses, wherein the polymeric separation medium comprises a gel.

14. The device of Clause 13, wherein the gel is shaped as a cuboid.

15. The device of Clause 14, wherein the cuboid has a thickness ranging from 25 to 250 microns.

16. The device of any of the preceding Clauses, wherein the microwell has a depth ranging from 5 to 40 microns and a diameter ranging from 5 to 20 microns.

17. The device of any of the preceding Clauses, wherein the applied stimulus is electromagnetic radiation.

18. The device of Clause 17, wherein the electromagnetic radiation is light.

19. A method comprising:
  contacting a sample with a device of any of the preceding Clauses; and
  applying an electric field to the polymeric separation medium in a manner sufficient to move at least some components of the sample from the microwell into the polymeric separation medium to produce separated sample components in the polymeric separation medium.

20. The method of Clause 19, wherein the polymeric separation medium comprises functional groups that covalently bond to one or more sample components of interest in the separation medium upon application of an applied stimulus.

21. The method of Clause 19 or 20, wherein the sample comprises cells and/or cellular components.

22. The method of any of Clauses 19-21, further comprising lysing the cells to produce the cellular components in the sample.

23. The method of any of Clauses 19-22, further comprising incubating the cells to produce the cellular components in the sample.

24. The method of any of Clauses 19-23, wherein contacting the sample with the polymeric separation medium comprises positioning at least some components of the sample into one or more microwells.

25. The method of Clause 24, wherein the positioning comprises allowing sample components to passively settle due to gravity.

26. The method of Clause 24, wherein the positioning comprises applying a centrifugal force to the polymeric separation medium.

27. The method of Clause 24, wherein the positioning comprises applying an electric field to the polymeric separation medium.

28. The method of Clause 24, wherein the positioning comprises applying a density gradient to the sample.

29. The method of Clause 24, wherein the positioning comprises introducing at least some components of the sample into one or more microwells using a micropipette or a nozzle.

30. The method of Clause 24, wherein the positioning comprises introducing at least some components of the sample into one or more microwells using optical tweezers.

31. The method of Clause 24, wherein the positioning comprises applying a magnetic field to the sample, and wherein at least some of the components in the sample are bound to magnetic beads.

32. The method of Clause 24, wherein the positioning comprises applying a convection flow to the sample.

33. The method of Clause 24, wherein the positioning comprises size selected settling using different shaped and/or sized microwells.

34. The method of Clause 24, wherein at least some components of the sample are contained in droplets, and the positioning comprises introducing the droplets into the microwells.

35. The method of any of Clauses 19-34, further comprising separating the sample components in the polymeric separation medium based on the size of the sample components.

36. The method of any of Clauses 19-34, further comprising separating the sample components in the polymeric separation medium based on the isoelectric point of the sample components.

37. The method of any of Clauses 19-34, further comprising separating the sample components in the polymeric separation medium based on the mass to charge ratio of the sample components.

38. The method of any of Clauses 19-34, further comprising separating the sample components in the polymeric separation medium based on affinity interactions of the sample components.

39. The method of any of Clauses 19-38, further comprising immobilizing the separated sample components in the polymeric separation medium.

40. The method of Clause 39, wherein the immobilizing comprises covalently bonding the separated cellular components to the polymeric separation medium.

41. The method of any of the preceding Clauses, wherein the separated cellular components are covalently bonded to the polymeric separation medium by exposing the polymeric separation medium to ultra-violet (UV) light.

42. The method of any of Clauses 19-41, further comprising detecting the separated sample components.

43. The method of Clause 42, wherein the detecting comprises contacting the separated sample components with an analyte detection reagent.

44. The method of Clause 43, further comprising contacting the separated sample components with a second analyte detection reagent.

45. The method of Clause 43 or 44, wherein the analyte detection reagent comprises a labeled analyte specific binding member.

46. The method of Clause 45, wherein the labeled analyte specific binding member is a labeled antibody.

47. The method of Clause 43, wherein the separated sample component comprises an enzyme and the analyte detection reagent comprises a substrate for the enzyme.

48. The method of Clause 43, wherein the detecting comprises applying an electric field to the polymeric separation medium sufficient to move the analyte detection reagent to the separated sample components.

49. The method of Clause 48, wherein the analyte detection reagent is applied through a top surface of the polymeric separation medium.

50. The method of Clause 58, wherein the analyte detection reagent is applied through a side surface of the polymeric separation medium.

51. The method of any of Clauses 43-50, further comprising removing the analyte detection reagent from the polymeric separation medium.

52. The method of Clause 51, further comprising re-contacting the separated sample components in the polymeric separation medium with an analyte detection reagent.

53. The method of any of Clauses 19-52, further comprising dehydrating the polymeric separation medium.

54. The method of Clause 53, further comprising storing the dehydrated polymeric separation medium for an extended period of time.

55. The method of Clause 54, further comprising rehydrating the polymeric separation medium.

56. The method of Clause 55, further comprising contacting the polymeric separation medium with an analyte detection reagent.

57. The method of any of Clauses 19-56, further comprising imaging the polymeric separation medium to produce an image of the separated cellular components.

58. The method of Clause 57, further comprising identifying a specific cellular component from the image of the separated cellular components.
59. The device of any of the preceding Clauses, wherein the polymeric separation medium is substantially uniform.
60. The device of any of the preceding Clauses, wherein the polymeric separation medium is non-uniform with respect to one or more of pore size, pH gradient, or functionalization of the polymeric separation medium.
61. A kit comprising:
   a device according to any of the preceding Clauses; and
   a packaging containing the device.
62. The kit of Clause 61, further comprising an analyte detection reagent.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A device comprising:
   a polymeric separation medium comprising a plurality of microwells, wherein the polymeric separation medium comprises electromagnetic radiation-activatable functional groups that covalently bond to one or more sample components of interest in the separation medium upon application of electromagnetic radiation, wherein the electromagnetic radiation-activatable functional groups are co-polymerized with the polymeric separation medium, and wherein the microwells have a width of 100 µm or less and a depth of 100 µm or less.

2. The device of claim 1, further comprising a solid support contacting a surface of the polymeric separation medium, wherein the device comprises at least one channel through a portion of one or more of the polymeric separation medium and the solid support.

3. The device of claim 1, wherein the microwells are arranged as an array of microwells in the polymeric separation medium.

4. The device of claim 3, wherein the microwells comprise an open end on the surface of the polymeric separation medium and an opposing closed end in the polymeric separation medium.

5. The device of claim 4, wherein the open end of the microwell has a width greater than the closed end of the microwell.

6. The device of claim 1, wherein the polymeric separation medium comprises a central well comprising a plurality of microwells positioned on the periphery and in fluid communication with the central well.

7. The device of claim 6, wherein each microwell comprises an open end in fluid communication with the central well and an opposing closed end in the polymeric separation medium.

8. The device of claim 6, wherein the microwells are arranged around substantially the entire periphery of the central well.

9. The device of claim 1, wherein the polymeric separation medium comprises 100 or more microwells.

10. A method comprising:
   contacting a sample with a polymeric separation medium of claim 1;

applying an electric field to the polymeric separation medium in a manner sufficient to move at least some components of the sample from the microwell into the polymeric separation medium to produce separated sample components in the polymeric separation medium; and immobilizing the separated sample components in the polymeric separation medium by applying electromagnetic radiation to the electromagnetic radiation-activatable functional groups.

11. The method of claim 10, wherein the sample comprises cells and/or cellular components.

12. The method of claim 11, further comprising lysing the cells to produce the cellular components in the sample.

13. The method of claim 11, further comprising incubating the cells to produce the cellular components in the sample.

14. The method of claim 10, further comprising detecting the separated sample components.

15. The method of claim 14, wherein the detecting comprises contacting the separated sample components with an analyte detection reagent.

16. The method of claim 15, further comprising contacting the separated sample components with a second analyte detection reagent.

17. The method of claim 10, further comprising imaging the polymeric separation medium to produce an image of the separated sample components.

18. The method of claim 10, wherein the contacting the sample with the polymeric separation medium comprises positioning at least some components of the sample into one or more microwells.

19. The method of claim 18, wherein at least some of the components in the sample are bound to magnetic beads, and the positioning comprises applying a magnetic force to the sample.

20. A kit comprising:
a device according to claim 1; and
a packaging containing the device.

21. The device of claim 1, wherein each microwell accommodates a single cell.

22. The device of claim 1, wherein each microwell holds a volume of about one nanoliter.

23. The device of claim 1, wherein the device is configured for single cell analysis.

24. The device of claim 1, wherein the electromagnetic radiation-activatable functional groups comprise benzophenone functional groups.

* * * * *